United States Patent [19]

Mastri et al.

[11] Patent Number: 5,762,256
[45] Date of Patent: Jun. 9, 1998

[54] SURGICAL STAPLER

[75] Inventors: Dominick L. Mastri, Bridgeport; Frank J. Viola, Sandy Hook; Thomas W. Alesi, Jr., New Fairfield; Robert J. Geiste, Milford, all of Conn.

[73] Assignee: United States Surgical Corporation, Norwalk, Conn.

[21] Appl. No.: 520,202

[22] Filed: Aug. 28, 1995

[51] Int. Cl.⁶ .................................................. A61B 17/068
[52] U.S. Cl. ........................ 227/176.1; 227/19; 227/178.1
[58] Field of Search ........................... 227/175.1, 176.1, 227/178.1, 180.1, 19

[56] References Cited

U.S. PATENT DOCUMENTS

| Re. 34,519 | 1/1994 | Fox et al. . |
| 3,079,606 | 3/1963 | Bobrov et al. . |
| 3,490,675 | 1/1970 | Green et al. . |
| 4,244,372 | 1/1981 | Kapitanov et al. . |
| 4,429,695 | 2/1984 | Green . |
| 4,589,413 | 5/1986 | Malyshev et al. . |
| 4,608,981 | 9/1986 | Rothfuss et al. . |
| 4,610,383 | 9/1986 | Rothfuss et al. . |
| 4,633,861 | 1/1987 | Chow et al. . |
| 4,633,874 | 1/1987 | Chow et al. . |
| 4,700,703 | 10/1987 | Resnick et al. ............ 227/19 |
| 4,863,088 | 9/1989 | Redmond et al. . |
| 4,892,244 | 1/1990 | Fox et al. . |
| 4,991,764 | 2/1991 | Mericle . |
| 5,065,929 | 11/1991 | Schulze et al. . |
| 5,074,454 | 12/1991 | Peters . |
| 5,083,695 | 1/1992 | Foslien et al. . |
| 5,111,987 | 5/1992 | Moeinzadeh et al. . |
| 5,129,570 | 7/1992 | Schulze et al. . |
| 5,141,144 | 8/1992 | Foslien et al. . |
| 5,307,976 | 5/1994 | Olson et al. . |
| 5,312,023 | 5/1994 | Green et al. . |
| 5,318,221 | 6/1994 | Green et al. . |
| 5,326,013 | 7/1994 | Green et al. . |
| 5,332,142 | 7/1994 | Robinson et al. . |
| 5,376,095 | 12/1994 | Ortiz . |
| 5,397,046 | 3/1995 | Savage et al. . |
| 5,415,334 | 5/1995 | Williamson, IV et al. . |
| 5,415,335 | 5/1995 | Knodell, Jr. . |
| 5,433,721 | 7/1995 | Hooven et al. . |
| 5,467,911 | 11/1995 | Tsuruta et al. . |
| 5,474,566 | 12/1995 | Alesi et al. . |
| 5,486,185 | 1/1996 | Freitas et al. . |
| 5,487,500 | 1/1996 | Knodel et al. . |
| 5,507,426 | 4/1996 | Young et al. . |
| B1 5,040,715 | 4/1994 | Green et al. . |

FOREIGN PATENT DOCUMENTS

| 0484677 | 5/1992 | European Pat. Off. . |
| 0589306 | 3/1994 | European Pat. Off. . |
| 0591946 | 4/1994 | European Pat. Off. . |
| 0656188 | 6/1995 | European Pat. Off. . |

*Primary Examiner*—Scott A. Smith

[57] ABSTRACT

A surgical device is described herein that can be used to fire different types and sizes of disposable loading units. In a preferred embodiment, the device applies parallel rows of surgical fasteners to body tissue and concomitantly forms an incision between the rows of staples during an endoscopic or laparoscopic surgical procedure. The device can be utilized with disposable loading units configured to apply linear rows of staples measuring from about 15 mm in length to about 60 mm in length and can be used to fire disposable loading units containing surgical clips and individual staples.

23 Claims, 38 Drawing Sheets

Fig. 6

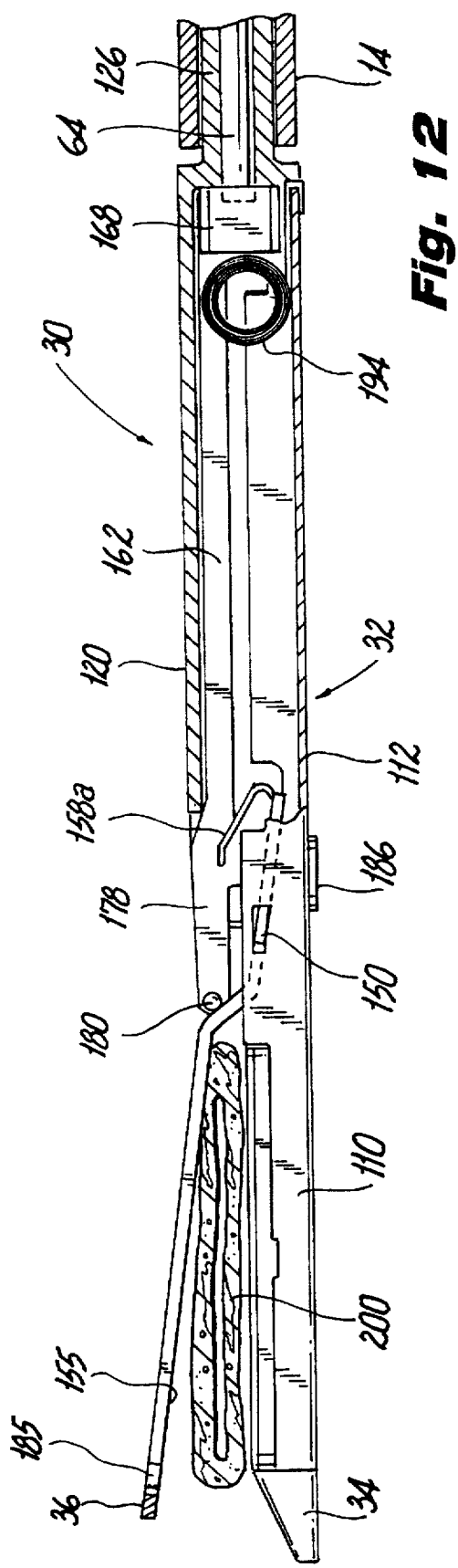
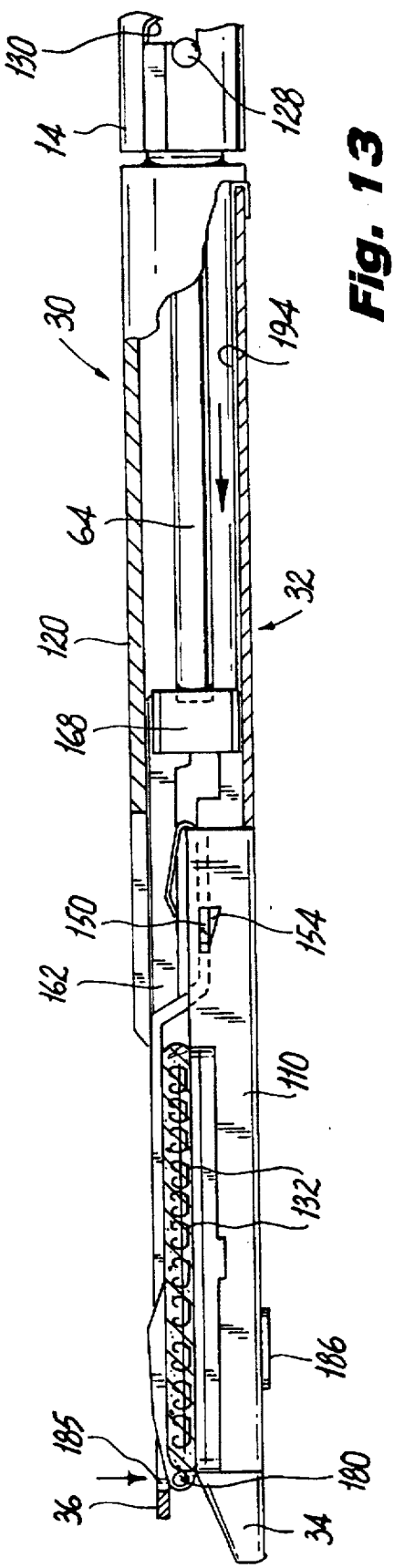
Fig. 12
Fig. 13

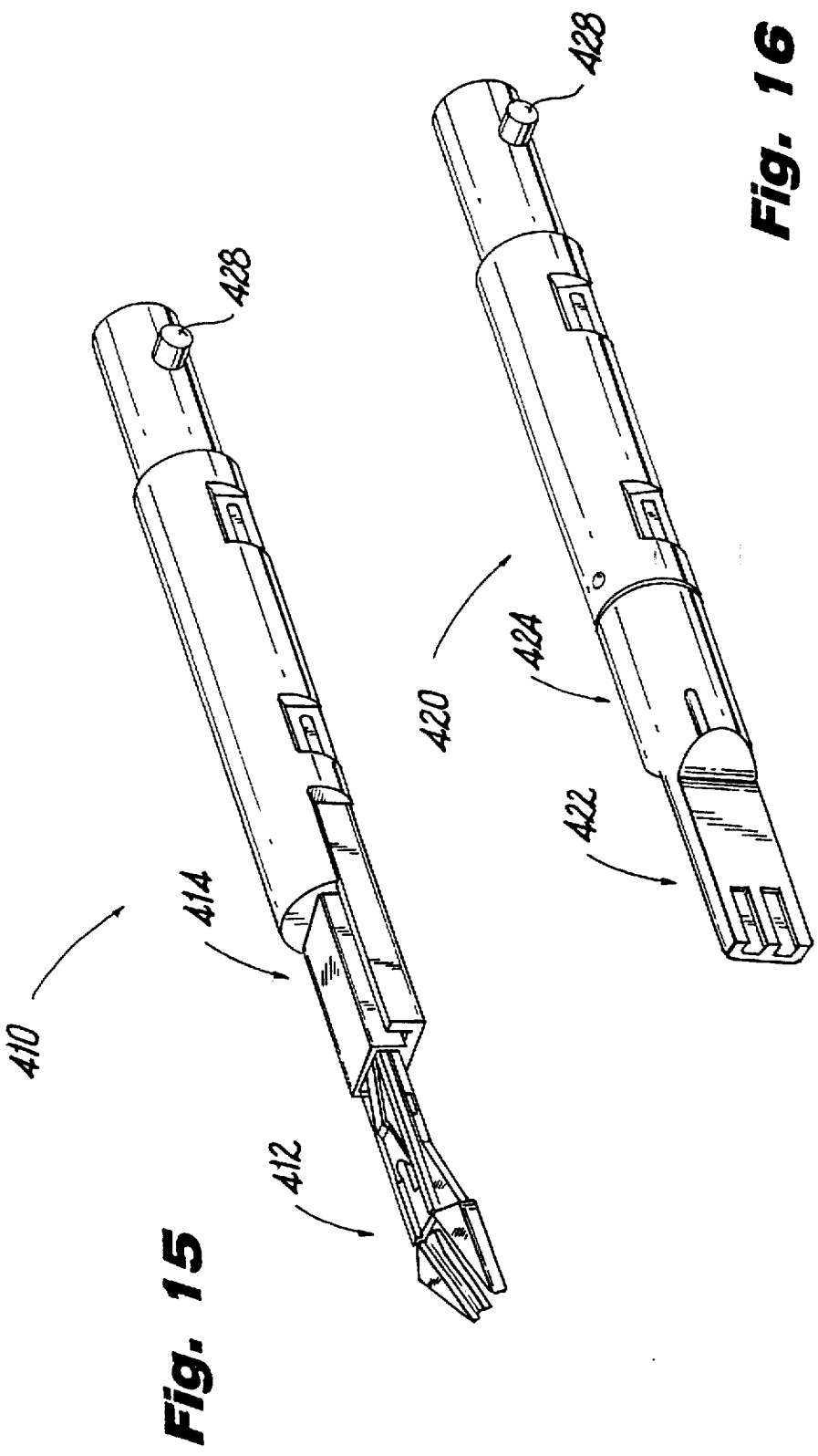

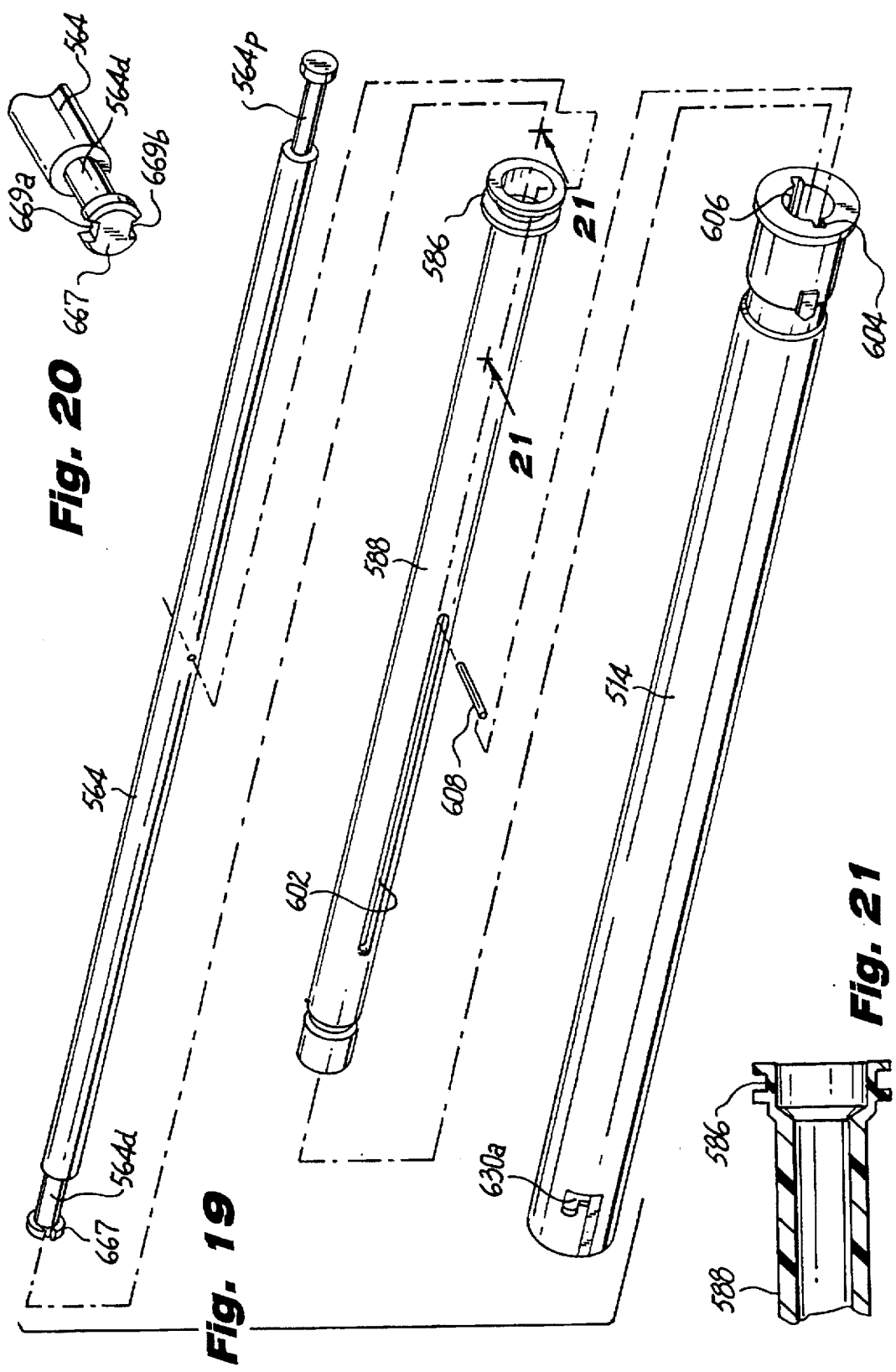

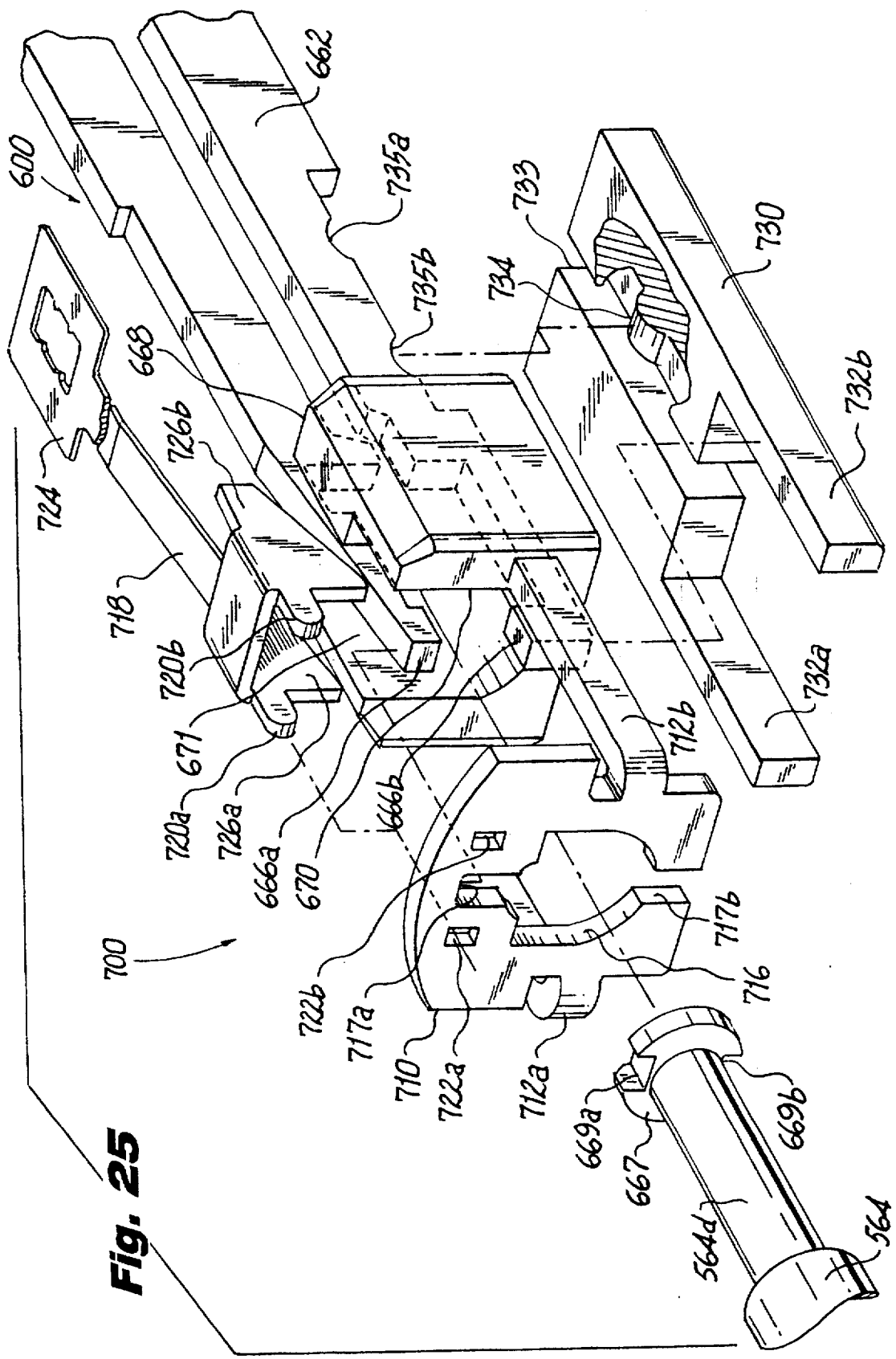

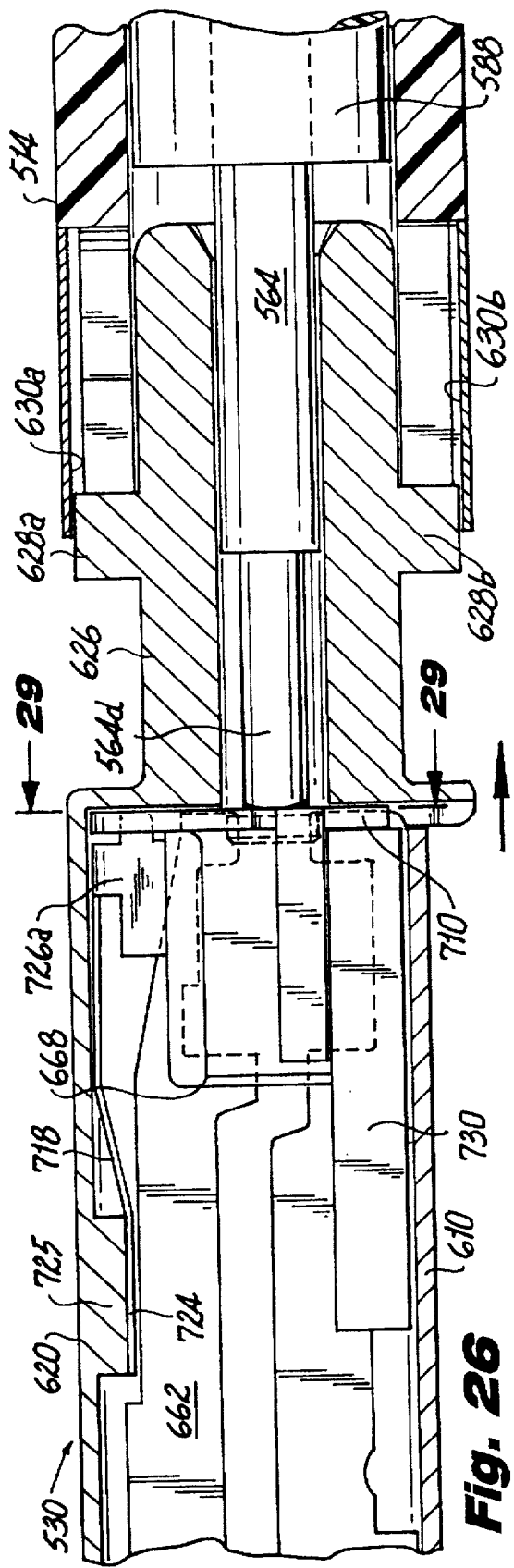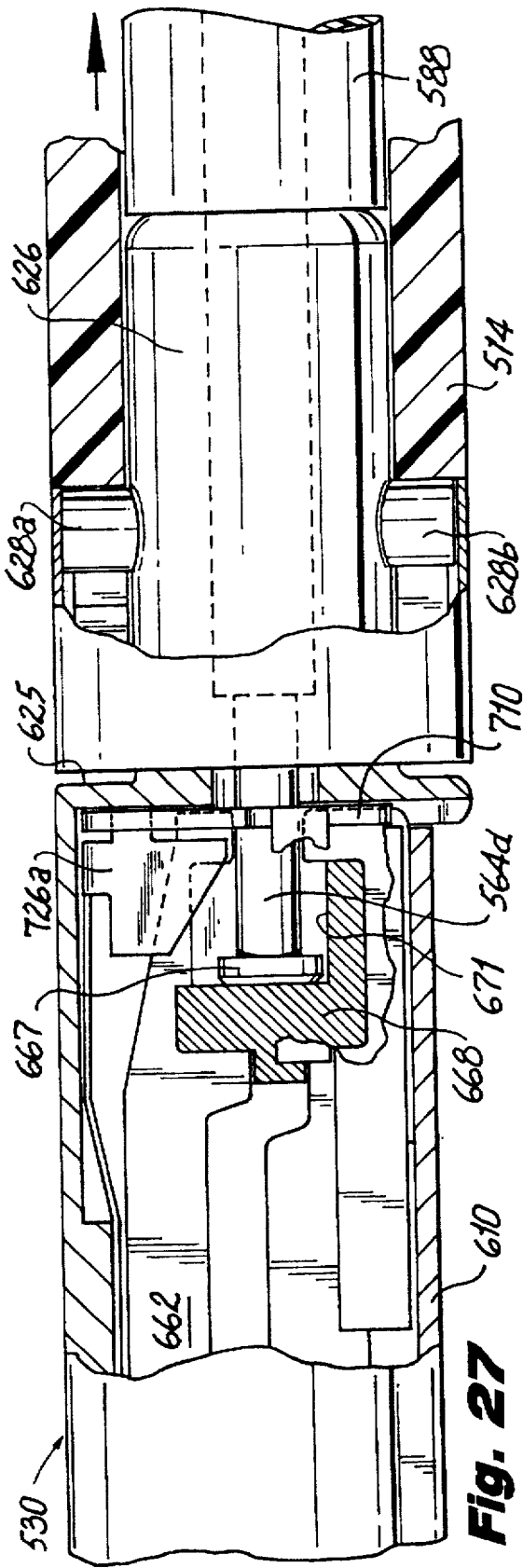

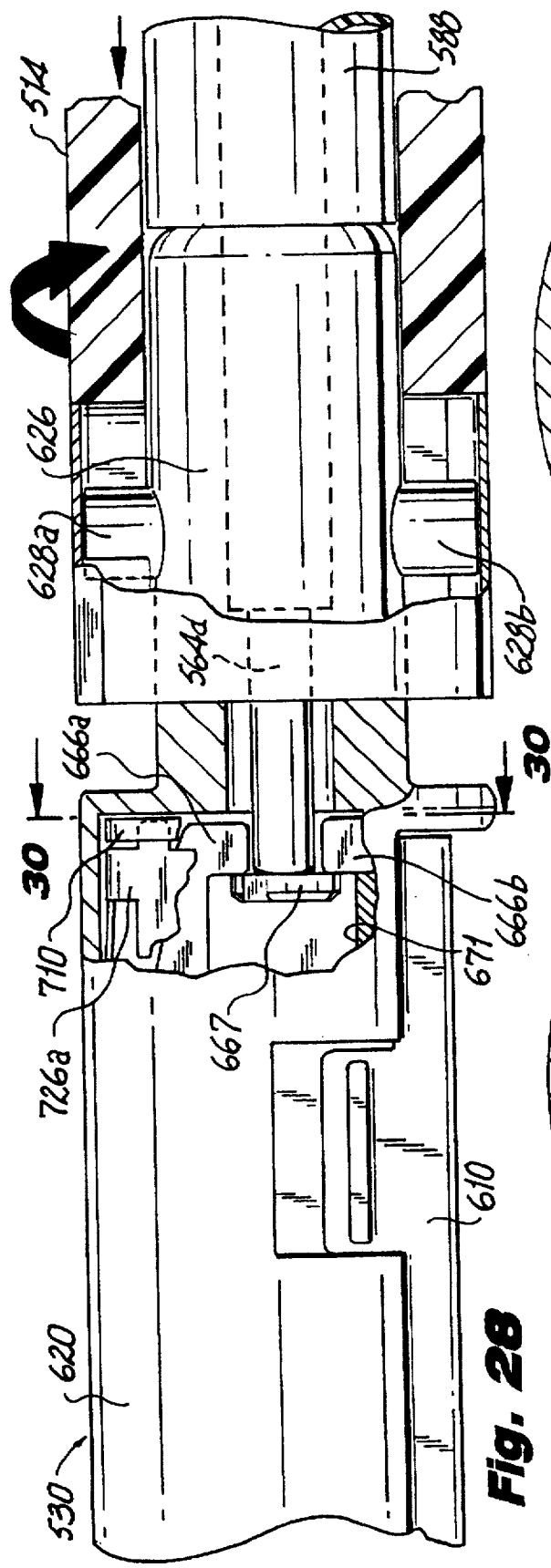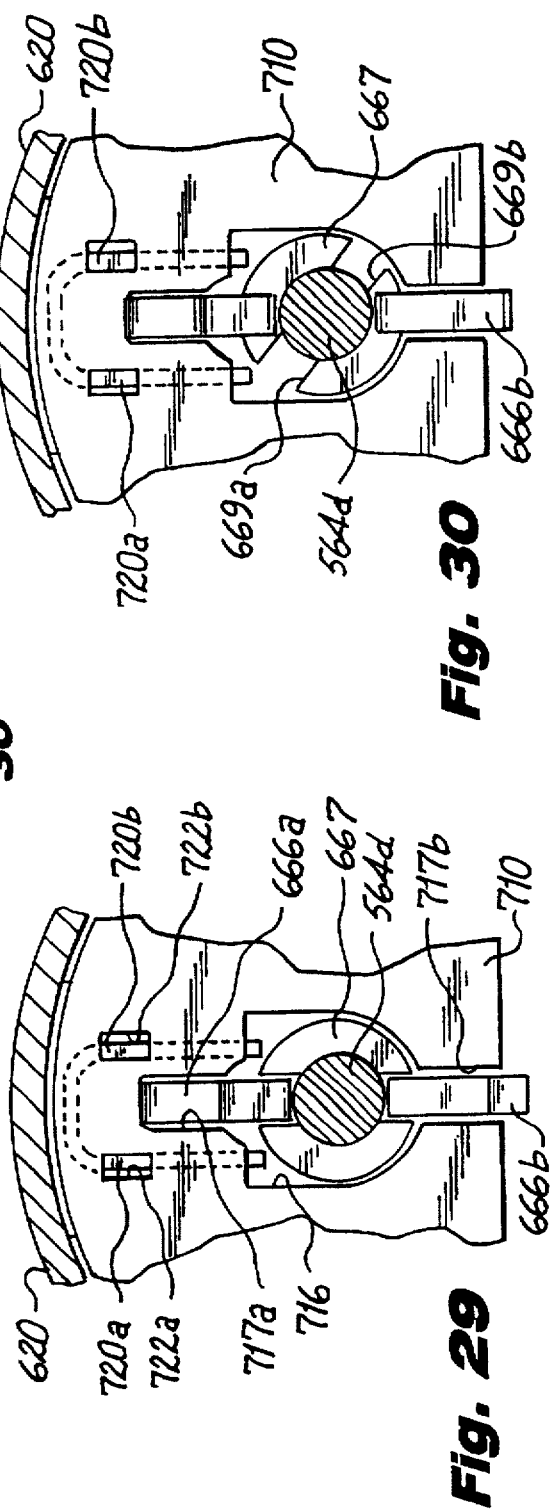

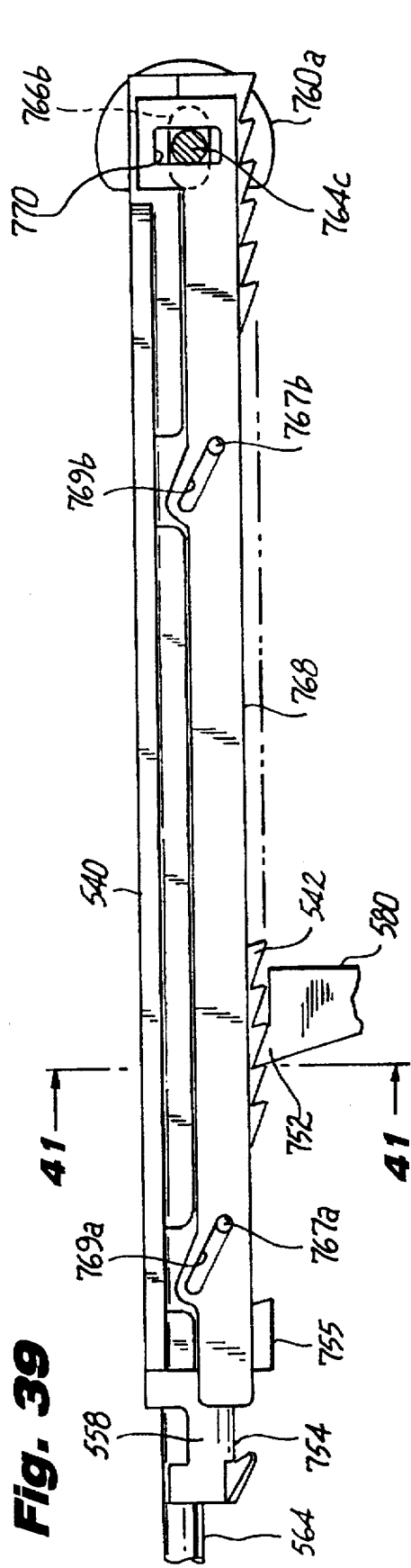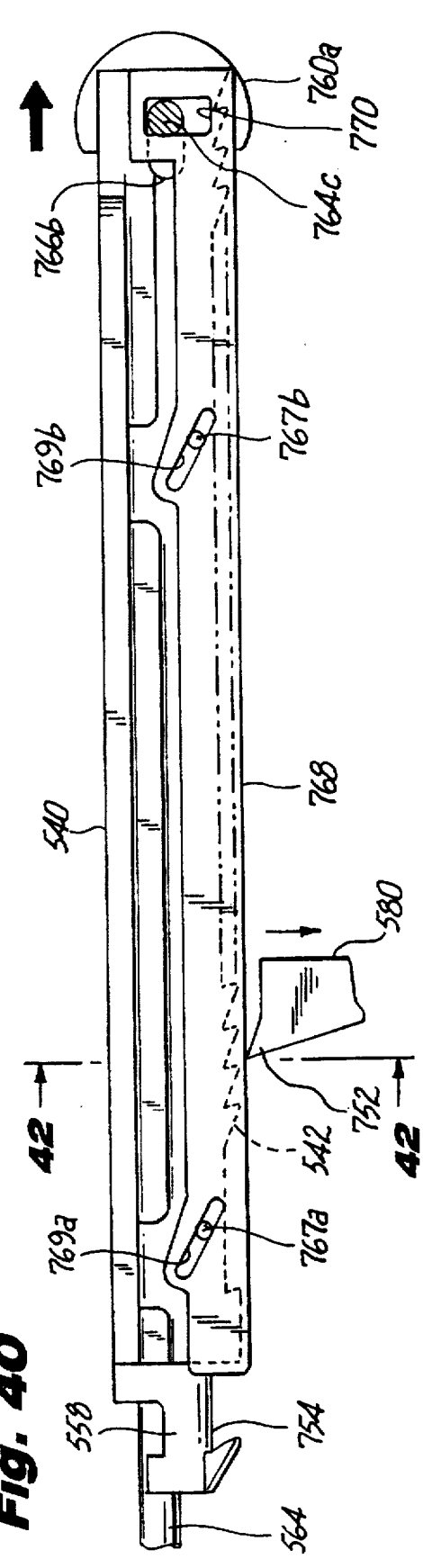

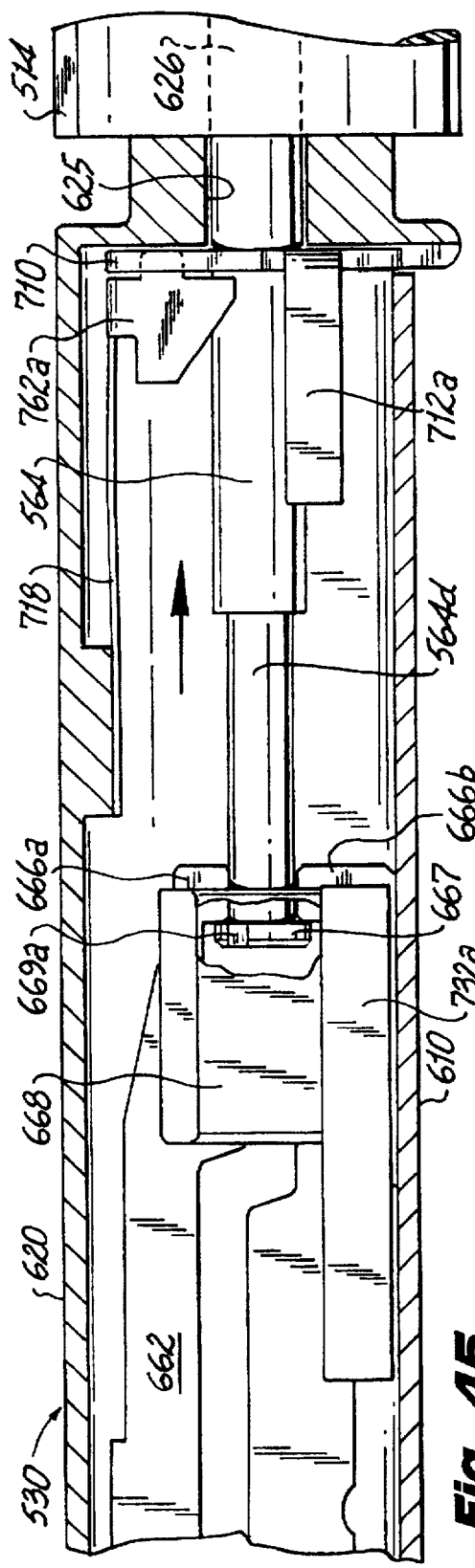
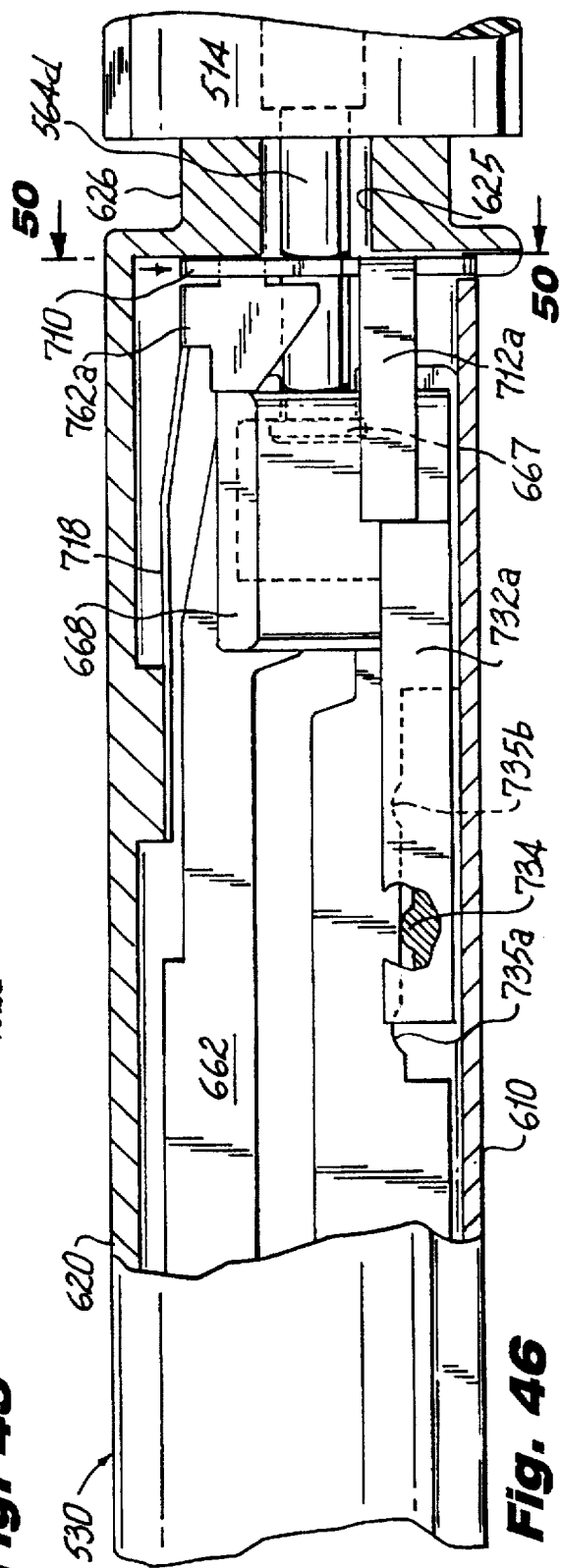

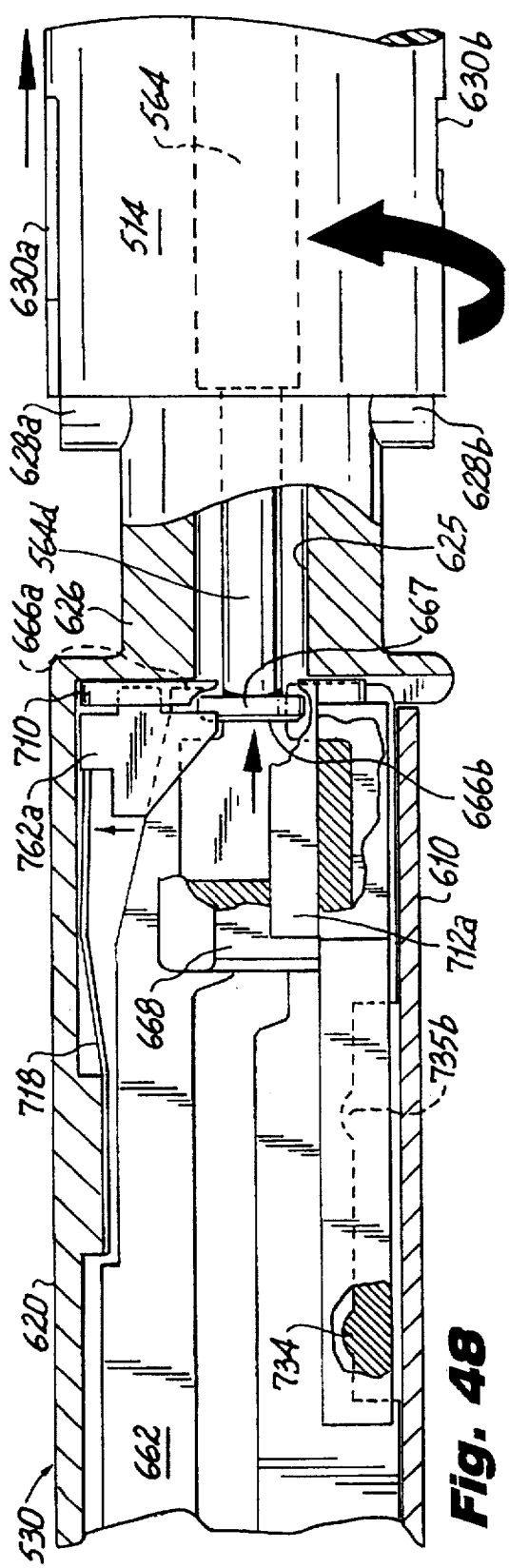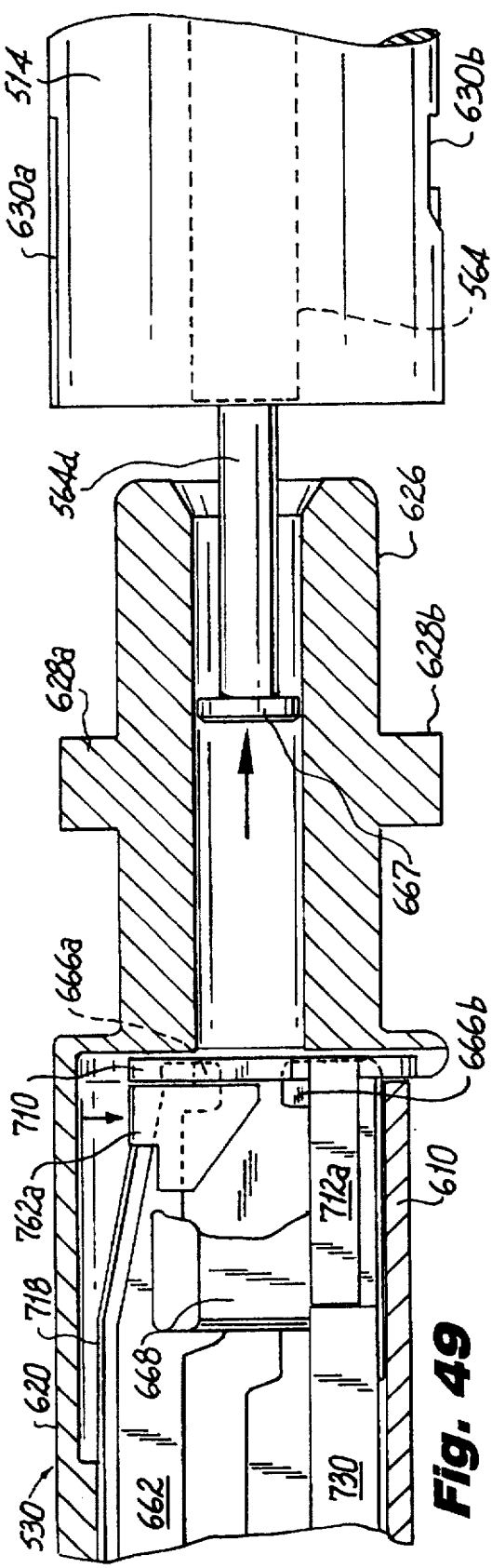
Fig. 48
Fig. 49

SURGICAL STAPLER

BACKGROUND

1. Technical Field

This application relates to a surgical stapling apparatus, and more particularly, to an apparatus for sequentially applying a plurality of surgical fasteners to body tissue and optionally incising the fastened tissue.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

A later stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of such staplers are disclosed in U.S. Pat. Nos. 4,429,695 and 5,065,929.

Each of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. B5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat. No. 5,332,142 (Robinson, et al.).

U.S. Surgical, the assignee of the present application, has manufactured and marketed endoscopic stapling instruments, such as the Multifire ENDO GIA* 30 and Multifire ENDO GIA* 60 instruments, for several years. These instruments have provided significant clinical benefits. Nonetheless, improvements are possible, for example, by reducing the cost and complexity of manufacture.

Current laparoscopic linear stapling devices are configured to operate with disposable loading units (U.S. Surgical) and staple cartridges (Ethicon) of only one size. For example, individual linear staplers are presently available for applying parallel rows of staples measuring 30 mm, 45 mm and 60 mm in length. Thus, during a normal operation, a surgeon may be required to utilize several different stapling instruments to perform a single laparoscopic surgical procedure. Such practices increase the time, complexity and overall costs associated with laparoscopic surgical procedures. In addition, costs are greater in designing and manufacturing multiple stapler sizes, as opposed to creating a single, multipurpose stapler.

It would be extremely beneficial to provide a surgical device for use during laparoscopic and/or endoscopic surgical procedures that can be employed with several different sized disposable loading units to reduce the overall costs associated with such procedures. It would also be particularly beneficial if the device could perform multiple tasks, using disposable loading units of varying size and of varying purpose, such as, for example, to staple, clip and/or cut.

In making improvements or modifications to the current instruments, it would be highly desirable not to sacrifice any of the important benefits of the MULTIFIRE ENDO GIA* 30 and 60 instruments as compared to other commercially available products, e.g., the endoscopic stapling instruments manufactured and marketed by Ethicon, Inc. For example, any improvement should advantageously provide a fresh knife blade for each firing of the instrument and ensure that the disposable loading unit is securely retained in the stapling instrument unless and until the operating team chooses to remove it. These advantages have historically been found in the U.S. Surgical instruments, but not in the Ethicon instruments.

Therefore, a need exists for a reliable surgical staples and disposable loading units for use therewith that exhibit all of the benefits of the present assignee's commercially available instruments while also reducing the cost and complexity of manufacture.

SUMMARY

The subject application is primarily directed to a stapling device for applying parallel rows of surgical fasteners to body tissue and, preferably, one that concomitantly forms an incision between the rows of staples during an endoscopic or laparoscopic surgical procedure. A particularly unique feature of the stapling device described herein is that it can be employed with a number of different disposable loading units. Moreover, the stapling device of the subject application can be utilized with disposable loading units configured to apply linear rows of staples measuring from about 15 mm in length to about 60 mm in length.

In a preferred embodiment of the subject surgical stapler, the device includes a handle assembly including an elongated barrel portion and an actuation handle movable through an actuating stroke, and an elongated body extending distally from the barrel portion of the handle assembly and defining a longitudinal axis. An elongated actuation shaft is supported at least in part within the barrel portion of the handle assembly and it has a particular linear dimension. The actuation handle interacts with the actuation shaft such that manipulation of the actuation handle through a complete actuating stroke causes the actuation shaft to translate through a predetermined linear distance.

A disposable loading unit is operatively engaged in a distal portion of the elongated body. The disposable loading unit preferably includes a carrier, a staple cartridge containing a plurality of staples, an actuator (movable through the carrier and staple cartridge) and an anvil. The instrument actuation shaft drives the actuator through the staple cartridge to eject the staples against the anvil to form a staple line having a particular linear dimension. Preferably, the linear dimension of the staple line corresponds to the distance through which the actuation shaft translates in response to manipulation of the actuation handle through a particular number of complete or partial actuation strokes numbering more than one complete stroke.

The actuation shaft is preferably defined at least in part by a toothed rack having a particular rack length, and the actuation handle has a pawl member for selectively engaging the toothed rack and advancing the actuation shaft in response to manipulation of the actuation handle. When a disposable loading unit having linear rows of staples is used, the linear dimension of the staple line applied by the stapling unit is preferably proportional to the longitudinal travel of the actuation shaft. In a most preferred embodiment, the minimum linear dimension of the staple line will always be greater than the maximum linear distance through which the actuation shaft translates in response to one complete actuation stroke.

When a disposable loading unit having an anvil is used, the actuation handle is preferably movable through a clamping stroke in which the actuation shaft translates through a predetermined clamping distance to move the anvil from an open position to a closed position. The clamping stroke precedes the first of any number of complete or partial actuation strokes. In a preferred embodiment, an engagement hook is mounted within the barrel portion of the handle assembly to selectively maintain the actuation shaft in a particular position after traveling through the clamping distance and a notch is defined in a distal end portion of the actuation shaft, distal of the toothed rack, for receiving and releasably retaining the engagement hook.

In use of a preferred embodiment, movement of the actuation handle in a direction opposite the clamping stroke causes the engagement hook to release the actuation shaft, permitting the anvil to move to an open position. A lift finger is provided on a flange extending from the actuation handle and is positioned to move the engagement hook out of engagement with the notch when the actuation handle is moved in a direction opposite the clamping stroke. Preferably, a first biasing spring is provided within the handle assembly for biasing the actuation handle in a clockwise direction and a second biasing spring is provided within the handle assembly for biasing the actuation handle in a counter-clockwise direction, about a handle pivot point. The counter-clockwise direction corresponds to the direction of the clamping and actuating strokes.

The engagement hook is preferably configured to interact with the toothed rack to maintain the actuation shaft in a particular linear position during an actuation stroke, and it is normally biased into engagement with the actuation shaft. An abutment strut or beam is operatively associated with a proximal end portion of the stapler body for maintaining the engagement hook in a position out of engagement with the actuation shaft until a disposable loading unit is operatively engaged in a distal end portion of the elongated body. The abutment strut permits the engagement hook to engage the actuation shaft after a disposable loading unit has been operatively engaged in a distal end portion of the elongated instrument body.

In a preferred embodiment of the device described herein, the disposable loading unit is a adapted to apply linear rows of staples and includes: a carrier having a proximal end portion including a coupling for releasable engagement in a distal end portion of the elongated instrument body; an elongate staple cartridge supported in the carrier and containing a plurality of surgical fasteners and a plurality of fastener pushers for ejecting the fasteners from the staple cartridge; an actuator for contacting the fastener pushers; and an anvil supported on the carrier and mounted for movement with respect to the staple cartridge between an open position and a closed position. The anvil preferably has a fastener forming surface against which the surgical fasteners are driven when ejected from the staple cartridge by the fastener pushers, and a camming surface opposite the fastener forming surface. The actuator is preferably a wedged actuator that translates through the staple cartridge to sequentially interact with the fastener pushers to eject the fasteners from the staple cartridge.

The disposable loading unit further preferably includes an elongated drive beam having a proximal engagement portion, a distal working end portion having an abutment surface and a camming member. The proximal engagement portion is configured to mate with a distal end portion of the actuation assembly of the stapler while the abutment surface engages the actuator to eject staples from the staple cartridge during firing. The camming member contacts the camming surface of the anvil during firing. In use, the stapler actuation assembly moves the drive beam through the carrier causing the camming member to close the anvil as it substantially simultaneously causes the actuator to translate through the staple cartridge, thereby sequentially interacting with the plurality of fastener pushers to fire the staples.

Preferably, the camming member is defined by a cylindrical cam roller mounted on a flange extending from the distal working end portion of the drive beam. A longitudinal slot is defined in the anvil to accommodate the linear translation of the working end portion of the drive beam, and a transverse support flange is operatively mounted on the working end portion opposite the cam roller to engage an undersurface of the carrier as the cam roller engages the camming surface of the anvil. A longitudinal slot is also defined in the undersurface of the carrier to accommodate the linear translation of the working end portion of the drive beam. An optional anvil cover can be provided to ensure tissue is not inadvertently contacted by the drive beam or cam roller during firing.

Preferably, a knife blade is operatively supported adjacent a leading edge of the working end portion of the drive beam for forming an incision in stapled body tissue. Also, the actuator is preferably a sled including a planar base portion and a plurality of spaced apart upstanding cam wedges each having an inclined leading edge for interacting with the fastener pushers within the staple cartridge.

In a preferred embodiment of the stapling device described herein, the distal end portion of the elongated body and the proximal portion of the carrier includes cooperating portions of a bayonet-type coupling. The coupling facilitates the convenient removal and engagement of a variety of different sized disposable loading units including those which are configured to apply staple rows that are approximately 30 mm in length, 45 mm in length, and 60mm in length. Accordingly, it is envisioned that the device can be sold and marketed as a kit which would include at least one surgical instrument designed to actuate compatible disposable loading units and a plurality of disposable loading units that can vary in size and type. The disposable loading units can be adapted to apply linear rows of staples, clips or other forms of fasteners. A common feature of these disposable loading units is that they utilize the longitudinal motion of the instrument actuation control rod to apply the fasteners.

These and other features of the surgical stapling device of the subject application will become more readily apparent to those skilled in the art from the following detailed description of the preferred embodiments of the device taken in conjunction with the drawings.

BRIEF DESCRIPTION OF THE DRAWINGS

Various embodiments of the surgical stapling apparatus of the subject application will be described hereinbelow with reference to the drawings wherein:

FIG. 12 is a side elevational view of the disposable loading unit of the subject application with the body thereof sectioned to illustrate the relative positions of the components prior to closing the anvil to clamp a tubular vessel;

FIG. 13 is a side elevational view of the disposable loading unit of the subject application with the body thereof sectioned to illustrate the relative positions of the components after the apparatus has been completely fired;

FIG. 15 illustrates an alternate embodiment of a disposable loading unit adapted to apply surgical clips; and FIG. 16 illustrates an alternate embodiment of a disposable loading unit adapted to apply single surgical staples.

DETAILED DESCRIPTION OF PREFERRED EMBODIMENTS

Figure 1:
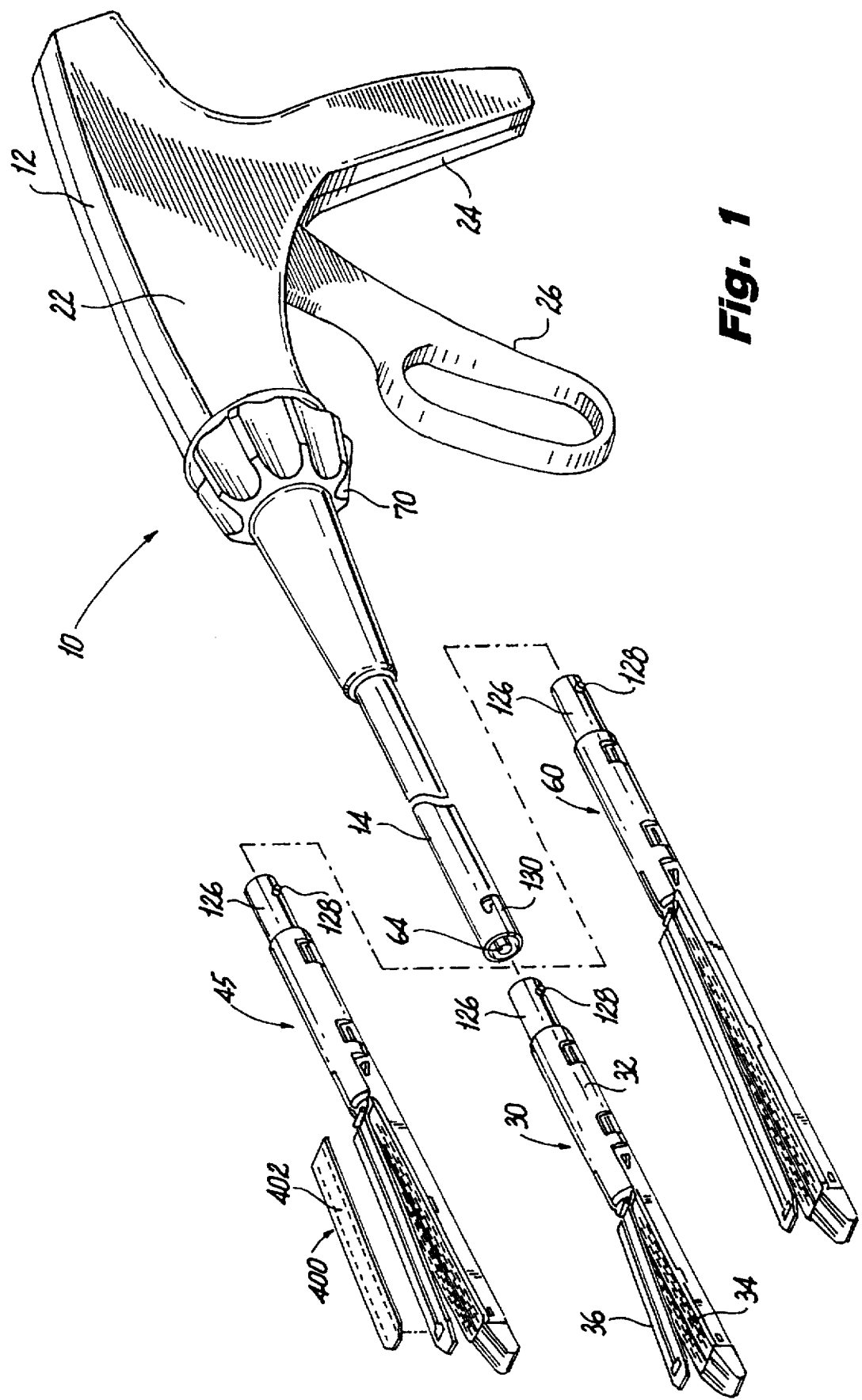
FIG. 1 is a perspective view of a surgical stapling apparatus constructed in accordance with a preferred embodiment of the subject application in conjunction with three different sized disposable loading units each configured for utilization with the stapling apparatus.

In the drawings and in the description which follows, the term "proximal", as is traditional, will refer to the end of the stapling apparatus which is closest to the operator, while the term "distal" will refer to the end of the apparatus which is furthest from the operator.

Referring now to the drawings wherein like reference numerals identify similar structural elements of the subject invention, there is illustrated in FIG. 1 a surgical apparatus constructed in accordance with a preferred embodiment of the subject application and designated generally by reference numeral 10. In brief, surgical apparatus 10 is a surgical stapling apparatus configured to engage body tissue, apply a plurality of surgical fasteners thereto, and form an incision in the fastened body tissue during a laparoscopic surgical procedure. Apparatus 10 can also be used to apply surgical clips and other fasteners (discussed in greater detail below) but will be primarily discussed in the context of applying parallel rows of staples from a staple cartridge disposed in a disposable loading unit.

Surgical apparatus 10 is unique among laparoscopic devices known in the art because it can employ a plurality of different sized disposable loading units. Moreover, apparatus 10 is preferably configured to operate with individual disposable loading units that apply linear rows of staples measuring 30 mm, 45 mm, or 60 mm in length (FIG. 1) or apply other types of fasteners (FIGS. 15 and 16). Thus, during a laparoscopic surgical procedure, a single instrument can be utilized with a plurality of interchangeable disposable loading units to perform several tasks. The preferred embodiments discussed in detail primarily relate to disposable loading units adapted to apply linear rows of staples.

As illustrated in FIG. 1, surgical apparatus 10, has a handle assembly 12 and an elongated body 14. Apparatus 10 is adapted for use with disposable loading units 30, 45 and 60 each of which has a carrier 32, a staple cartridge 34, and an anvil 36 against which staples are driven when ejected from the housing. The following specification will provide a detailed description of the construction and operation of the apparatus and disposable loading units for use therewith.

Figure 2:
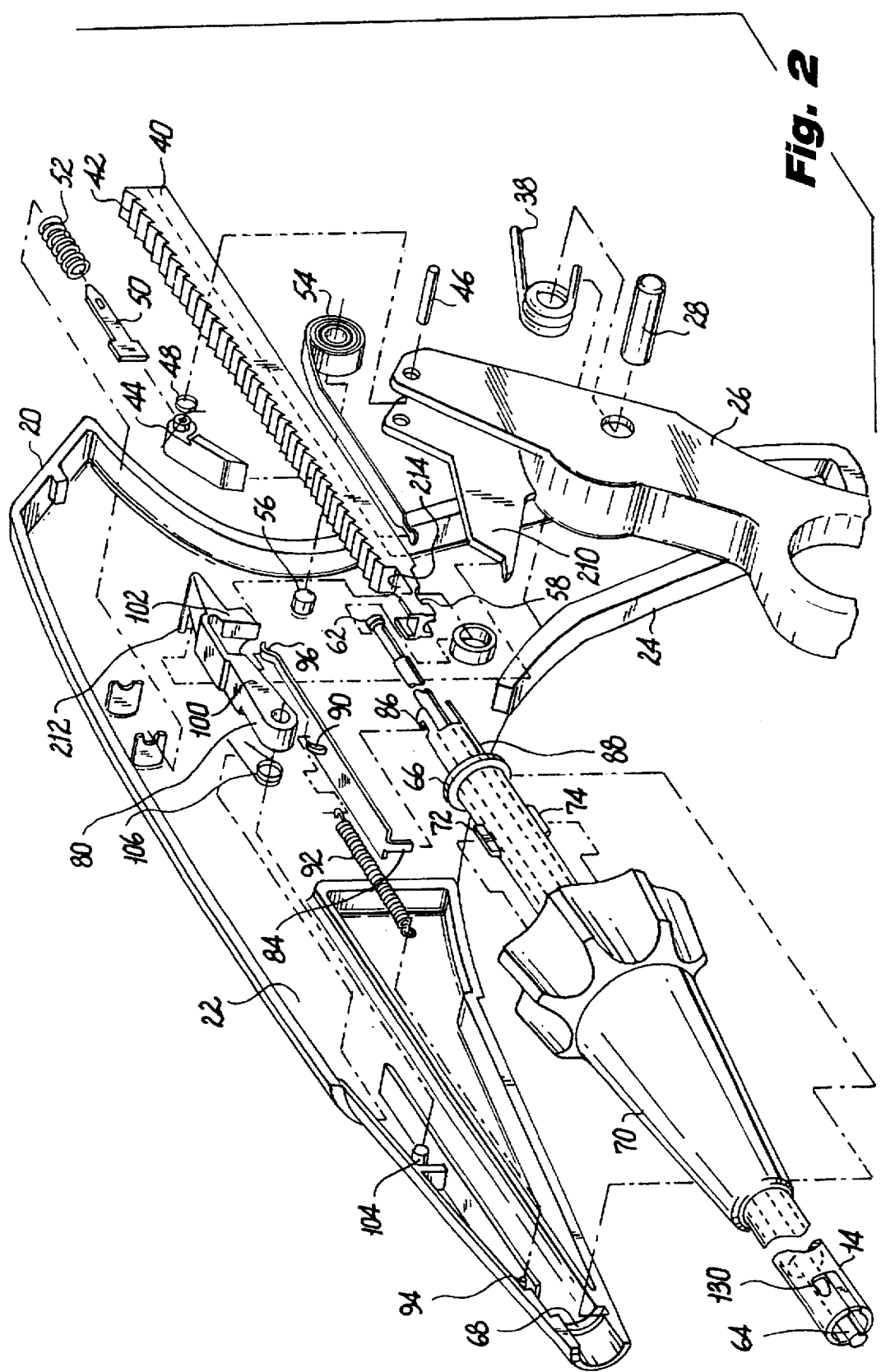
FIG. 2 is an exploded perspective view of the handle assembly of the surgical stapling apparatus illustrated in FIG. 1.

Referring to FIG. 2, handle assembly 12 includes a housing 20 defined by an elongated barrel portion 22, a stationary handle 24 depending from the barrel portion, and an actuation handle 26 which is pivotably mounted to the barrel portion and movable with respect to the stationary handle. Actuation handle 26 is supported within housing 20 by a pivot pin 28 and is biased against counter-clockwise movement by a coiled torsion spring 38.

Actuation handle 26 controls the linear movement of actuation shaft 40 which is mounted within barrel portion 22. More particularly, actuation shaft 40 has a toothed rack 42 defined thereon, and actuation handle 26 has a ratcheting pawl 44 mounted thereto for incrementally engaging and advancing actuation shaft 40. Pawl 44 is mounted on a pivot pin 46 and a coiled torsion spring 48 biases the pawl into engagement with toothed rack 42. A linear biasing strut 50 is supported within barrel portion 22 and is biased distally by a coiled compression spring 52 to bias the pawl, and hence the actuation handle, against clockwise rotation about pivot pin 28. Biasing strut 50 also serves to act on an angled rear cam surface on pawl 44 wherein contact of the cam surface with strut 50 causes pawl 44 to rotate clockwise (away from rack 42). When the instrument is at rest, pawl 44 is biased away from toothed rack 42. When actuation handle 26 is pulled proximally, pawl 44 moves away from strut 50 and rotates counterclockwise and engages the teeth of actuation shaft 40, thereby allowing actuation handle 26 to drive the shaft distally.

Actuation shaft 40 is normally biased in a proximal direction within barrel portion 22 by a constant force spring 54 which is mounted to the actuation shaft adjacent the distal end thereof by conventional fastening means known in the art. Constant force spring 54 is supported on a boss 56 provided within the housing 22 of handle assembly 12. The distal end portion of actuation shaft 40 has a cavity 58 defined in an undersurface thereof for engaging and retaining the flanged proximal end 62 of control rod 64. Control rod 64 extends coaxially through the elongated body 14 of surgical stapler 10 to interact with a disposable loading unit at a distal end thereof. Thus, linear advancement of actuation shaft 40 in response to manipulation of actuation handle 26 causes corresponding longitudinal movement of control rod 64, and, as will be discussed in detail hereinbelow, actuation of an associated disposable loading unit.

With continuing reference to FIG. 2, the proximal end portion of the elongated body 14 of surgical stapler 10 has an annular flange 66 formed thereon which engages a corresponding annular recess 68 formed within the barrel portion 22 adjacent the distal end thereof to fixedly attach the two structural members. The engagement of flange 66 within recess 68 facilitates rotational movement of body portion 14 with respect to the barrel portion 22 about a longitudinal axis which extends therethrough. A collar 70 is fixedly mounted to the proximal portion of stapler body 14 by a pair of opposed protuberances 72 and 74. Thus, rotation of collar 70 will cause corresponding rotation of body portion 14 to increase the range of operability of surgical stapler 10.

Within handle assembly 12, there is also contained a mechanism for initiating the engagement between a rack lock 80 and the toothed rack 42 of actuation shaft 40. Rack lock 80 maintains the longitudinal position of actuation shaft 40 under the bias of constant force spring 54. Rack lock 80 will not engage the rack unless and until a disposable loading unit is operatively engaged in the distal end portion of portion body 14. This mechanism is illustrated in FIG. 2 and its interaction with rack lock 80 is best understood by also referring to FIGS. 4 and 5. The mechanism, includes an elongate beam or strut 82 having a distal tang 84 that engages a keeper notch 86 formed adjacent the proximal end of a support tube 88 that is slidably mounted within stapler body 14. Beam 82 has a medial hook 90 for engaging the proximal end of a coiled biasing spring 92, the distal end of which is mounted on a boss 94 provided within barrel portion 22. Biasing spring 92 biases beam 82, and hence support tube 88, against proximal movement. An arcuate cam finger 96 projects proximally from beam 82 for interacting with an angled cam surface 98 defined on the undersurface of the body 100 of rack lock 80. Rack lock 80 further includes a wedged clasp portion 102 which is dimensioned and configured to engage the teeth of the toothed rack 42 to maintain the longitudinal position of actuation shaft 40 during the operation of instrument 10. The body 100 of rack lock 80 is mounted on a boss 104 provided within the barrel portion 22 of housing 20. A coiled torsion spring 106 is also mounted on boss 104 and is connected to body 100 to bias the rack lock into engagement with toothed rack 42.

Figure 4:
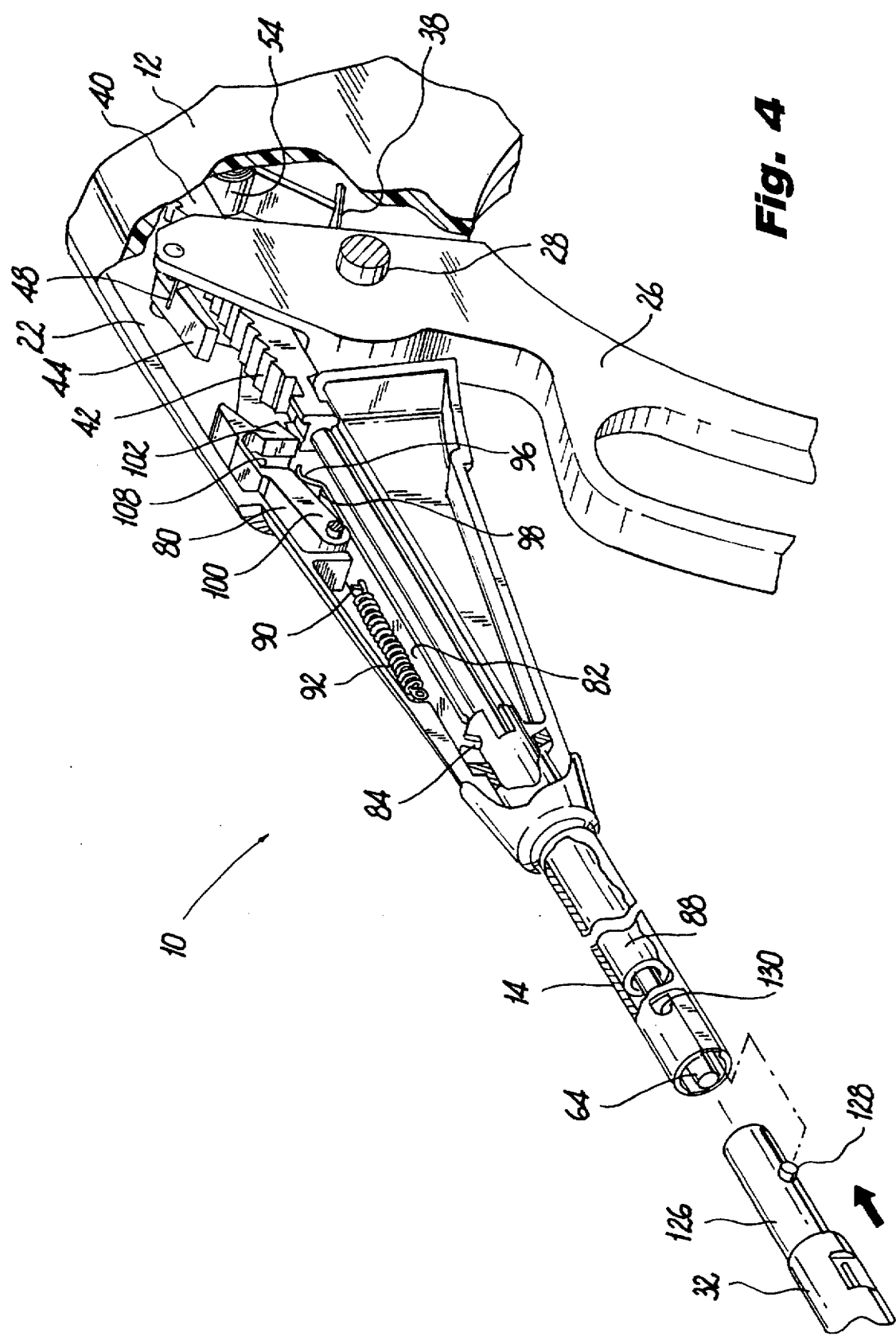
FIG. 4 is a perspective view in partial cross-section of the handle assembly and body portion of the stapling apparatus illustrated in FIG. 1 as the disposable loading unit of FIG. 3 is inserted into the distal end of the body.
Figure 5:
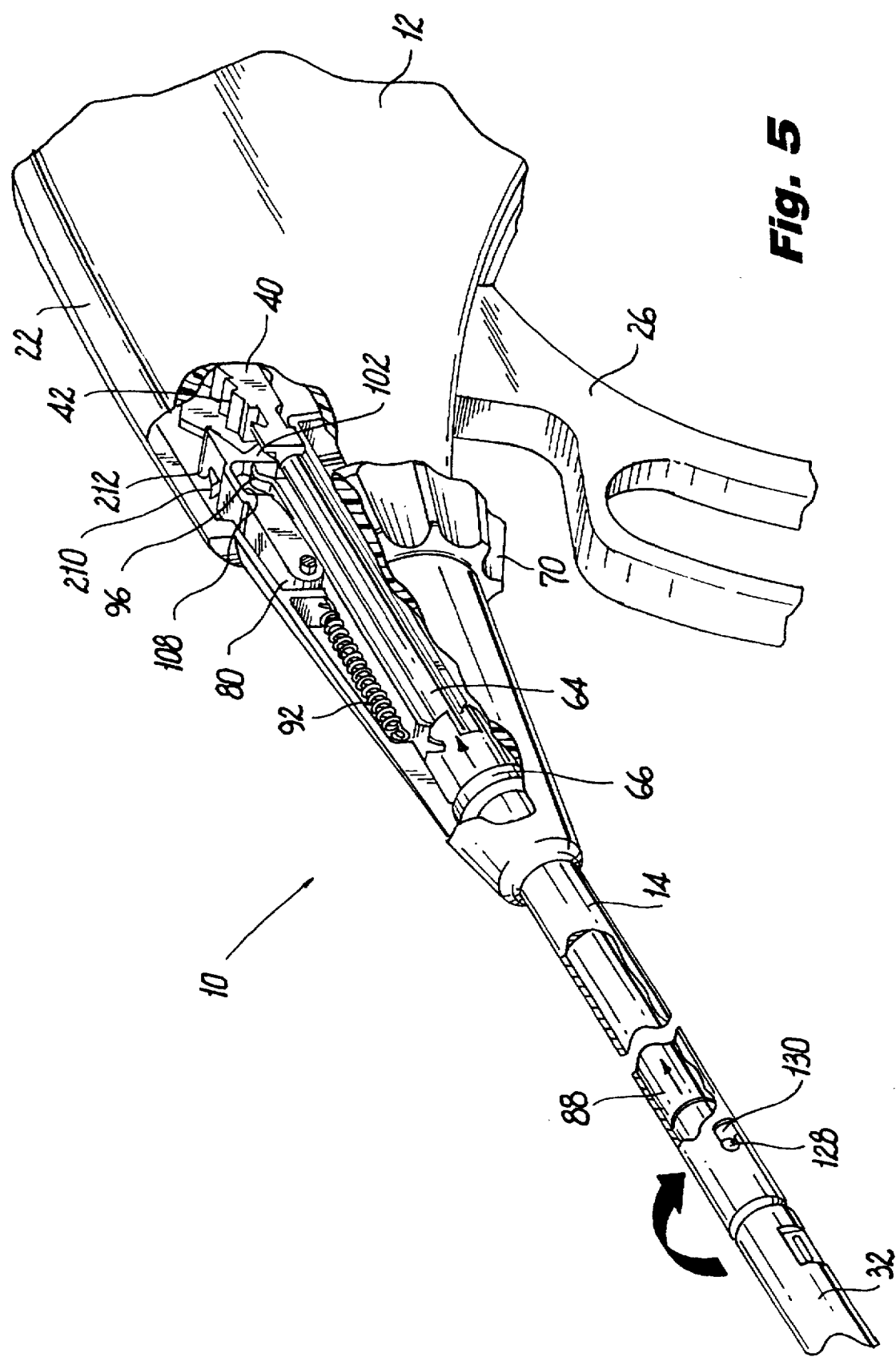
FIG. 5 is a perspective view which corresponds to the illustration in FIG. 4 with the disposable loading unit mounted in the body of the stapling apparatus and the actuation mechanism within the handle portion enabled as a result of the insertion of the disposable loading unit.

As best seen in FIGS. 4 and 5, when the proximal end portion of the carrier 32 of disposable loading unit 30 is inserted into the distal end of elongated body 14, support tube 88 is urged in a proximal direction against the bias of spring 92. Thereupon, beam 82 translates proximally and the arcuate cam finger 96 contacts angled cammed surface 98, lifting rack lock 80 and causing it to rotate in a counter-clockwise direction against the bias of torsion spring 106. At such a time, the cam finger 96 of beam 82 is accommodated within a recess 108 formed in the body 100 of rack lock 80. With the rack lock in this position, it will engage actuation shaft 40 when it is advanced distally upon manipulation of actuation handle 26. The interaction of rack lock 80 and actuation shaft 40 will be discussed in greater detail hereinbelow with respect to the manner in which instrument 10 is operated to clamp body tissue and apply fasteners thereto.

Figure 3:
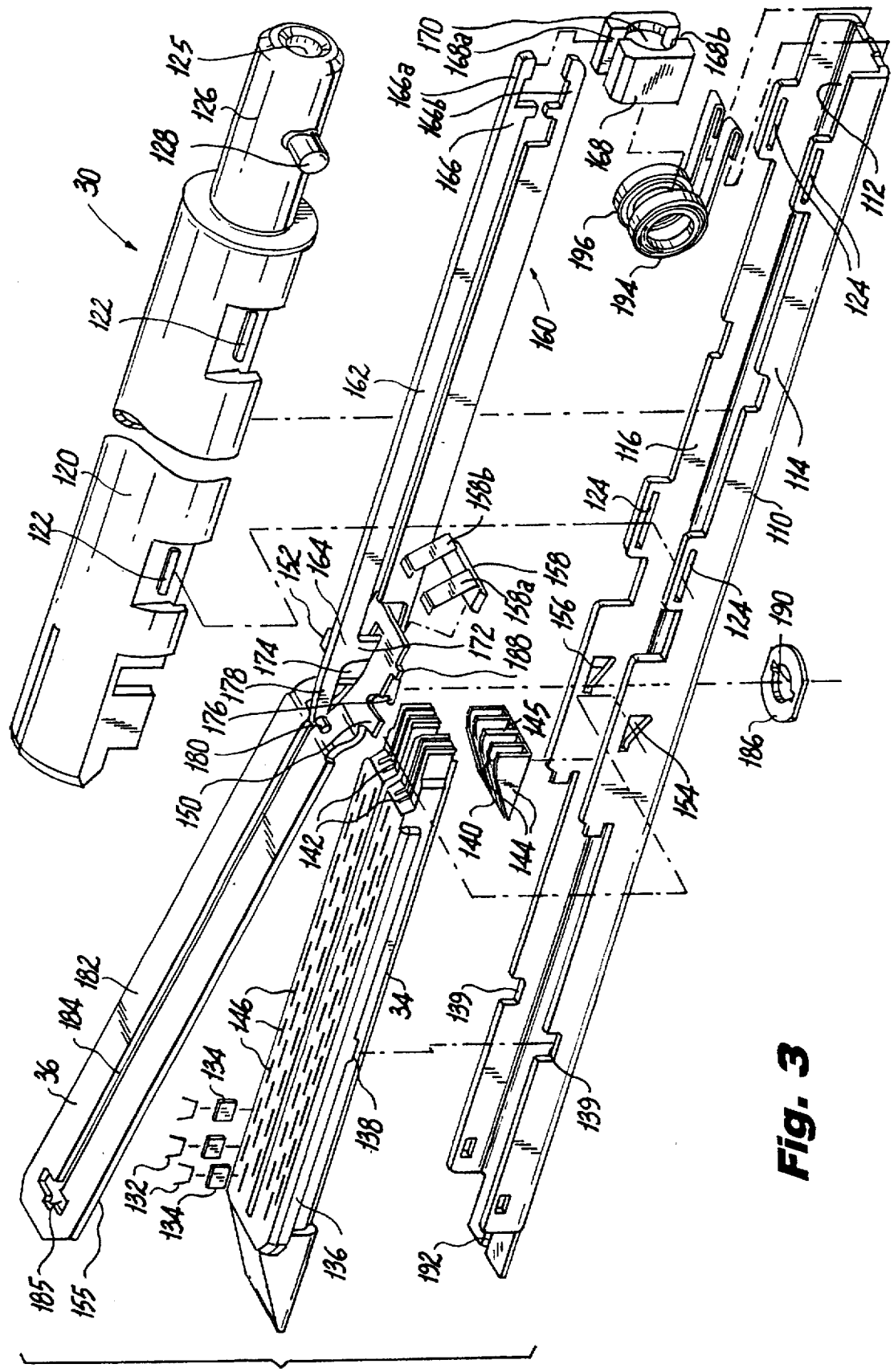
FIG. 3 is an exploded perspective view of a disposable loading unit constructed in accordance with a preferred embodiment of the subject application.

Referring now to FIG. 3, an exemplary disposable loading unit is illustrated and is designated generally by reference numeral 30. As noted hereinabove, disposable loading unit 30, which is particularly adapted to apply a plurality of linear rows of staples measuring about 30 mm in length, is one of several different size or type of disposable loading units that can be utilized with instrument 10 during a surgical procedure. The carrier 32 of stapling unit 30 includes an elongate channel 110 having a base 112 and two parallel upstanding walls 114 and 116 which include several mounting structures for supporting staple cartridge 34 and anvil 36. Carrier 32 also includes mounting portion 120 which is mounted to the proximal portion of channel 110 through the engagement of a plurality of spaced apart rectangular tangs 122 and a plurality of corresponding slots 124 formed in the opposed walls 114 and 116 of channel 110. The proximal end section 126 of mounting portion 120 is dimensioned and configured for insertion into the distal end portion of elongated body 14, and it is provided with an axial bore 125 for accommodating the distal end of control rod 64.

A coupling stem 128 projects radially outwardly from end section 126 for interacting with the J-shaped coupling slot 130 defined in the wall of the distal end portion of elongated body 14 (see FIGS. 4 and 5). Stem 128 and slot 130 together define a conventional bayonet-type coupling which facilitates quick and easy engagement and removal of the stapling unit from the stapler during a surgical procedure. Once engaged in the distal end portion of stapler elongated body 14, the distal end of support tube 88 urges proximal end section 126 distally under the bias of coiled spring 92, thereby maintaining the coupling stem 128 within coupling slot 130.

With continuing reference to FIG. 3, the distal portion of channel 110 supports staple cartridge 34 which contains a plurality of surgical fasteners 132 and a plurality of corresponding ejectors or pushers 134 that drive the fasteners from cartridge 34 under the influence of a fastener driving force exerted by actuation sled 140. Staple cartridge 34 is maintained within channel 110 by lateral struts 136 which frictionally engage the upper surfaces of channel walls 114 and 116, and the frictional engagement of housing tabs, such as tab 138, within notches 139. These structures serve to restrict lateral, longitudinal, and elevational movement of the staple cartridge 34 within channel 110.

Figure 14:
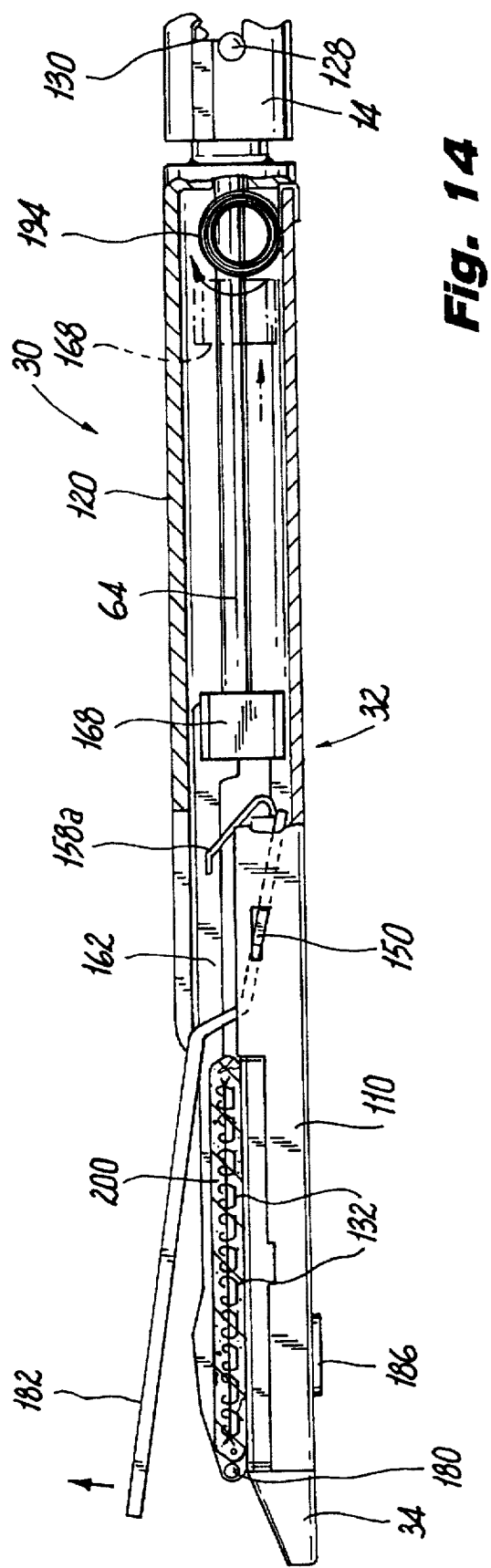
FIG. 14 is a side elevational view of the disposable loading unit as illustrated in FIG. 13 with the anvil moved to an open position under the bias of a release spring.
Figure 17:
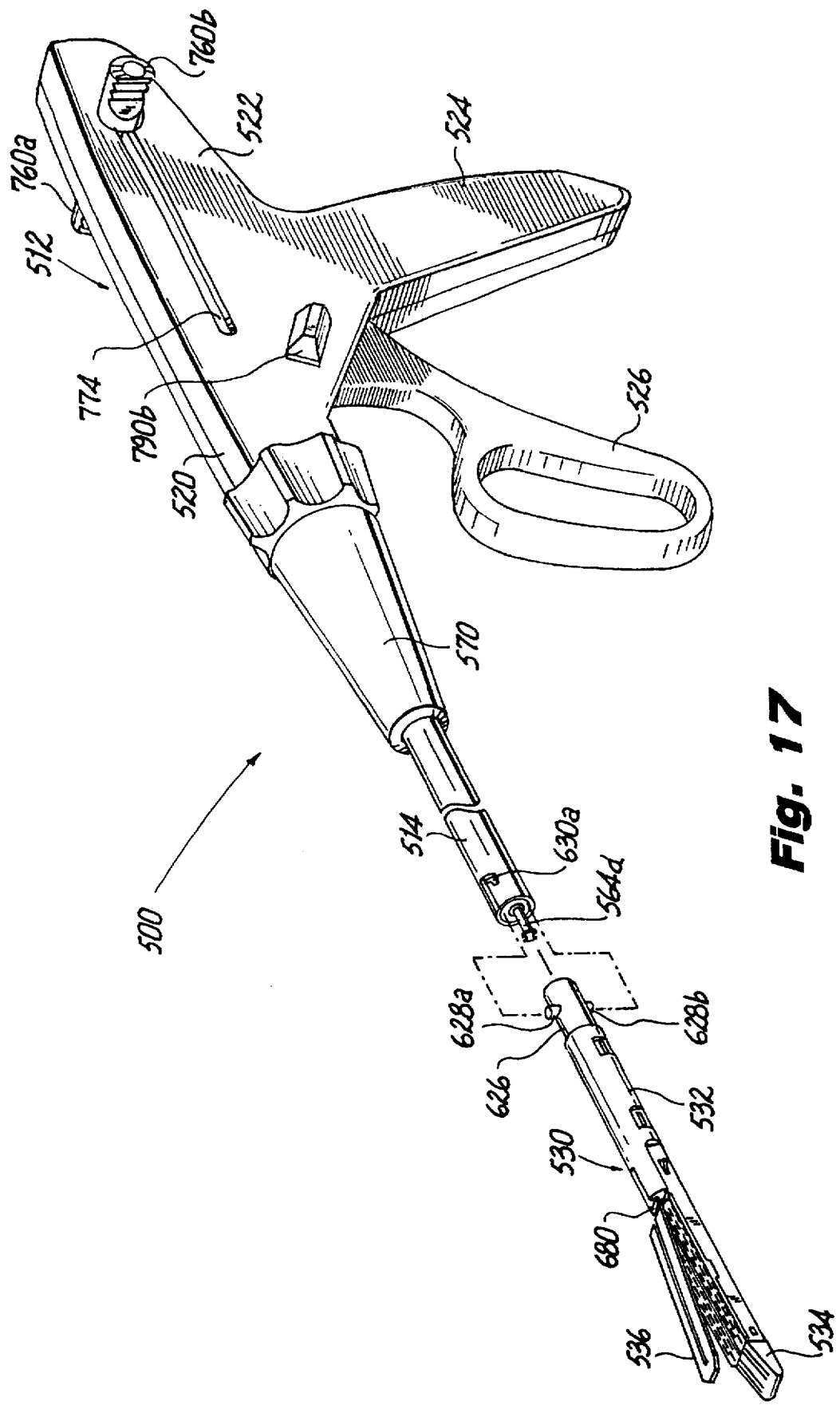
Figure 18:
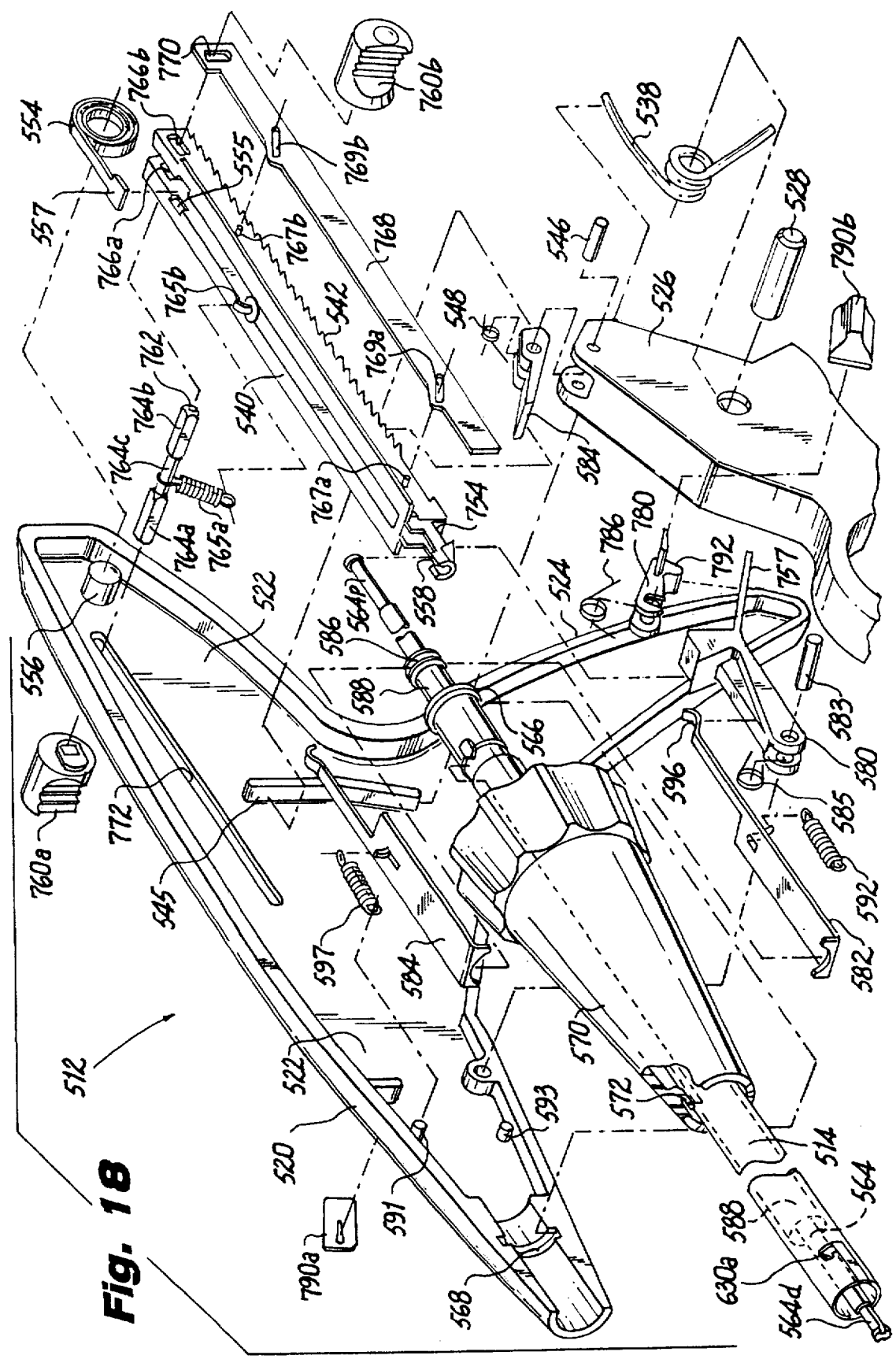
Figure 22:
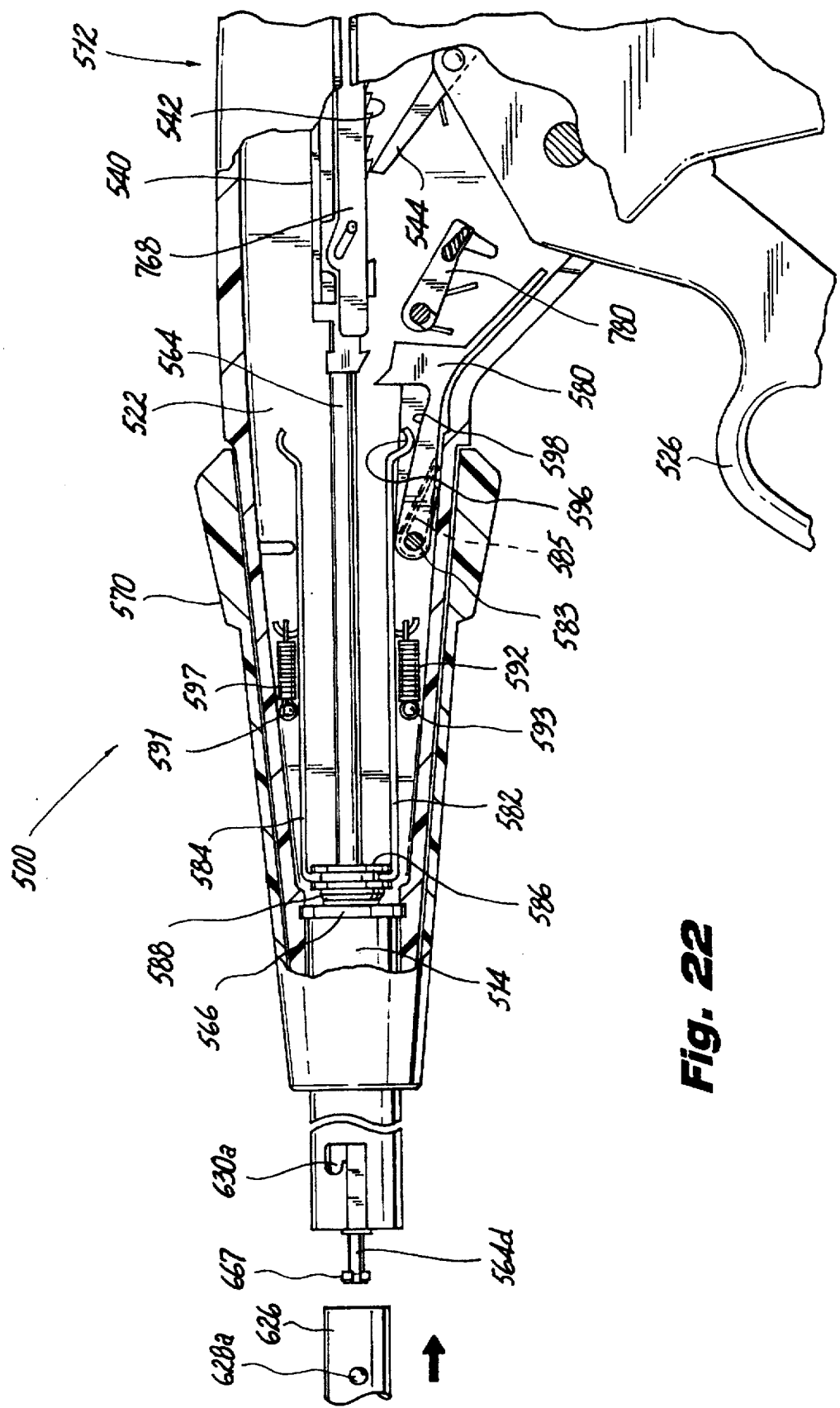
Figure 23:
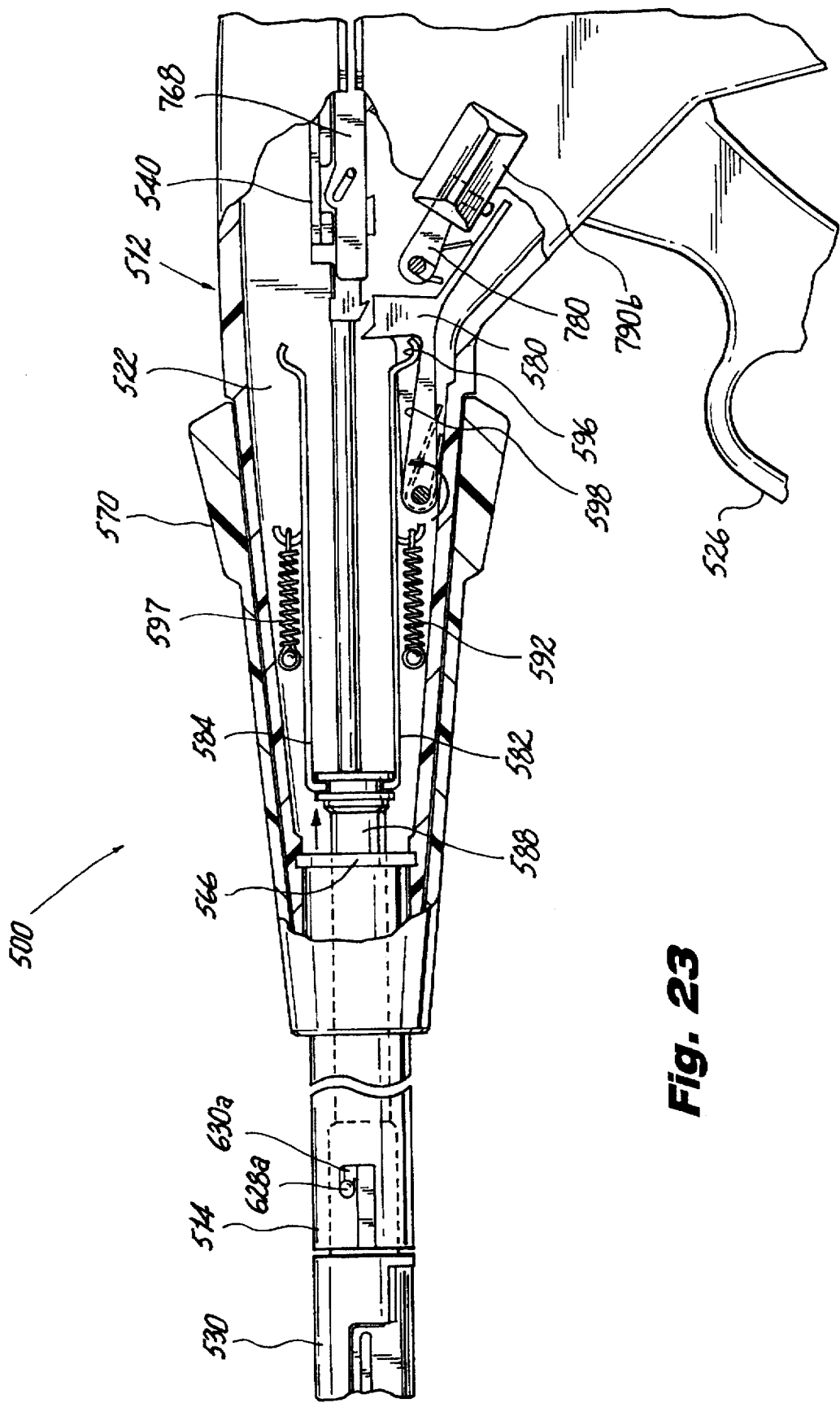
Figure 24:
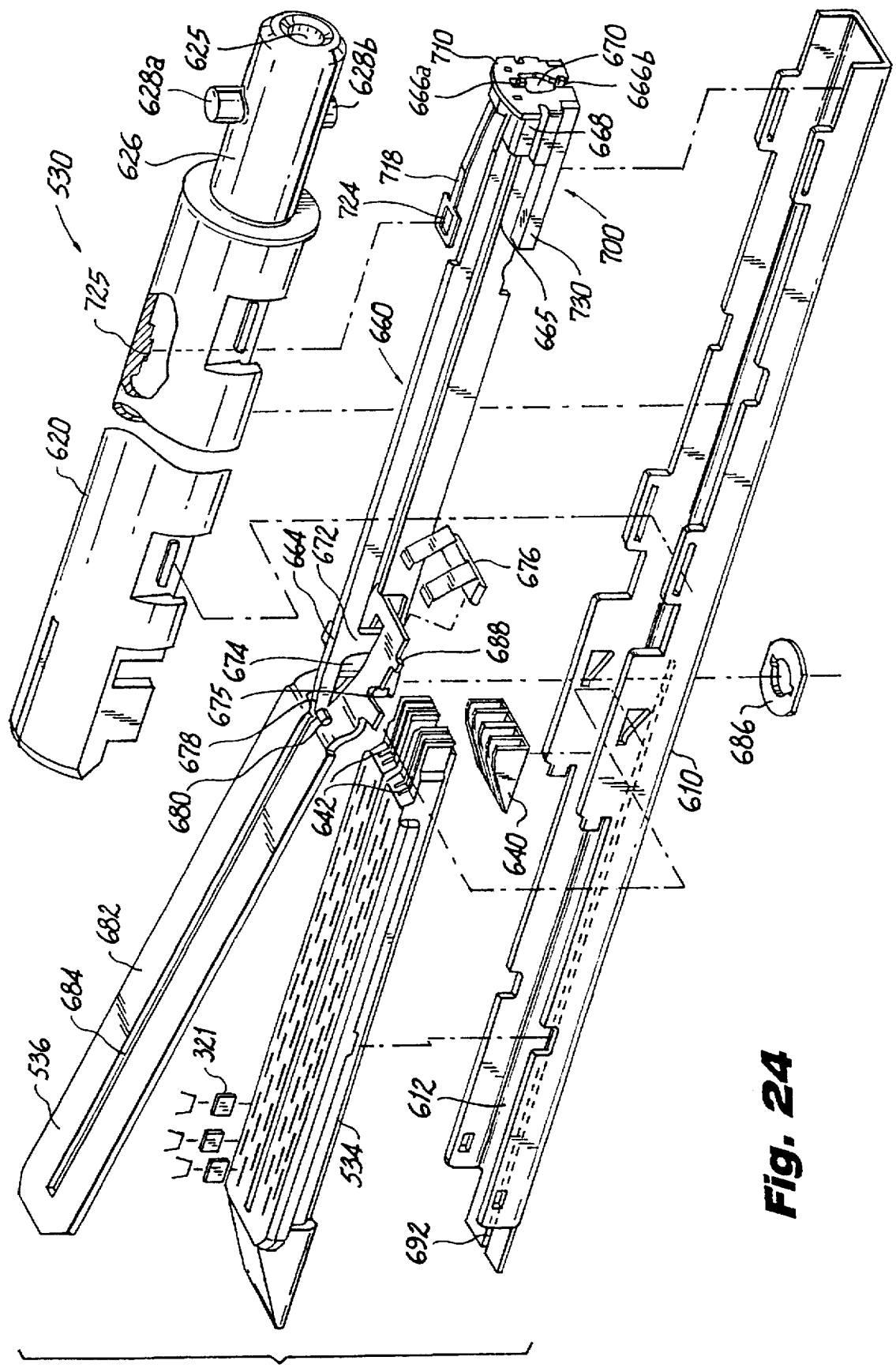
Figure 31:
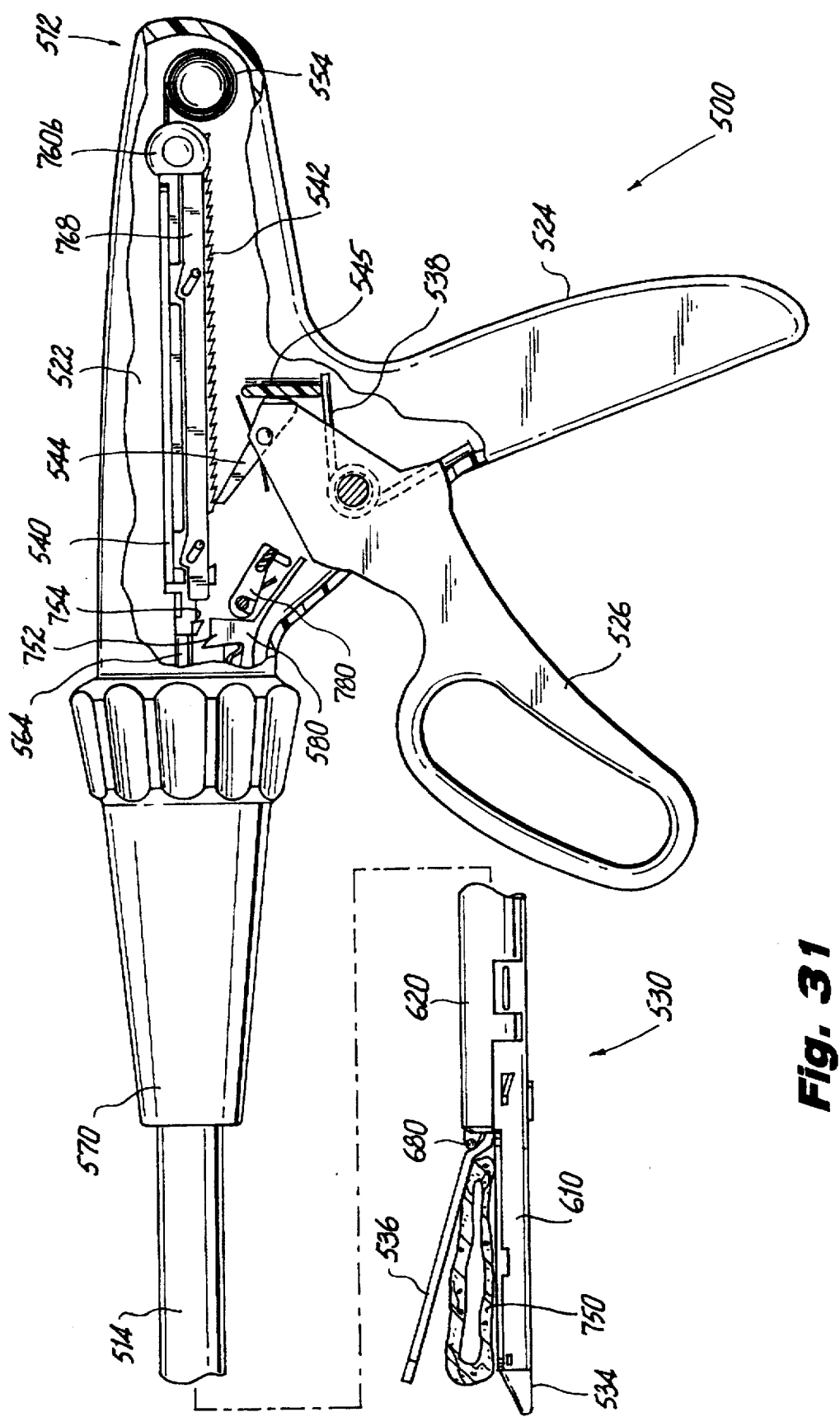
Figure 32:
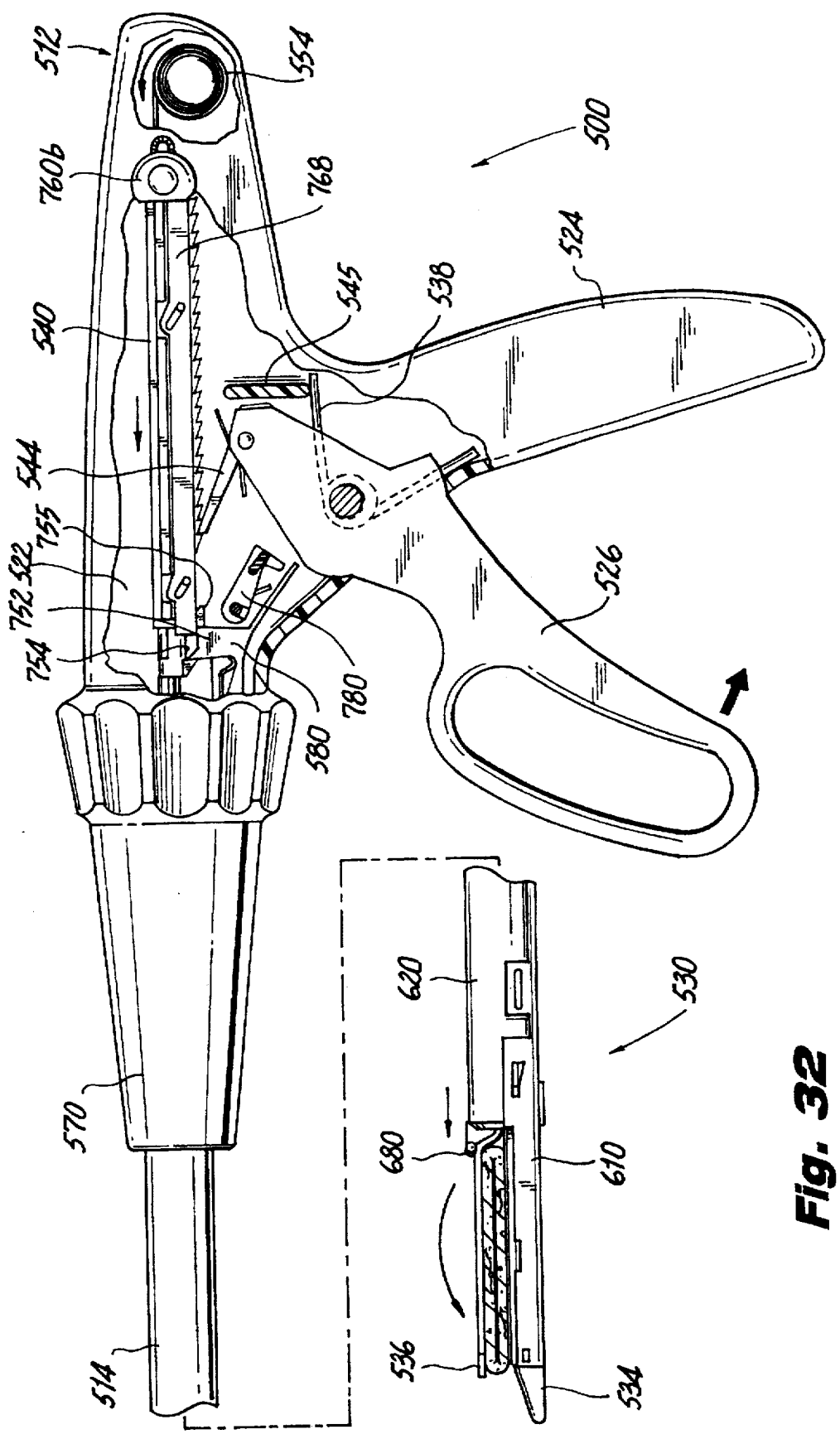
Figure 33:
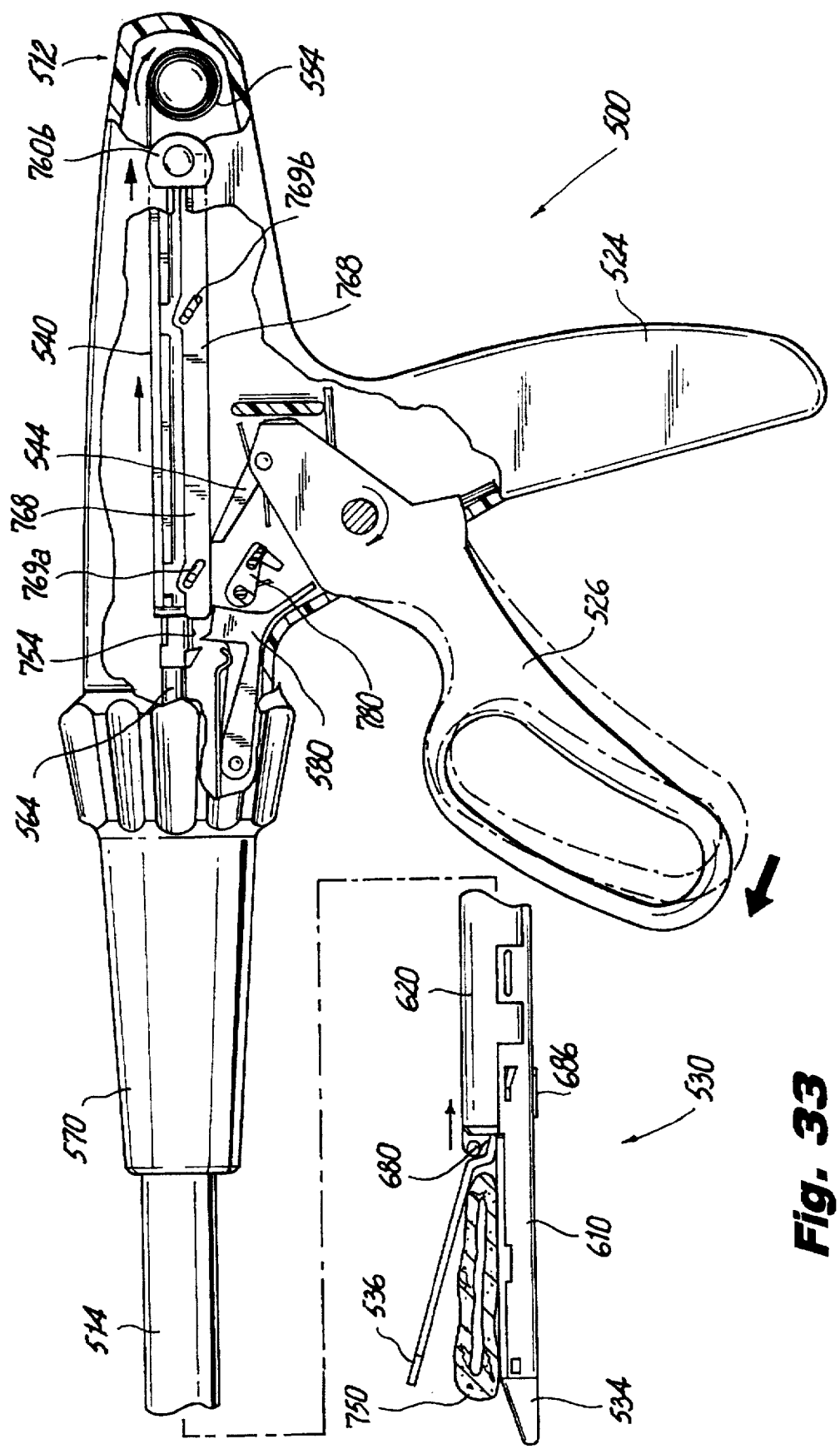
Figure 34:
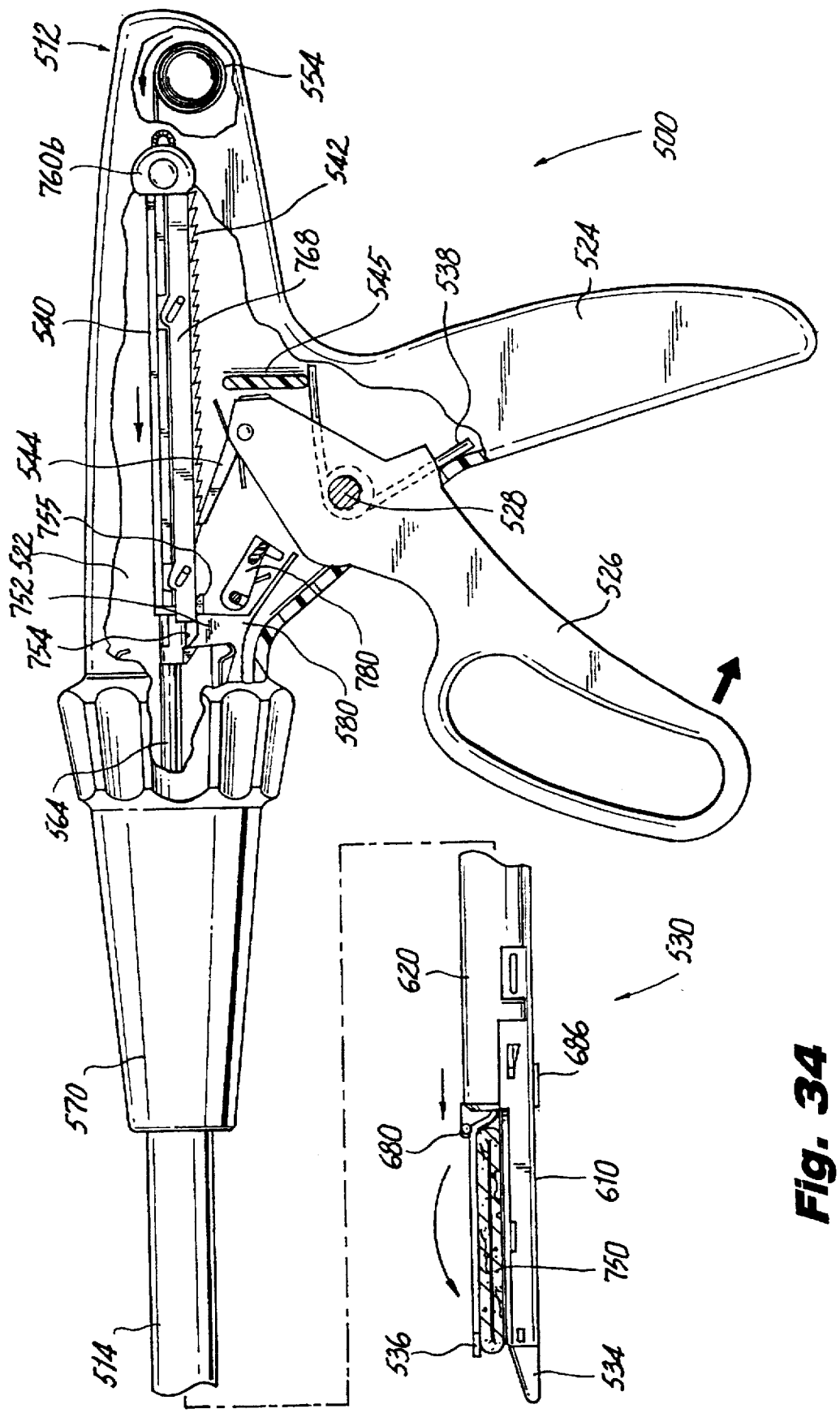
Figure 35:
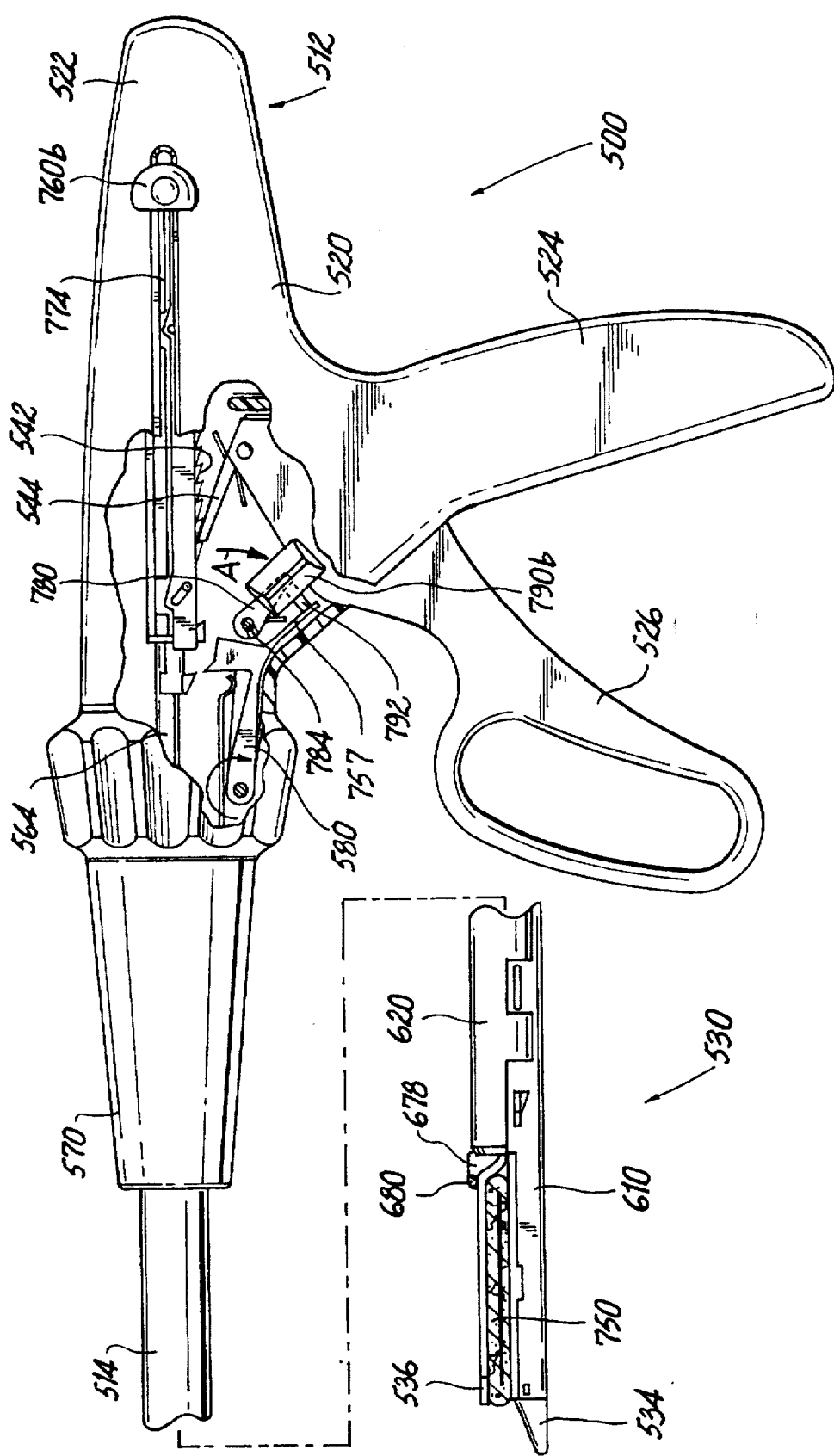
Figure 36:
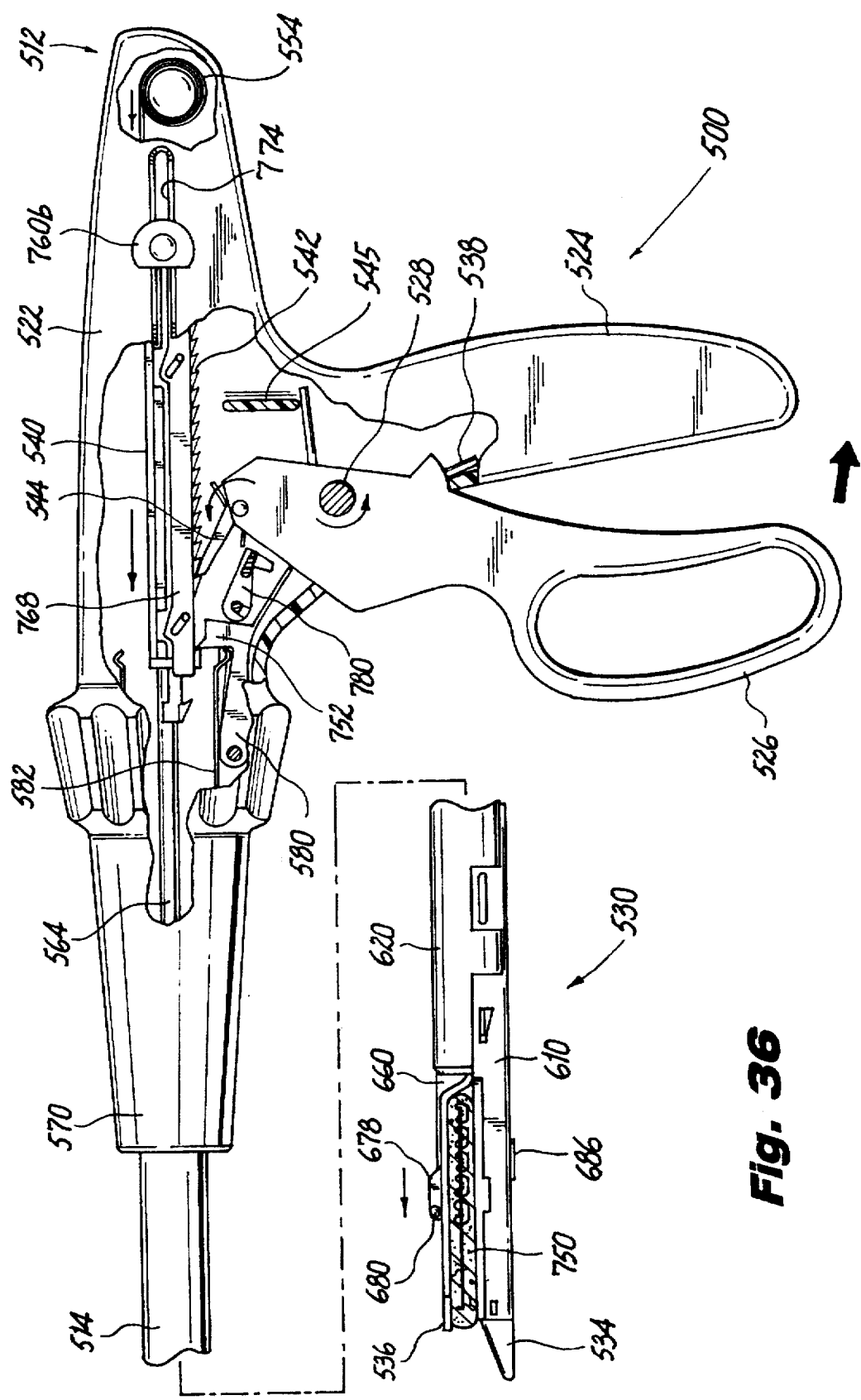
Figure 37:
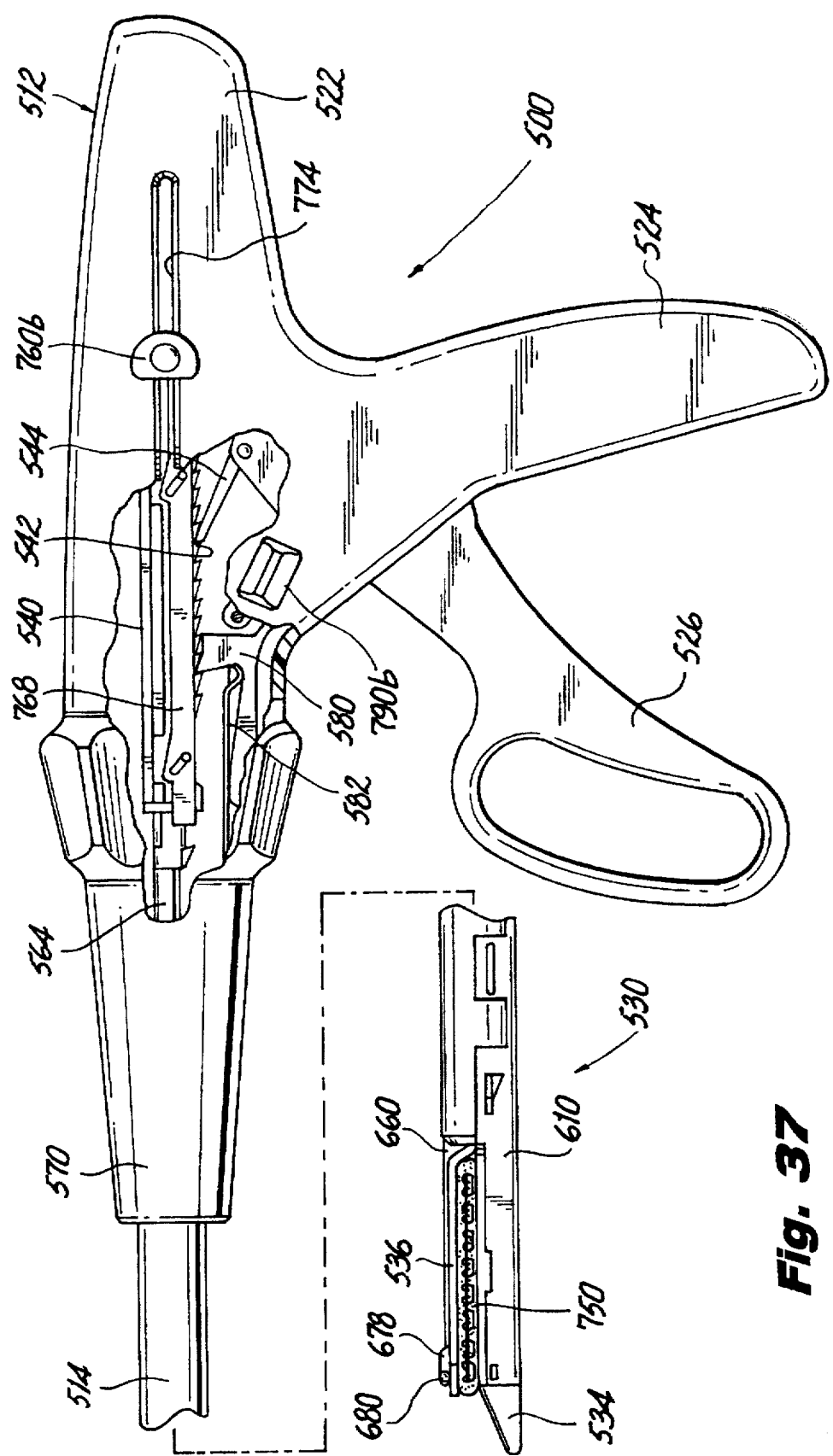
Figure 38:
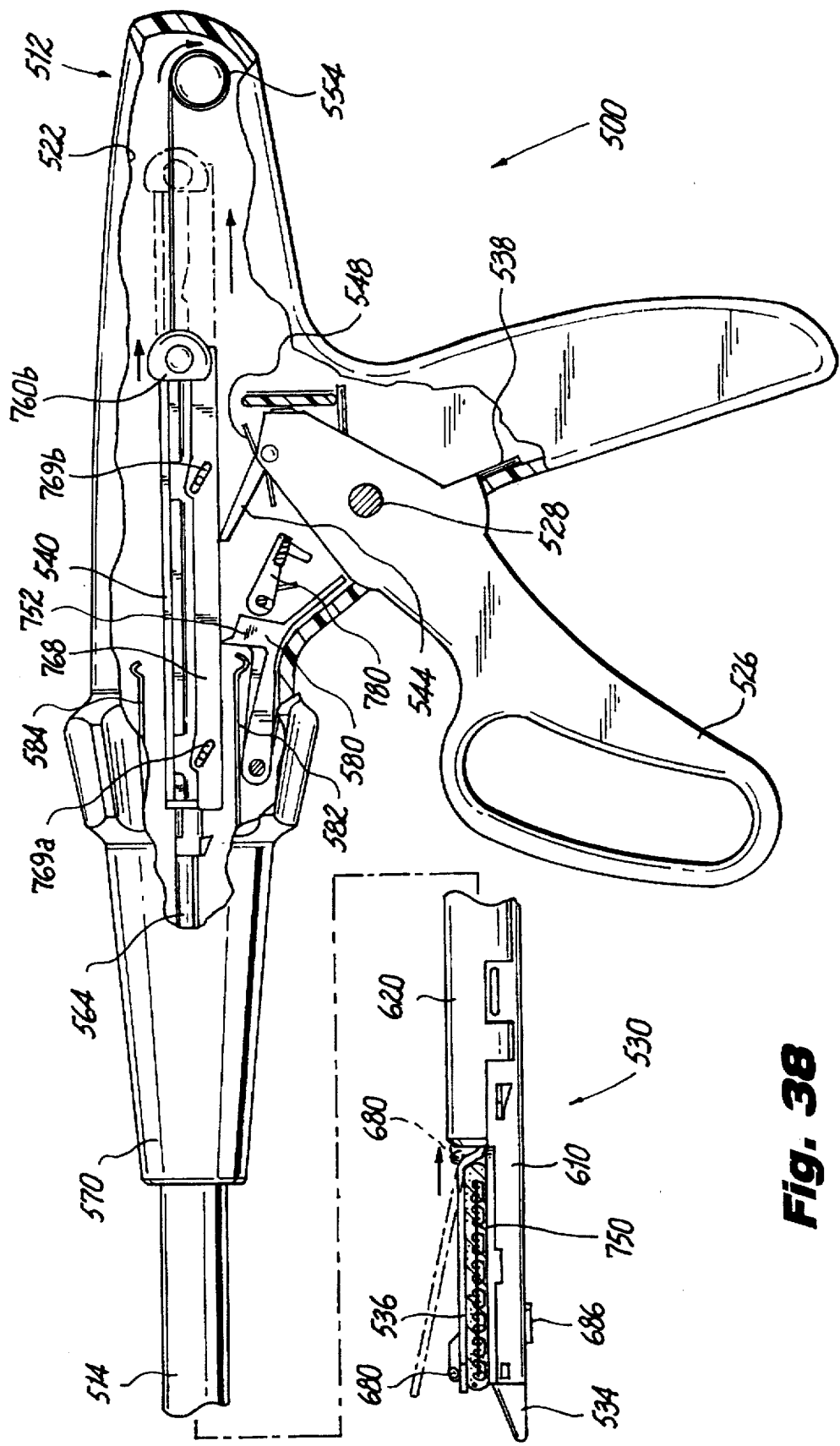
Figure 41:
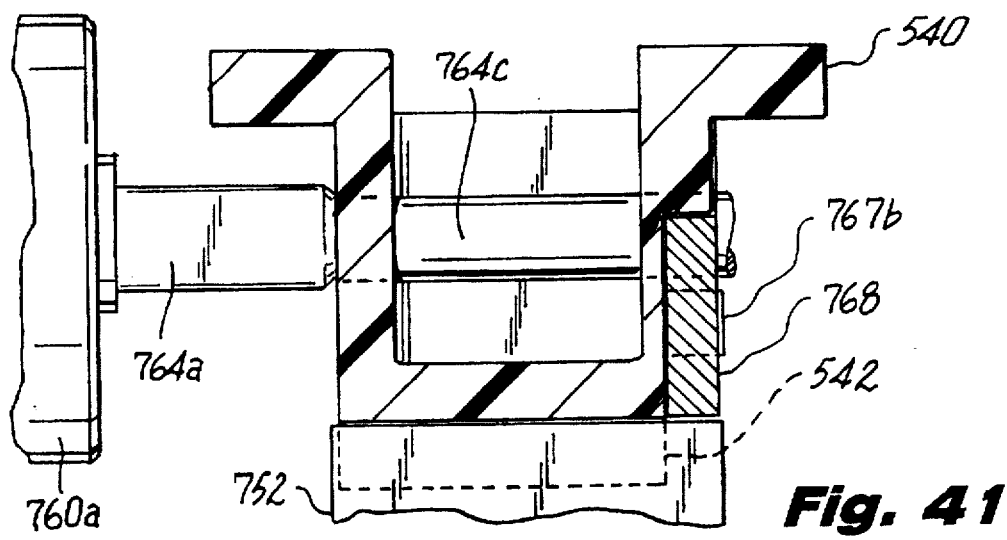
Figure 42:
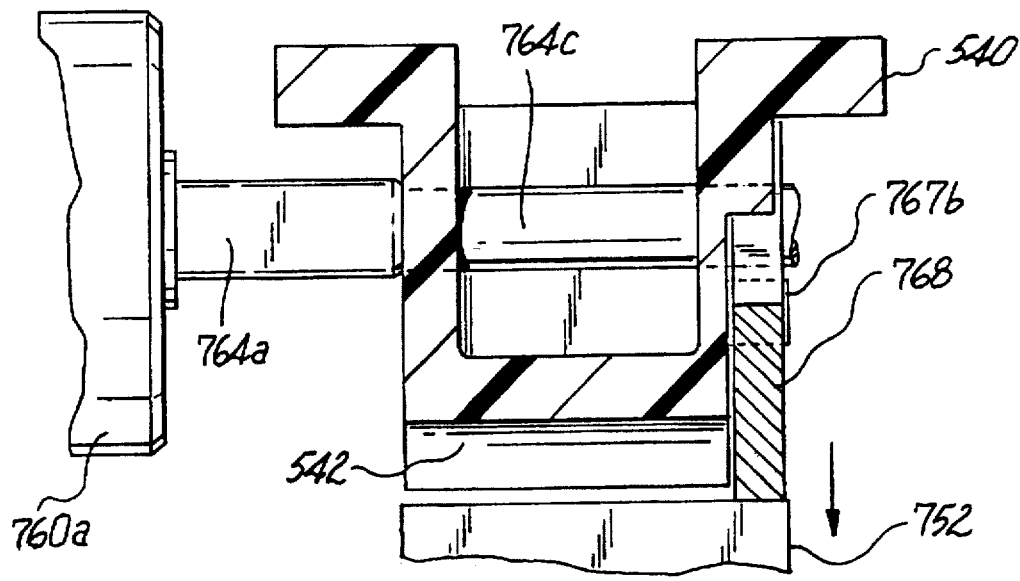
Figure 43:
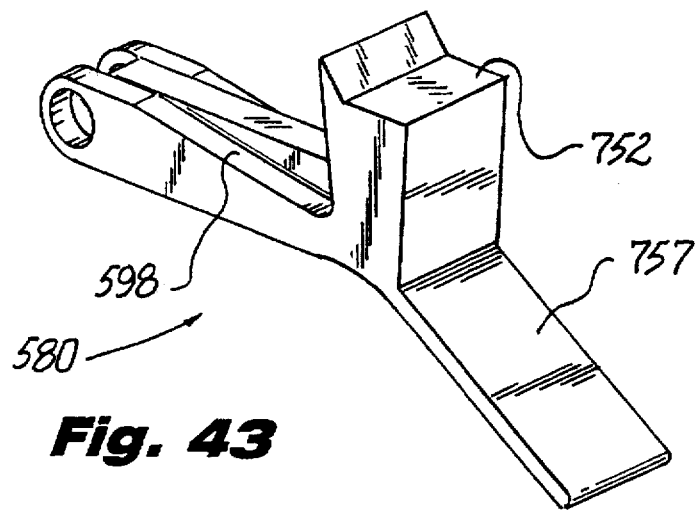
Figure 44:
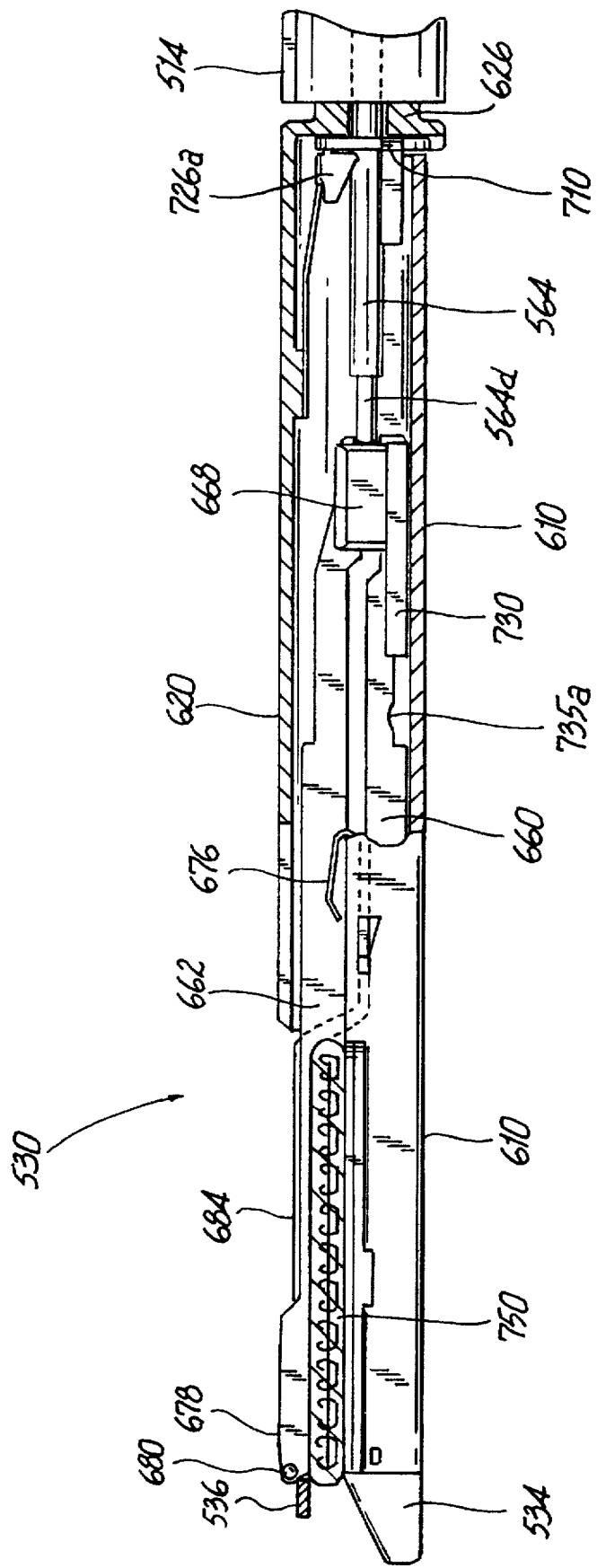
Figure 47:
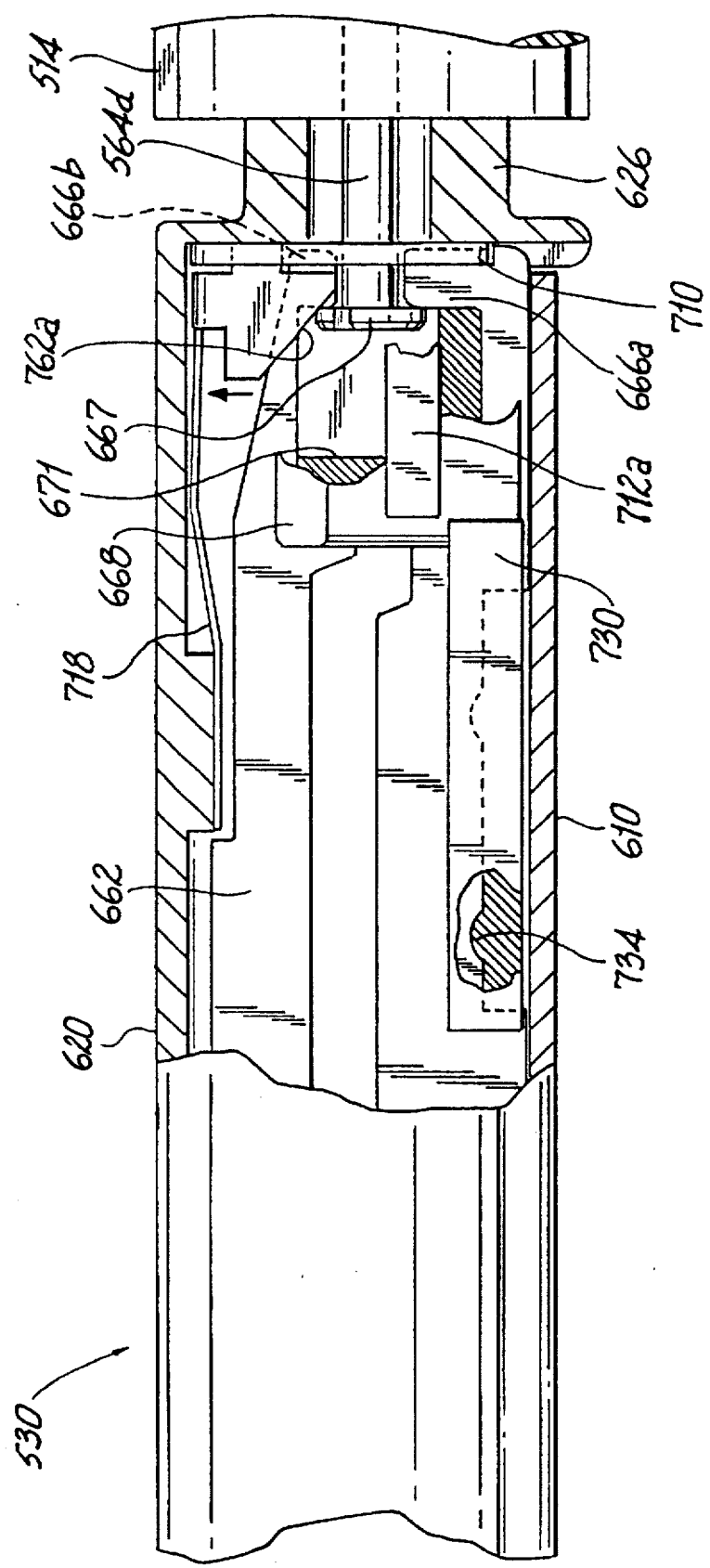
Figures 50, 51:
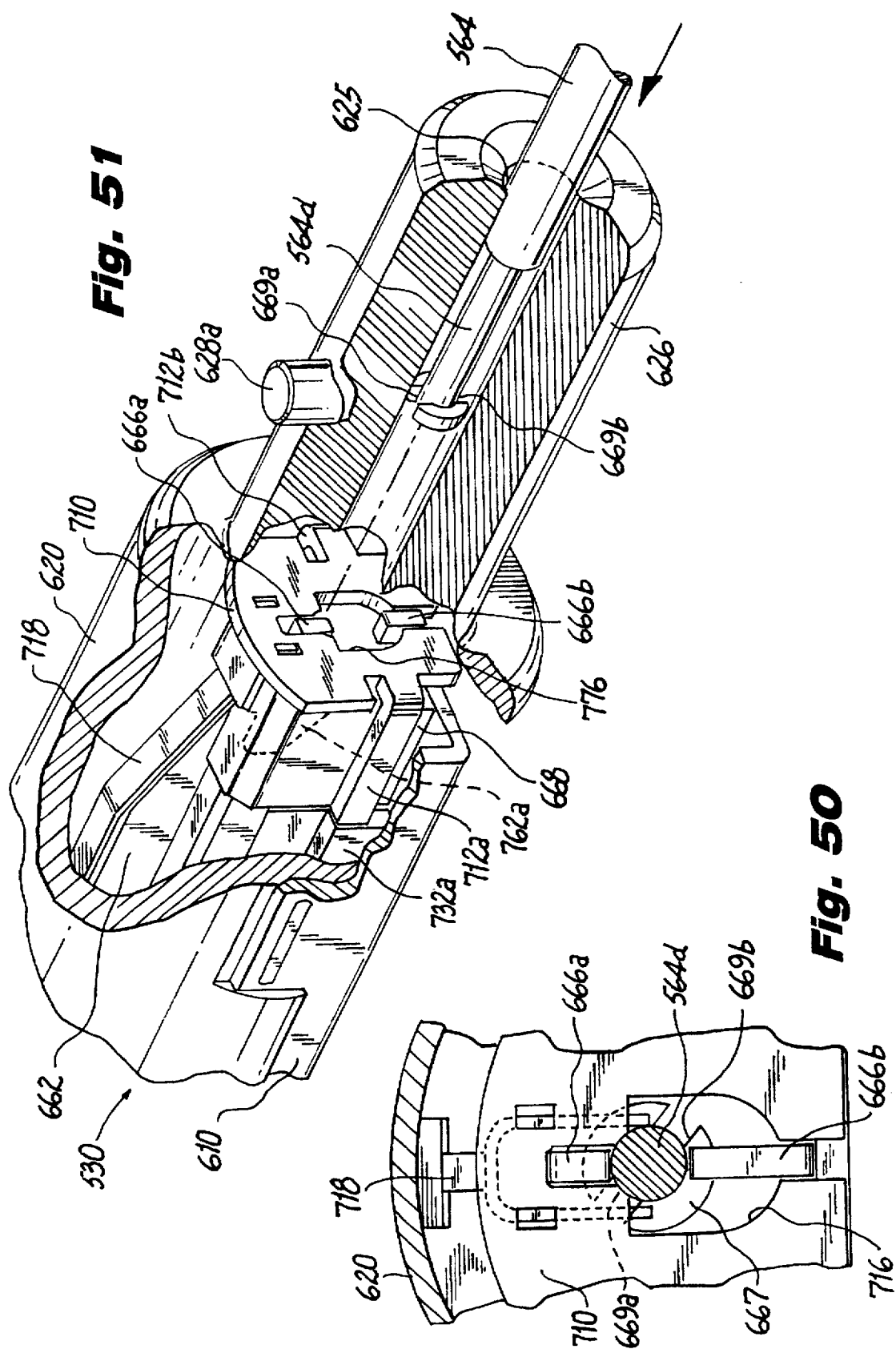
Figure 1:
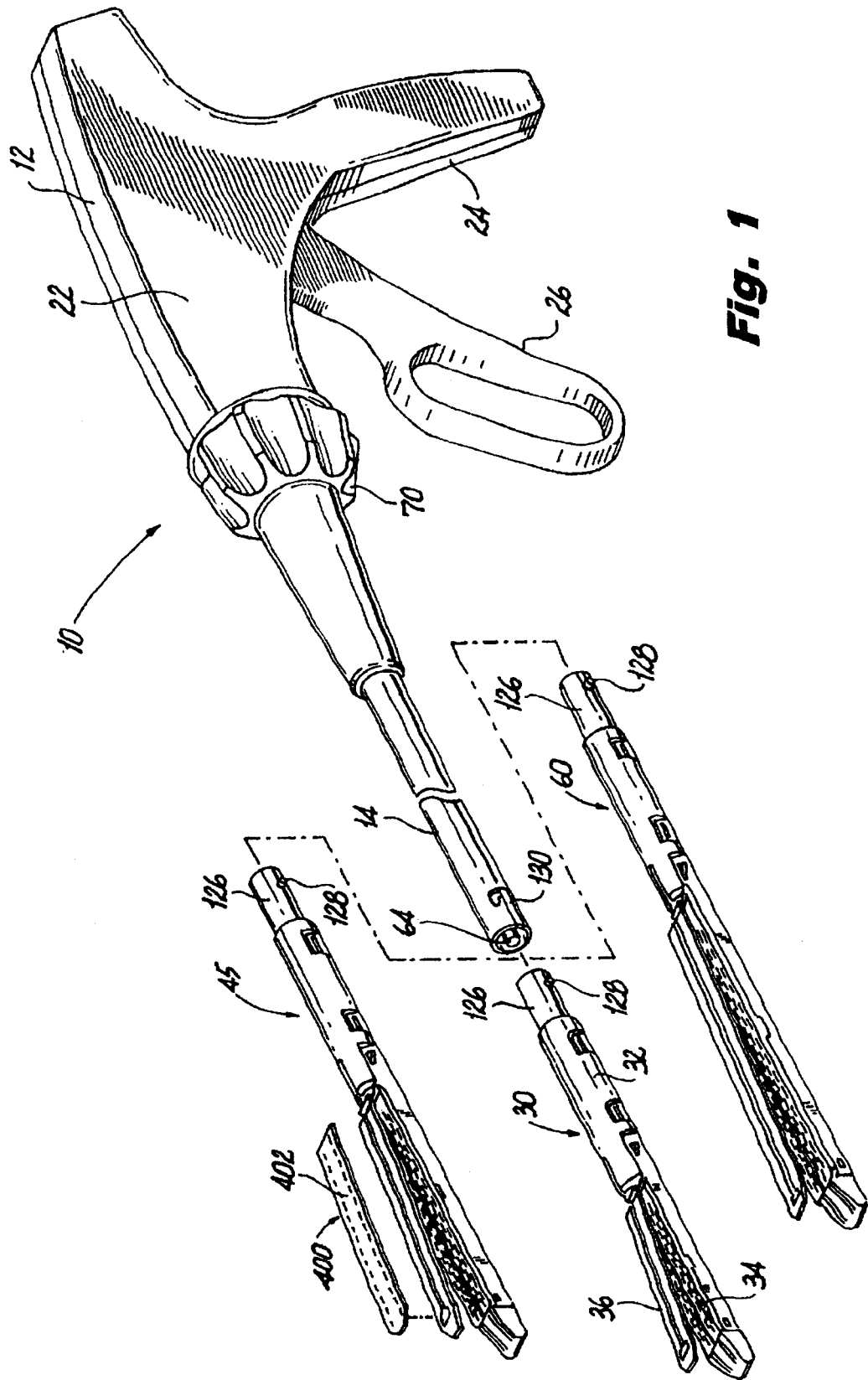
Figure 5:
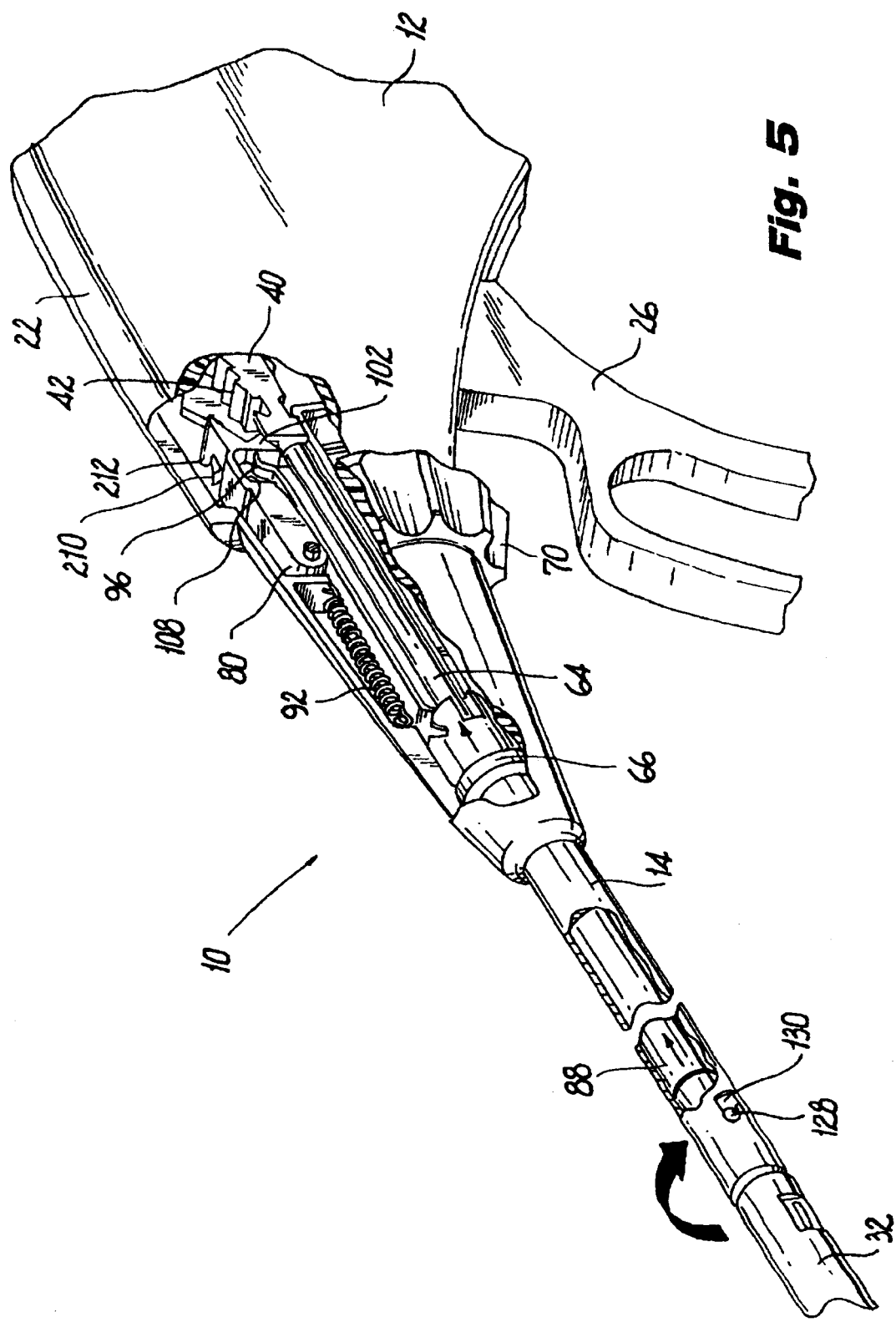

A plurality of spaced apart longitudinal slots 142 extend through staple cartridge 34 to accommodate the upstanding cam wedges 144 of actuation sled 140. Slots 142 communicate with a plurality of transverse retention slots 146 within which the plurality of fasteners 132 and pushers 134 are respectively supported. During operation, as actuation sled 140 translates through staple cartridge 34, the angled leading edges of cam wedges 144 sequentially contact pushers 136, causing the pushers to translate vertically within slots 146, urging the fasteners 134 therefrom. The result of the interaction between actuation sled 140 and pushers 136 is illustrated in FIGS. 12–14, and will be described hereinbelow with reference thereto. See also, commonly assigned U.S. Pat. No. 4,978,049 to Green, the disclosure of which is herein incorporated by reference in its entirety.

With continuing reference to FIG. 3, the anvil 36 of disposable loading unit 30 is provided with opposed mounting wings 150 and 152 which are dimensioned and configured to engage pivot apertures 154 and 156 in channel walls 114 and 116, respectively. A biasing member 158 having spring arms 158a and 158b is secured to the proximal end of anvil 36. The spring arms bear against internal bearing surfaces defined within mounting portion 120 to bias anvil 36 into a normally open position wherein the interior fastener forming surface 155 thereof is spaced from staple cartridge 34.

Disposable loading unit 30 further includes an axial drive assembly 160 for transmitting the longitudinal drive forces exerted by control rod 64 to actuation sled 140 during a stapling procedure. Drive assembly 160 includes an elongated drive beam 162 including a distal working head 164 and a proximal engagement section 166. Engagement section 166 includes a pair of engagement fingers 166a and 166b which are dimensioned and configured to mountingly engage a pair of corresponding retention slots 168a and 168b formed in a drive block 168. Drive block 168 has a proximal porthole 170 for receiving the distal end of control rod 64 when the proximal end of stapling unit 30 is inserted into the distal end of stapler body 14. Drive block 168 can be provided with an internal slot to receive a stem (not shown) from a distal end of control rod 64 to form a bayonet type connection, similar to that shown in connecting elongated body 14 to coupling stem 128. Such a connection would enable the user to manipulate drive beam 162 upon movement of control rod 64. The working end 164 of drive beam 162 is defined by a vertical support strut 172 which supports a knife blade 174, and an abutment surface 176 which engages the central support wedge 145 of actuation sled 140. Knife blade 174 travels slightly behind actuation sled 140 during a stapling procedure to form an incision between the rows of staple body tissue. A retention flange 178 projects distally from vertical strut 172 to retain a cylindrical cam roller 180. Cam roller 180 is dimensioned and configured to engage and translate with respect to the exterior camming surface 182 of anvil 36 to progressively clamp the anvil against body tissue during firing.

A longitudinal slot 184 extends through anvil 36 to accommodate the translation of retention flange 178 and vertical strut 172. A balancing flange 186 is secured to the working end of drive beam 162 through the engagement of retention foot 188 within a complementary retention port 190 formed in flange 186. Flange 186 serves to balance the clamping forces generated by cam roller 180 as anvil 36 is progressively clamped. A longitudinal slot 192 is formed in the base 112 of channel 110 to accommodate the longitudinal translation of retention foot 188 during firing.

With reference to disposable loading unit 45 in FIG. 1, an anvil cover is provided to protect tissue from moving parts along the exterior of anvil 36. In particular, anvil cover 400 has channel 402 formed on an underside thereof and is secured to an upper surface of anvil 36 to form a channel therebetween. Cam roller 180 travels in channel 402 between cover 400 and anvil 36 during firing. Anvil cover 400 is preferably plastic, but can be fabricated from any suitable biocompatible material.

Returning to FIG. 3, dual constant force spring members 194 and 196 are connected to the proximal end of channel base 112 and are disposed distal of drive block 168 to bias the block against distal movement. As best seen in FIGS. 12–14, when drive block 168 translates distally, spring members 194 and 196 unwind until they are passed over by the block at the end of its travel. At such a time, the spring members return to their normally wound position providing a buffer for the mounting block. Thus, an attempt to return the block to the proximal most position after firing the disposable loading unit will be inhibited.

Referring now in sequential order to FIGS. 4–11, to initiate the operation of instrument 10, a desired disposable loading unit is selected. Such disposable loading unit can be one of the different sized disposable loading units illustrated in FIG. 1 or one of the disposable loading units adapted to apply surgical clips (FIG. 15) or other types of surgical staples (FIG. 16). Use of the instrument will be discussed herein using a disposable loading unit adapted to apply linear rows of staples. Disposable loading unit 30, is mounted to the stapler by inserting the proximal mounting section thereof into the distal end of the elongated body 14, as shown in FIG. 4. Prior to insertion, support tube 88 is in its distal-most position within elongated body 14 and it is maintained in that position by spring 92. Accordingly, the cam finger 96 of beam 82 maintains rack lock 80 in a disengaged uplifted position, spaced from the toothed rack 42 of actuation shaft 40.

Once the proximal end of the disposable loading unit is inserted into the distal end of elongated body 14, it is rotated approximately 10° to 15° to position coupling stem 128 in the base of coupling slot 130. Thereupon, the bias of spring 92 urges support tube 88 distally to lock stem 128 within the base of slot 130. If a coupling system is provided between control rod 64 and drive block 168 (discussed above) such rotation would couple these member as well. In addition, as illustrated in FIG. 5, when support tube 88 is shifted proximally by the insertion of the proximal section 126 of mounting portion 120 into elongated body 14, arcuate cam finger 96 of beam 82 translates proximally against cam surface 98 until it reaches recess 108. Thereupon rack lock 80 moves into an engagement position under the bias of torsion spring 106, and instrument 10 is ready for use.

Figure 6:
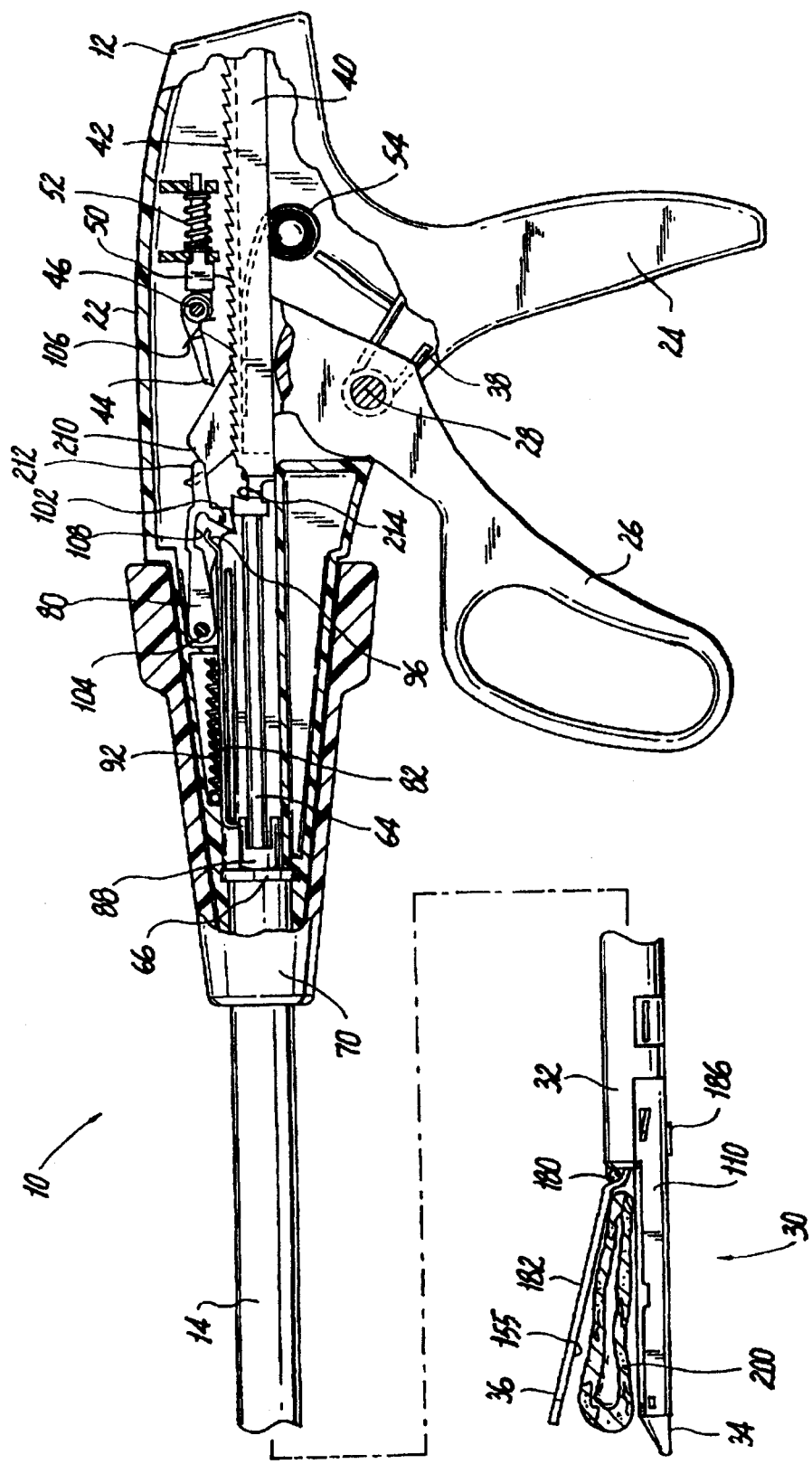
FIG. 6 is a side elevational view of the surgical stapling apparatus of the subject application with the handle portion sectioned to illustrate the relative positions of the components of the actuation assembly housed therein prior to actuation.
Figure 7:
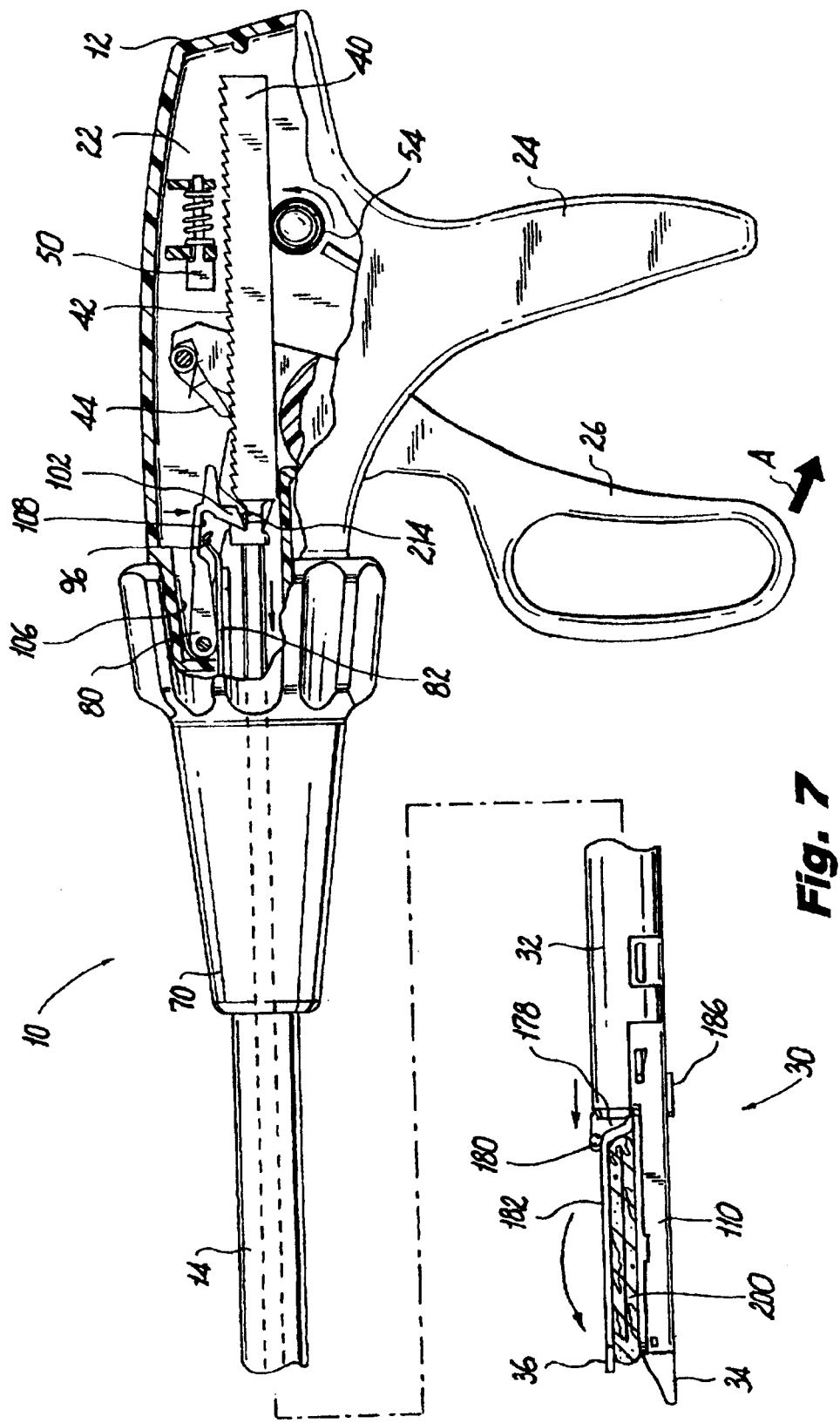
Figure 8:
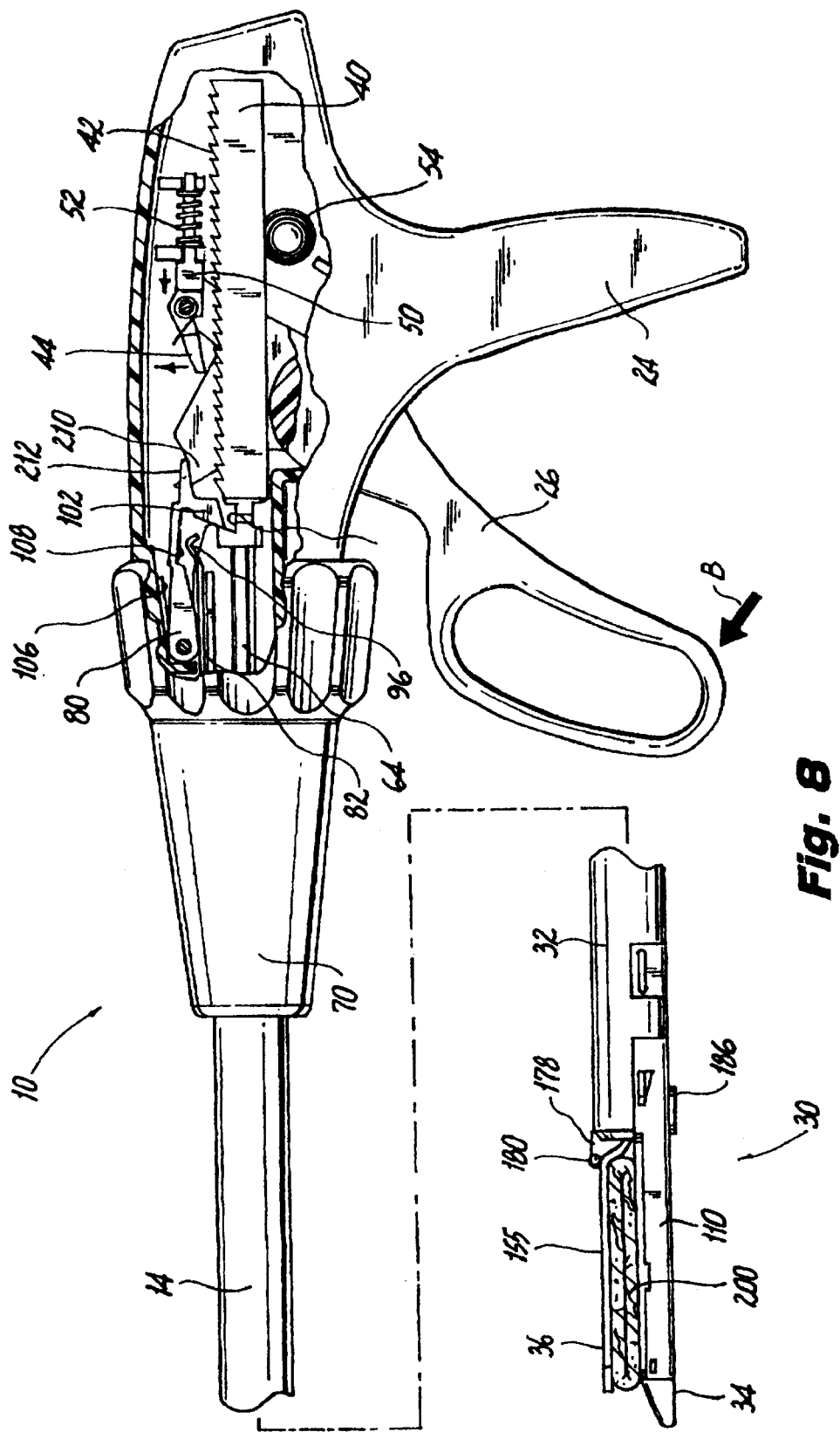
Figure 9:
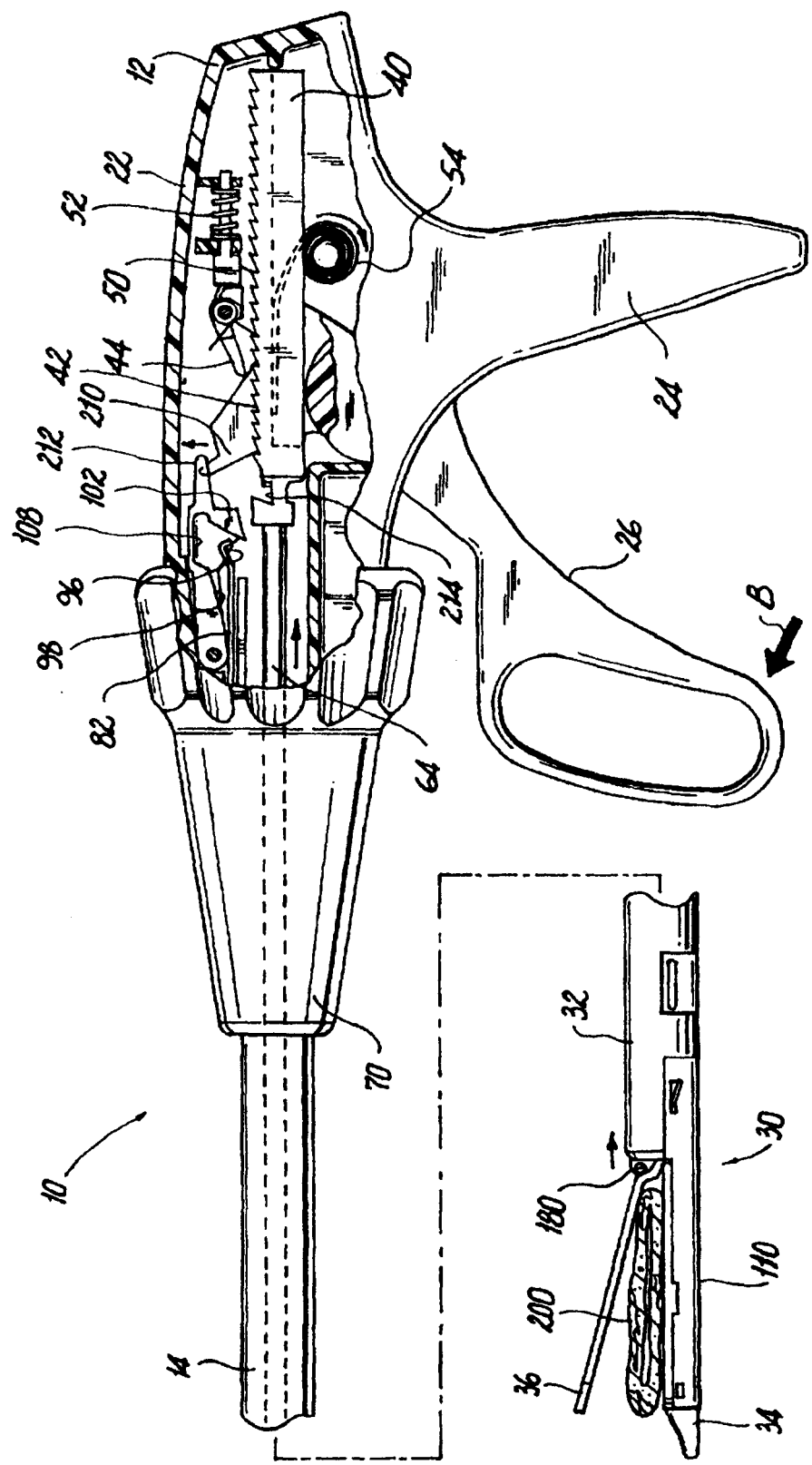
Figure 10:
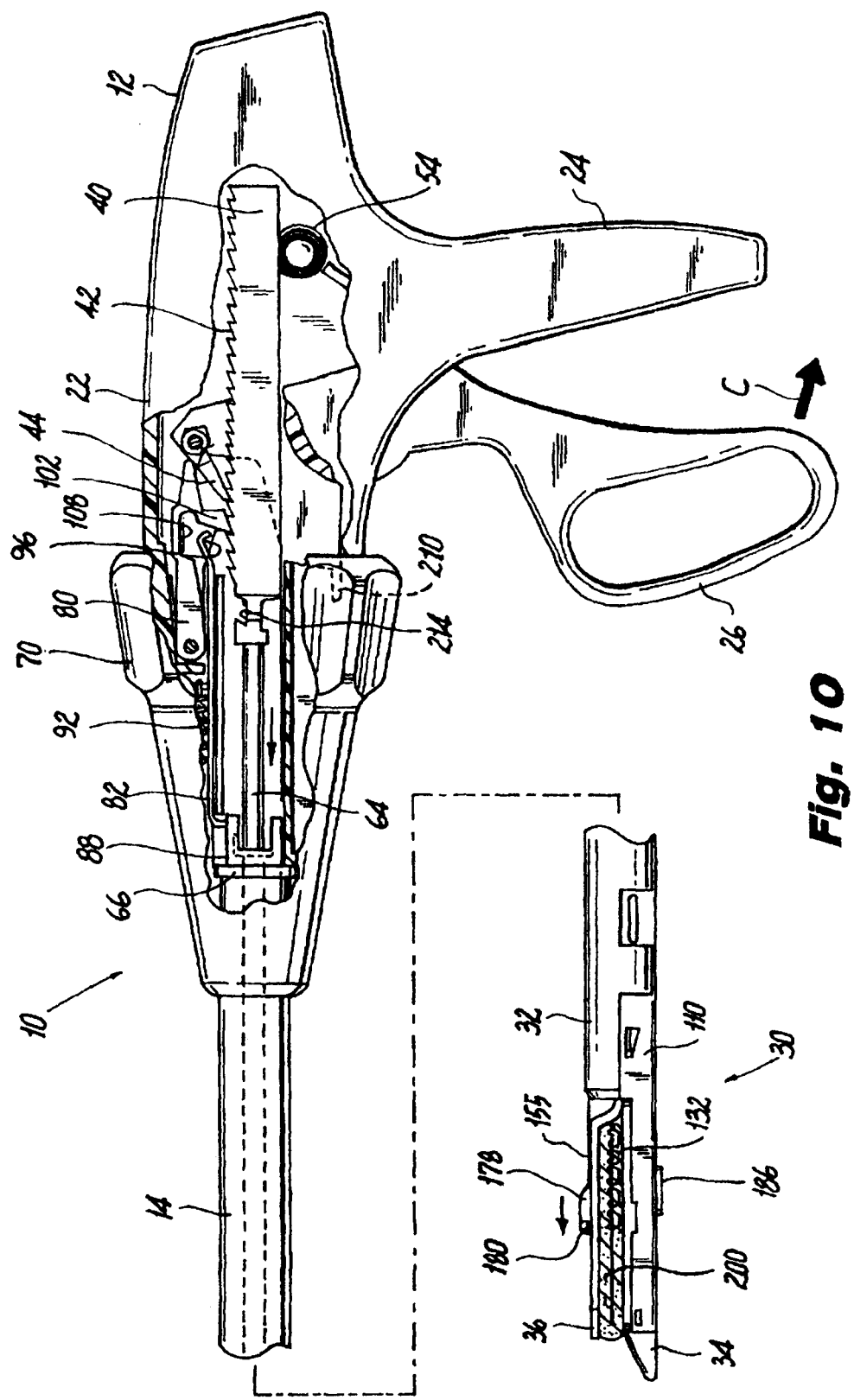
Figure 11:
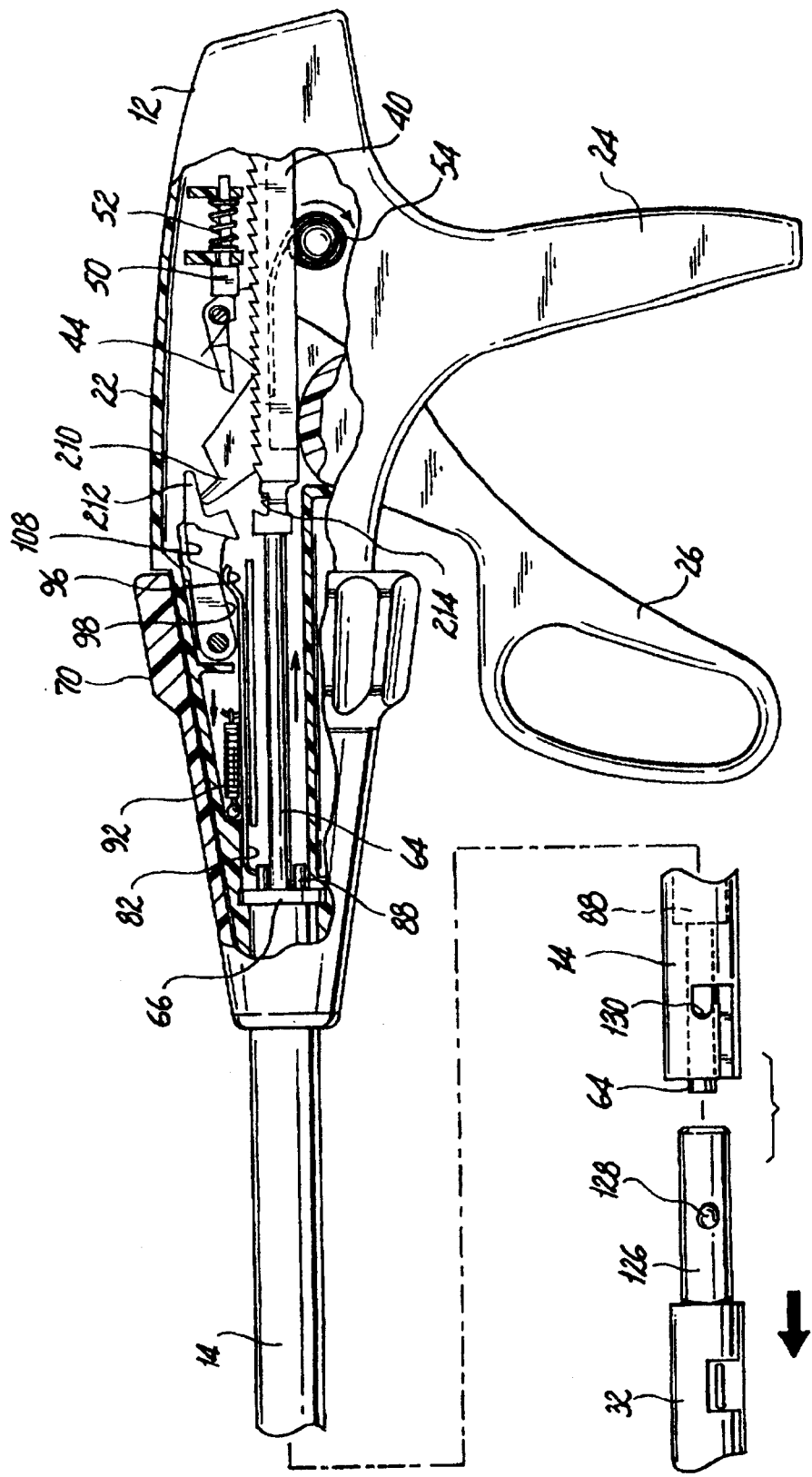
Figure 14:
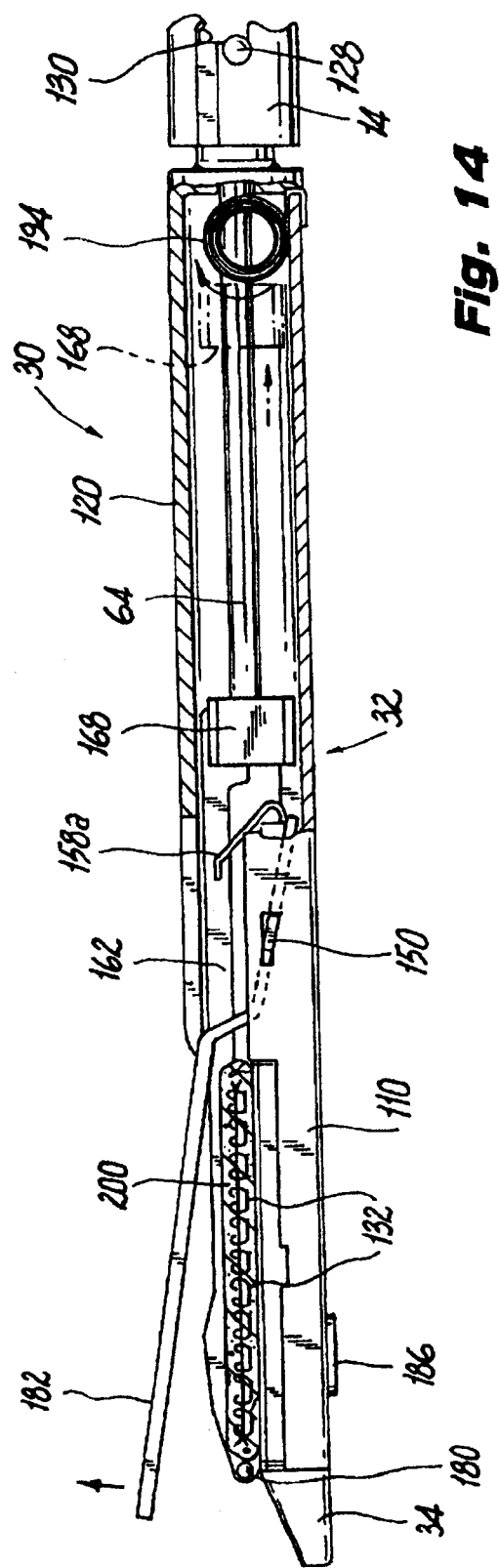

Turning to FIG. 6, prior to utilization, actuation handle 26 is in the illustrated neutral position. In this position, pawl 44 is spaced from the toothed rack 42 of actuation shaft 40. In addition, lift arm 210 which projects distally from actuation handle 26 is engaged beneath a transverse finger 212 formed at the proximal end of rack lock 80 adjacent the wedged clasp portion 102. Lift arm 210 serves to disengage clasp portion 102 from actuation shaft 40 under certain operating conditions which will be discussed hereinbelow with respect to FIGS. 8 and 9.

Prior to manipulating actuation handle 26, actuation shaft 40 is in its proximal-most position, as is control rod 64, biased against distal movement by constant force spring 54. Accordingly, anvil 36 is in an open position biased against closure by spring arms 158a and 158b. Thus, at such a time, body tissue such as tubular vessel 200 may be captured between the fastener forming surface of anvil 36 and the tissue contacting surface of staple cartridge 34.

Figure 7:
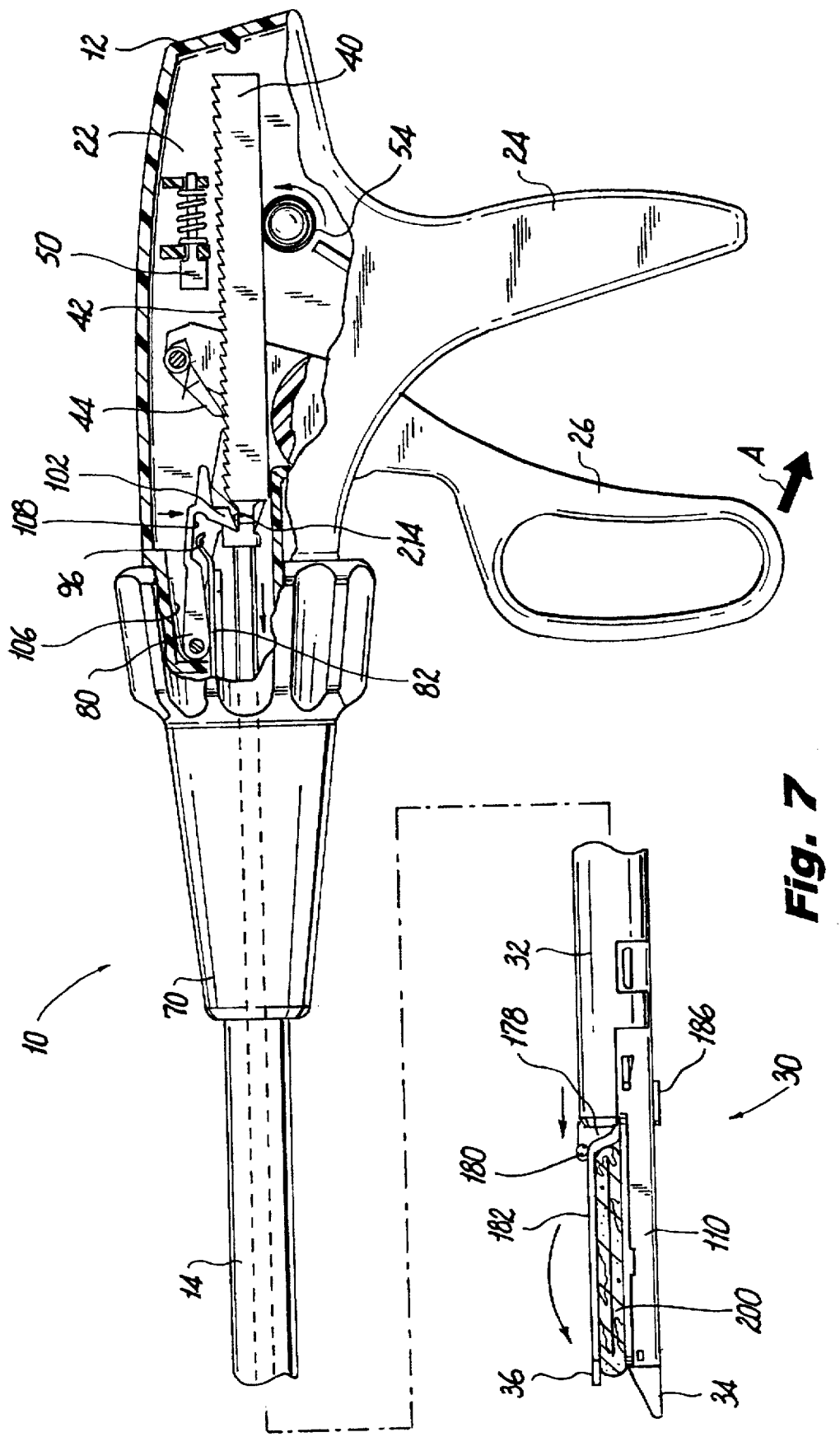
FIG. 7 is a side elevational view of the surgical stapling apparatus of the subject application with the handle portion sectioned to illustrate the relative positions of the components of the actuation assembly when the actuation handle is partially compressed to move the anvil of the disposable loading unit to a closed position.

Turning now to FIG. 7, manipulation of actuation handle 26 in the direction indicated by reference arrow "A" causes pawl 44 move distally and rotate counterclockwise to engage toothed rack 42 and drive actuation shaft 40 distally against the bias of spring 54. As a result, control rod 64 is driven distally, forcing drive block 168 forward within disposable loading unit 30. Accordingly, a working end 164 of drive beam 162 translates distally and cam roller 180 engages the proximal end portion of the cam surface of anvil 36, causing the anvil to move into a closed position, clamping tubular vessel 200 against the tissue contacting surface of staple cartridge 34. In addition, when actuation shaft 40 advances distally, the clasp portion 102 of rack lock 80 engages a notched area 214 formed in the distal end portion of actuation shaft 40 distal of toothed rack 42 under the bias of torsion spring 106. Thereupon, the longitudinal position of actuation shaft 40 within barrel portion 22 is maintained, and anvil 36 is locked in a closed position.

Figure 8:
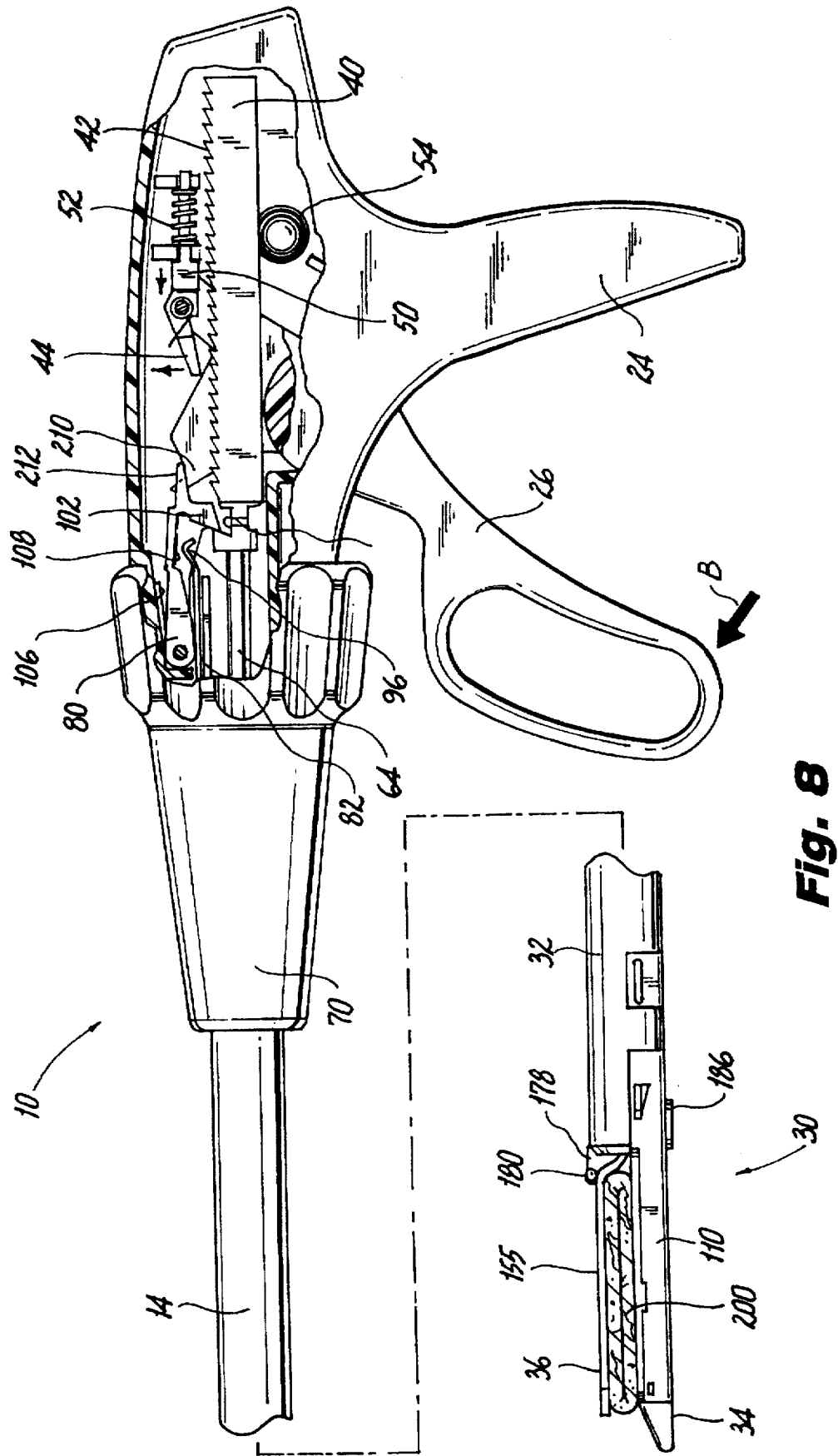
FIG. 8 is a side elevational view of the surgical stapling apparatus of the subject application with the handle portion sectioned to illustrate the relative positions of the components of the actuation assembly when the actuation handle is released to permit the anvil of the disposable loading unit to move to an open position.
Figure 9:
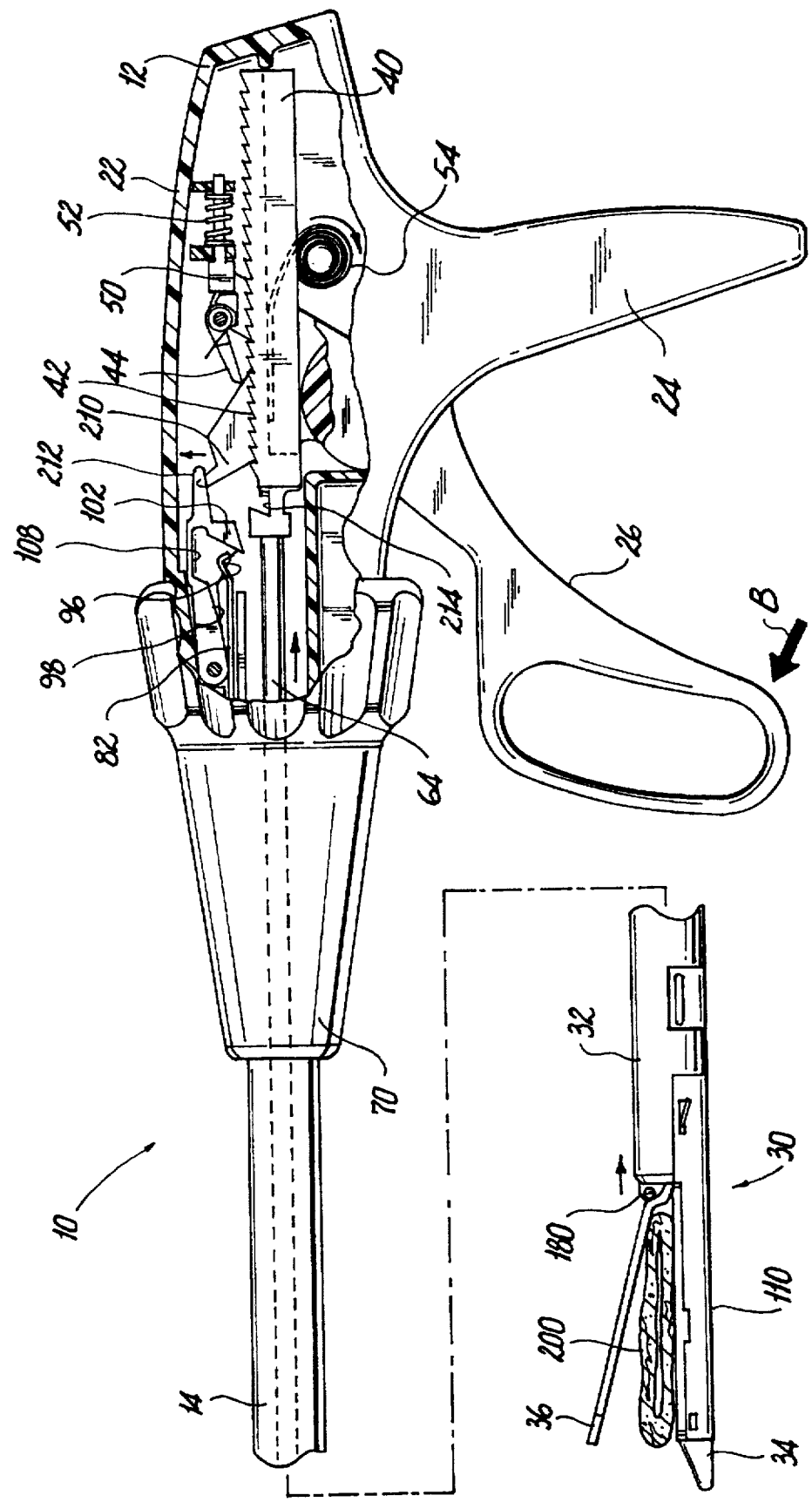
FIG. 9 is a side elevational view of the surgical stapling apparatus of the subject application with the handle portion sectioned to illustrate the relative positions of the components of the actuation assembly when the actuation handle is moved to a position wherein the anvil of the disposable loading unit is maintained in an open position.

Under certain circumstances it may be necessary to open the anvil and unclamp the captured vessel or body tissue, i.e., to recapture the vessel at a different location. As illustrated in FIG. 8, to release the anvil, actuation handle 26 is manipulated in the direction indicated by reference arrow "B" against the bias of linear compression spring 52. As a result, arm 210 lifts finger 212, rotating rack lock 80 in a counter-clockwise direction against the bias of torsion spring 106, as shown in FIG. 9. The clasp portion 102 of rack lock 80 is thereby disengaged from notched area 214, permitting actuation shaft 40 and control rod 64 to return to their proximal-most positions. At such a time, drive block 168 moves proximally under the bias of spring members 194 and 196. Accordingly, cam roller 180 is drawn off of the exterior camming surface 182 of anvil 36, and the anvil moves to an open position under the bias of spring member 158. Subsequent anvil closure is achieved in the manner described hereinabove with reference to FIG. 7.

Figure 10:
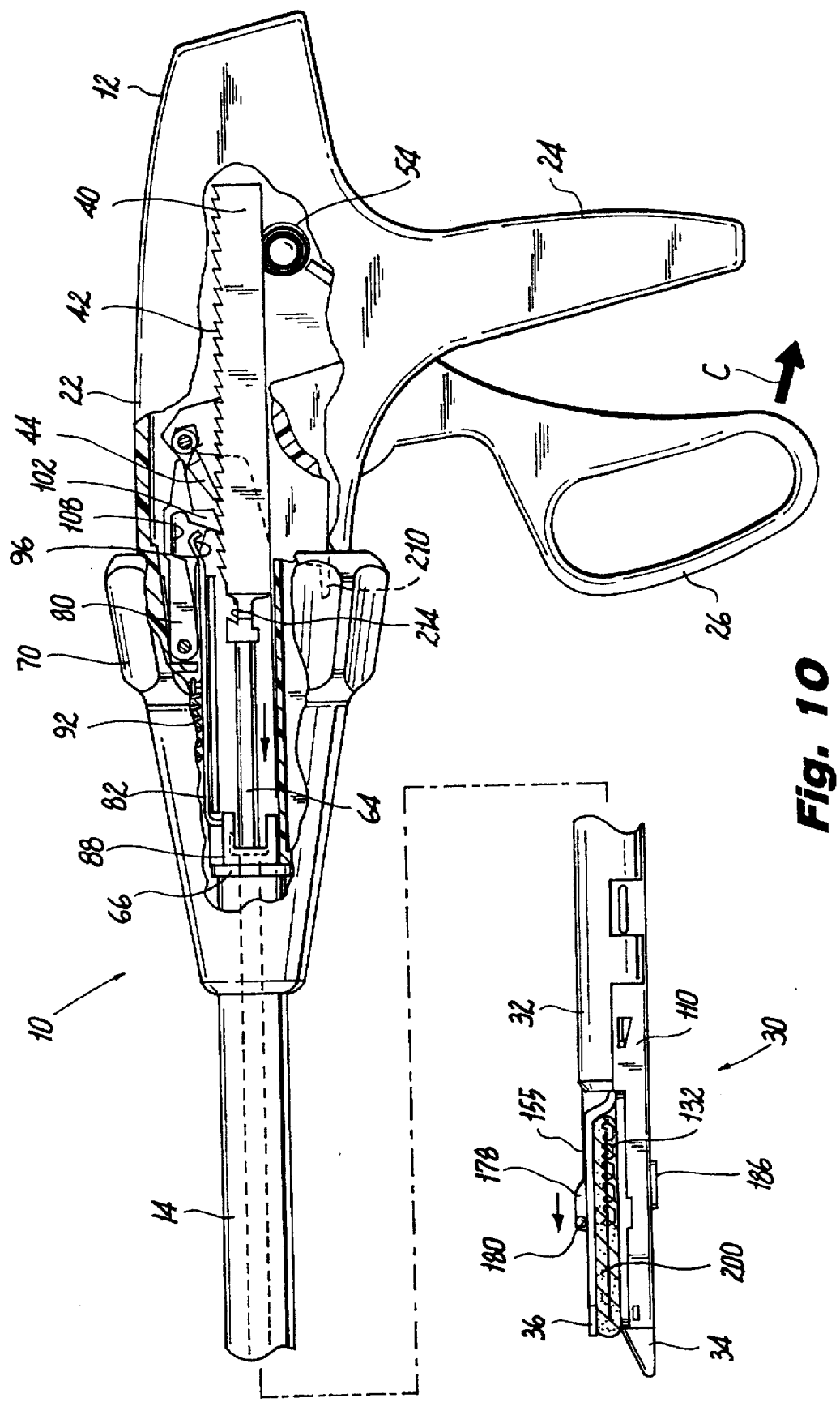
FIG. 10 is a side elevational view of the surgical stapling apparatus of the subject application with the handle portion sectioned to illustrate the relative positions of the components of the actuation assembly when the actuation handle is manipulated through one complete actuation stroke to apply a portion of the staples from the staple cartridge of the disposable loading unit to body tissue.

Referring to FIG. 10, to fire instrument 10 and apply a plurality of surgical fasteners 132 to the tissue clamped between anvil 36 and staple cartridge 34, actuation handle 26 is manipulated toward stationary handle 24 in the direction indicated by reference arrow "C" against the bias of torsion spring 38. Thereupon, pawl 44 engages toothed rack 42 and drives actuation shaft 40 distally against the bias of constant force spring 54. In a preferred embodiment of firing a disposable loading unit having linear rows of staples, one complete stroke of actuation handle 26 causes actuation shaft 40 to advance approximately 15 mm within barrel portion 22, urging drive beam 162 an equivalent distance within disposable loading unit 30 as control shaft 64 transmits longitudinal motion thereto. As a result, half of the surgical fasteners 132 within 30 mm staple cartridge 34 are ejected therefrom upon moving actuation handle 26 one complete stroke. Actuation shaft 40 is maintained in this longitudinally advanced position through the engagement of the clasp portion 102 of rack lock 80 and the toothed rack 42. Subsequent release and movement of actuation handle 26 to a relaxed position will therefore have no bearing on the longitudinal position of actuation shaft 40.

To complete the staple firing operation, actuation handle 26 is once again approximated toward stationary handle 24, causing pawl 44 to engage toothed rack 42 and advance actuation shaft 40 in a distal direction another 15 mm. Thus, two complete strokes of actuation handle 26 causes actuation shaft 40 to advance 30 mm within barrel portion 22, urging the working end 164 of drive beam 162 through staple cartridge 34 to sequentially eject all of the surgical fasteners therefrom. If desired, the operator can incrementally advance control shaft 64 by multiple short strokes, wherein the minimum advancement is dictated by the linear distance between the teeth on rack 42. Therefore, while two complete strokes of the preferred stroke distance of 15 mm can be used (to fire a 30 mm disposable loading unit), complete strokes are not necessary or required.

As best seen in FIGS. 12-14, two complete strokes of actuation handle 26 causes actuation shaft 40 and the associated control rod 64 to translate from the proximal-most position illustrated in FIG. 12, wherein drive block 168 is disposed adjacent the proximal end of channel 110, to the distal-most position illustrated in FIG. 13, wherein drive block 168 travels to the distal end of staple cartridge 34. During its travel, drive block 168 urges drive beam 166 distally, effectuating progressive closure of anvil 36 against tubular vessel 200, and sequential ejection of surgical fasteners 132 into the body tissue as actuation sled 140 travels through staple cartridge 34. As shown in FIG. 13, when cam roller 180 reaches the distal end of its travel, it drops into the transverse slot 185 formed at the distal end of anvil slot 184. As a result, anvil 36 returns to an open position under the bias of spring member 158, releasing the stapled body tissue as illustrated in FIG. 14. Furthermore, spring members 194 and 196 rewind and return to a coiled condition at the proximal end of channel 110.

Figure 11:
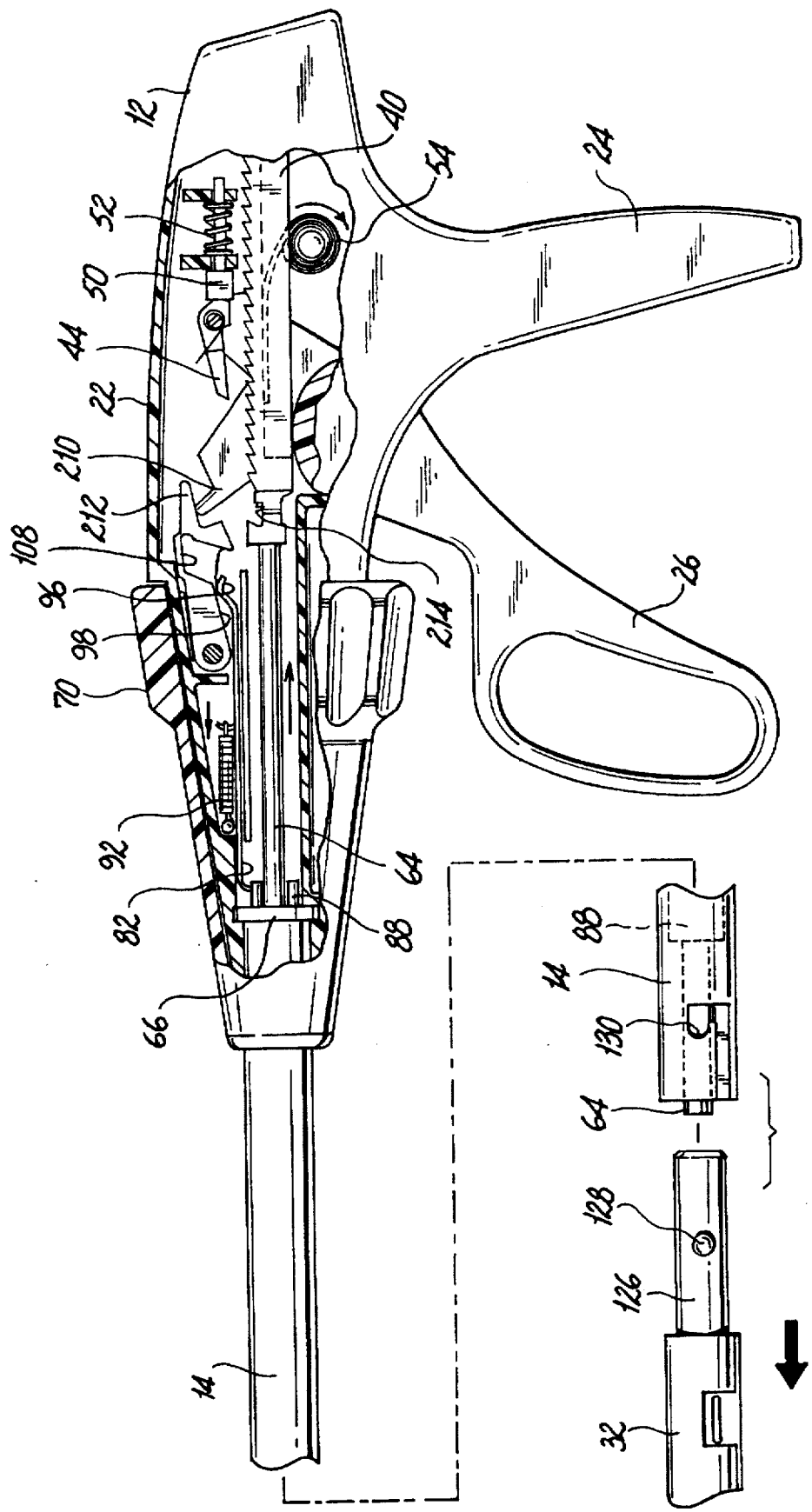
FIG. 11 is a side elevational view of the surgical stapling apparatus of the subject application with the handle portion sectioned to illustrate the relative positions of the components of the actuation assembly when the disposable loading unit is removed from the distal end of the stapler body.

At the conclusion of the above-described firing operation, disposable loading unit 30 is removed from the distal end of elongated body 14, as illustrated in FIG. 11. At such a time, support tube 88 is permitted to return to its distal-most position under the bias of spring 92. Accordingly, beam 82 translates distally causing arcuate cam finger 96 to lift rack lock 80 out of engagement with the toothed rack 42 of actuation shaft 40. As a result, actuation shaft 40 returns to its proximal-most position within barrel portion 22 under the bias of constant force spring 54. Thereupon, a new disposable loading unit can be joined with the instrument and another surgical task performed.

If the surgeon desires to apply parallel rows of staples each measuring about 45 mm in length, disposable loading unit 45 (FIG. 1) is mounted to the distal end portion of elongated body 14. After mounting, actuation handle 26 is manipulated through a number of strokes equalling three complete actuation strokes to incrementally advance actuation shaft 40 and control rod 64 a distance of 45 mm. Alternatively, if disposable loading unit 60 is selected for utilization to apply staple rows measuring about 60 mm in length, actuation handle 26 must be manipulated through a number of strokes equalling four complete actuation strokes to incrementally advance actuation shaft 40 and control rod 64 a distance of 60 mm.

Turning to FIGS. 15 and 16, two alternate embodiments of disposable loading units are shown. Disposable loading unit 410 in FIG. 15 is designed to apply surgical clips. Disposable loading unit 410 has jaw structure 412 and a plurality of clips disposed in housing 414. Commonly assigned U.S. Pat. No. 5,100,420, the disclosure of which is herein incorporated by reference in its entirety, discloses a manner in which clips can be fed to jaw structure 412 and formed. Disposable loading unit 420 in FIG. 16 is designed to apply individual surgical staples, such as those useful during hernia repair. Disposable loading unit 420 has jaw structure 422 and a plurality of staples disposed in housing 424. Commonly assigned U.S. Pat. No. 5,289,963, the disclosure of which is herein incorporated by reference in its entirety, discloses a manner in which staples can be fed to jaw structure 422 and formed. Both disposable loading units 410 and 420 are secured to the surgical instrument in a manner similar to the disposable loading units previously described and are actuated by the longitudinal motion of actuation shaft 40 and control rod 64.

It is readily apparent and may be appreciated by those having ordinary skill in the art that the stroke distance travelled by the actuation shaft may be adjusted in accordance with desired surgical practices. For example, it may be desirable to employ disposable loading units which apply parallel staple rows measuring 40 mm, 60 mm, or 80 mm. Thus, the incremental stroke distance travelled by the actuation shaft could be adjusted to approximately 20 mm intervals. In addition, one skilled in the art could provide alternate structure or orientation of structures to control the advancement of control rod 64. For example, toothed rack 42 could be rotated so the teeth face downward towards the handles and the locks and pawls moved to engage the rack from the underside. Also, various safety mechanisms can be added, such as a lockout in the handle that needs to be released prior to actually firing a disposable loading unit.

Although the subject invention has been described with respect to preferred embodiments, it will be readily apparent to those having ordinary skill in the art to which it appertains that changes and modifications may be made thereto without departing from the spirit or scope of the subject invention as defined by the appended claims.

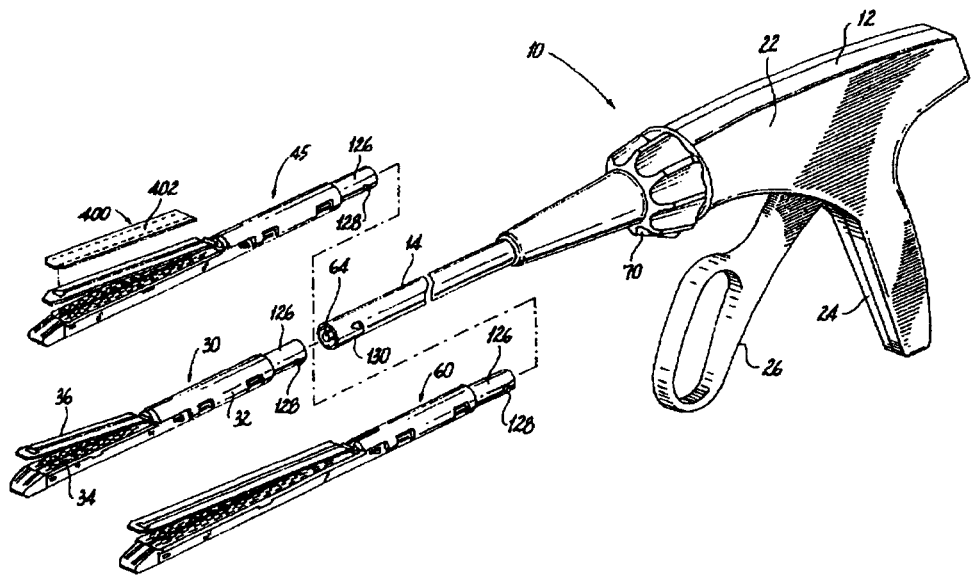

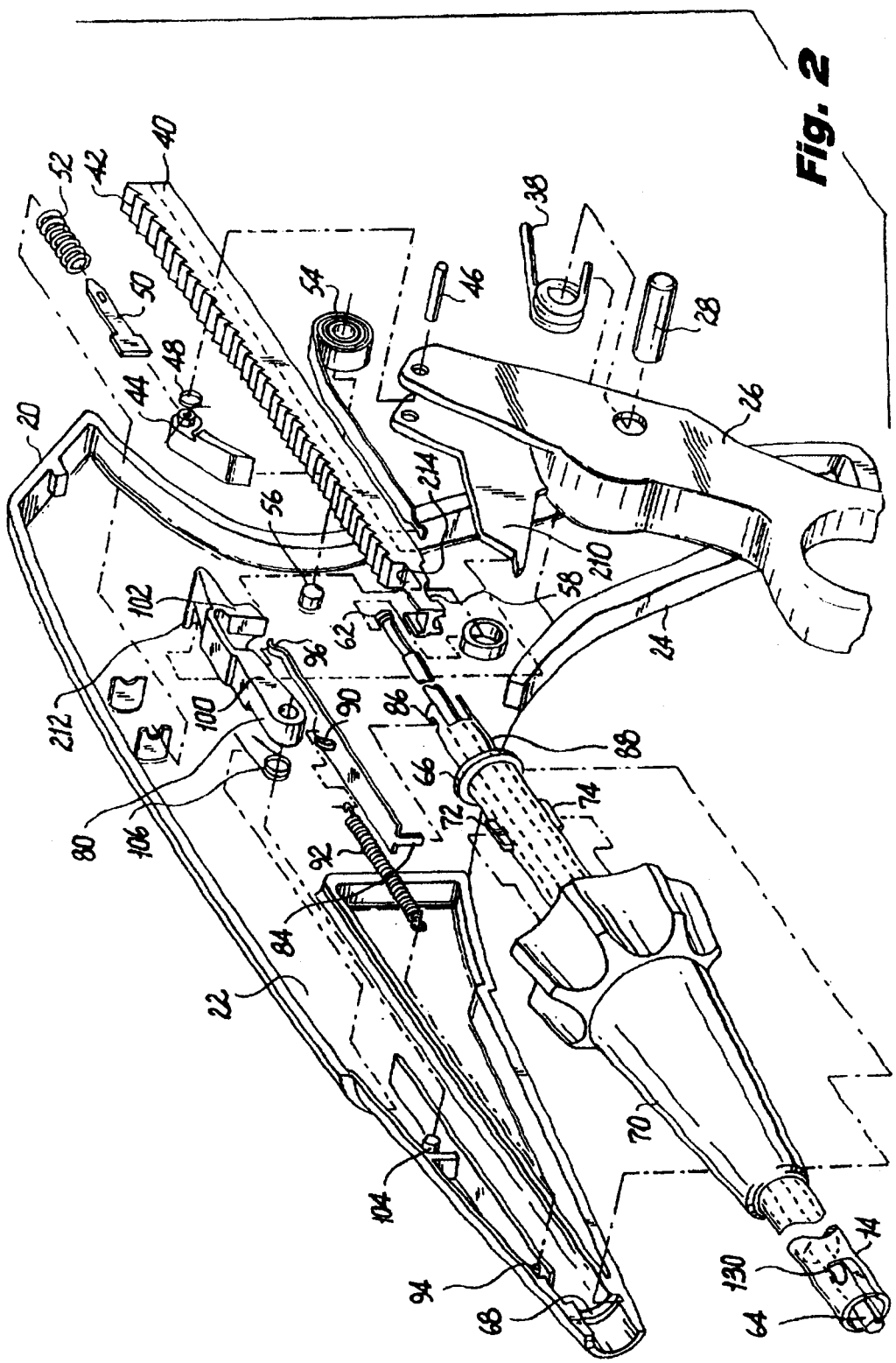

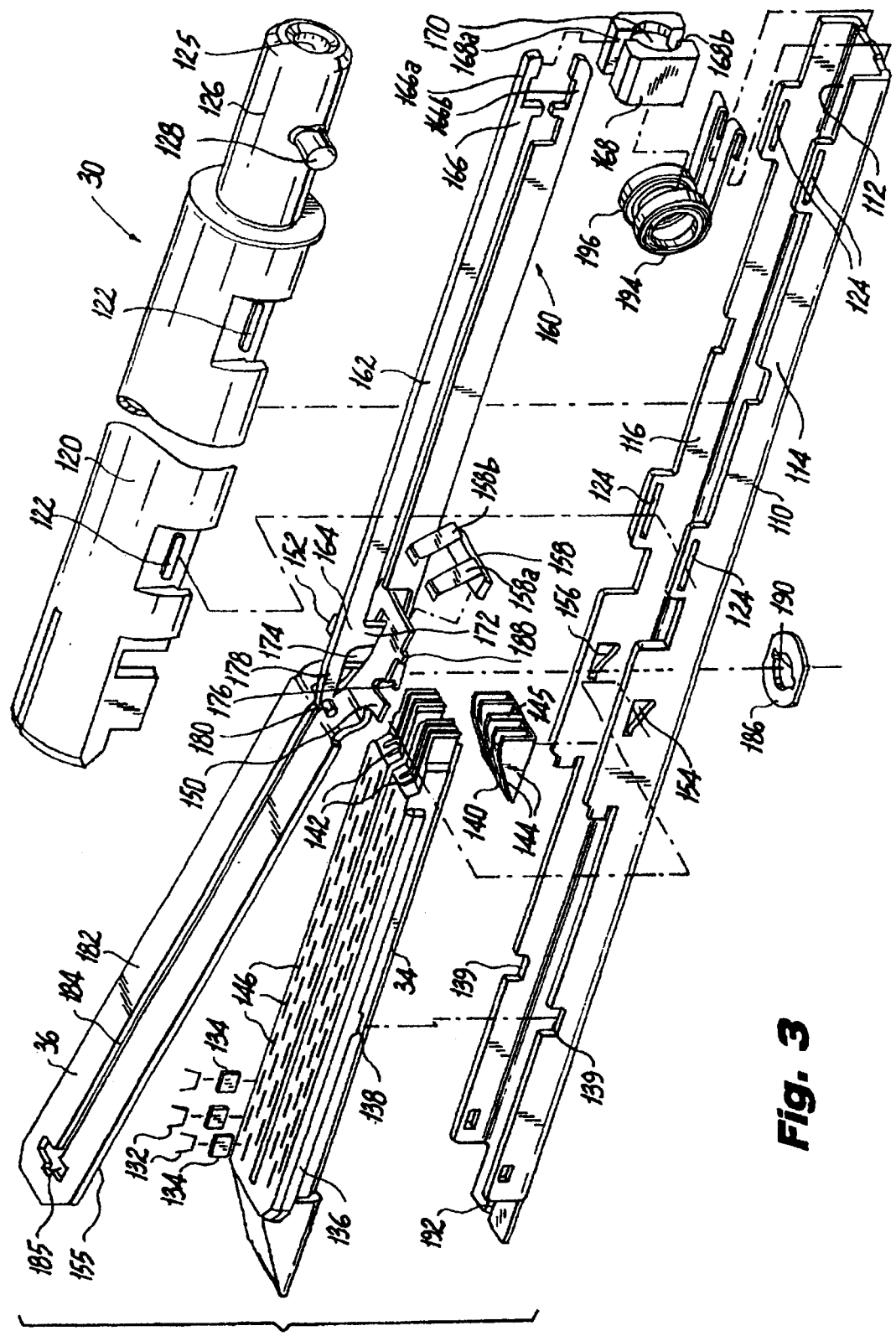

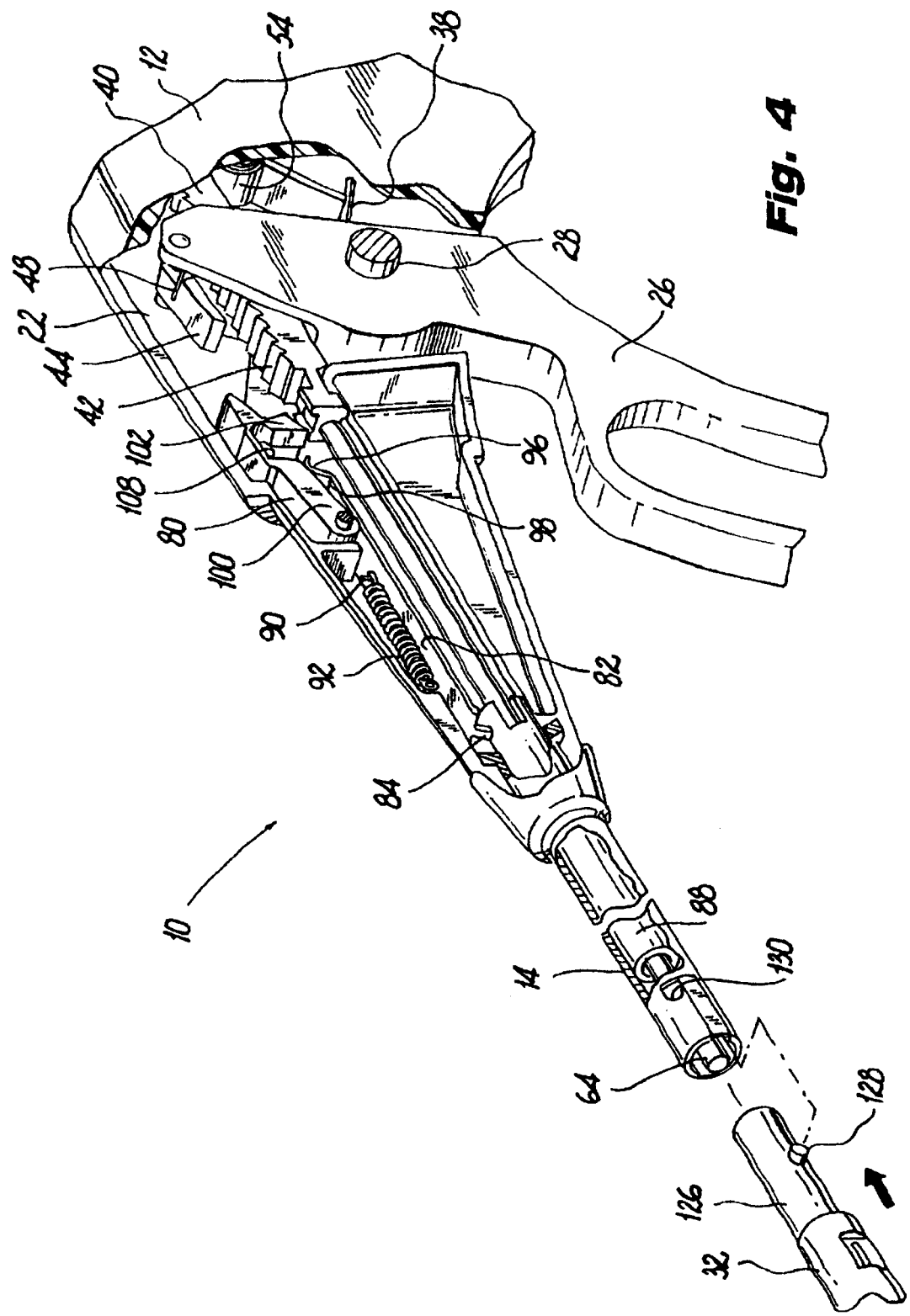

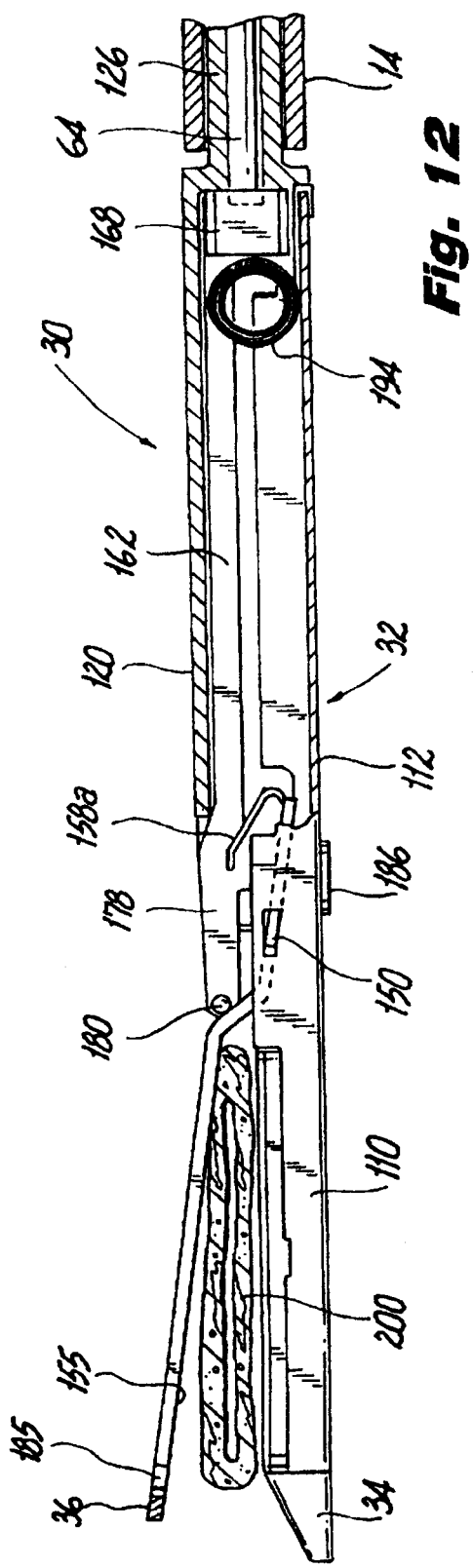
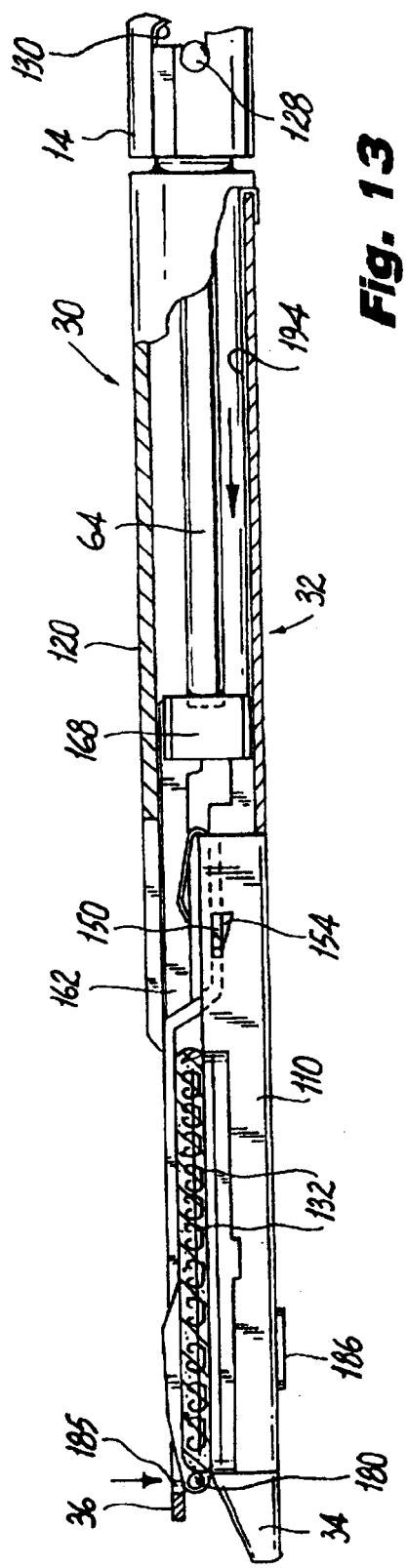

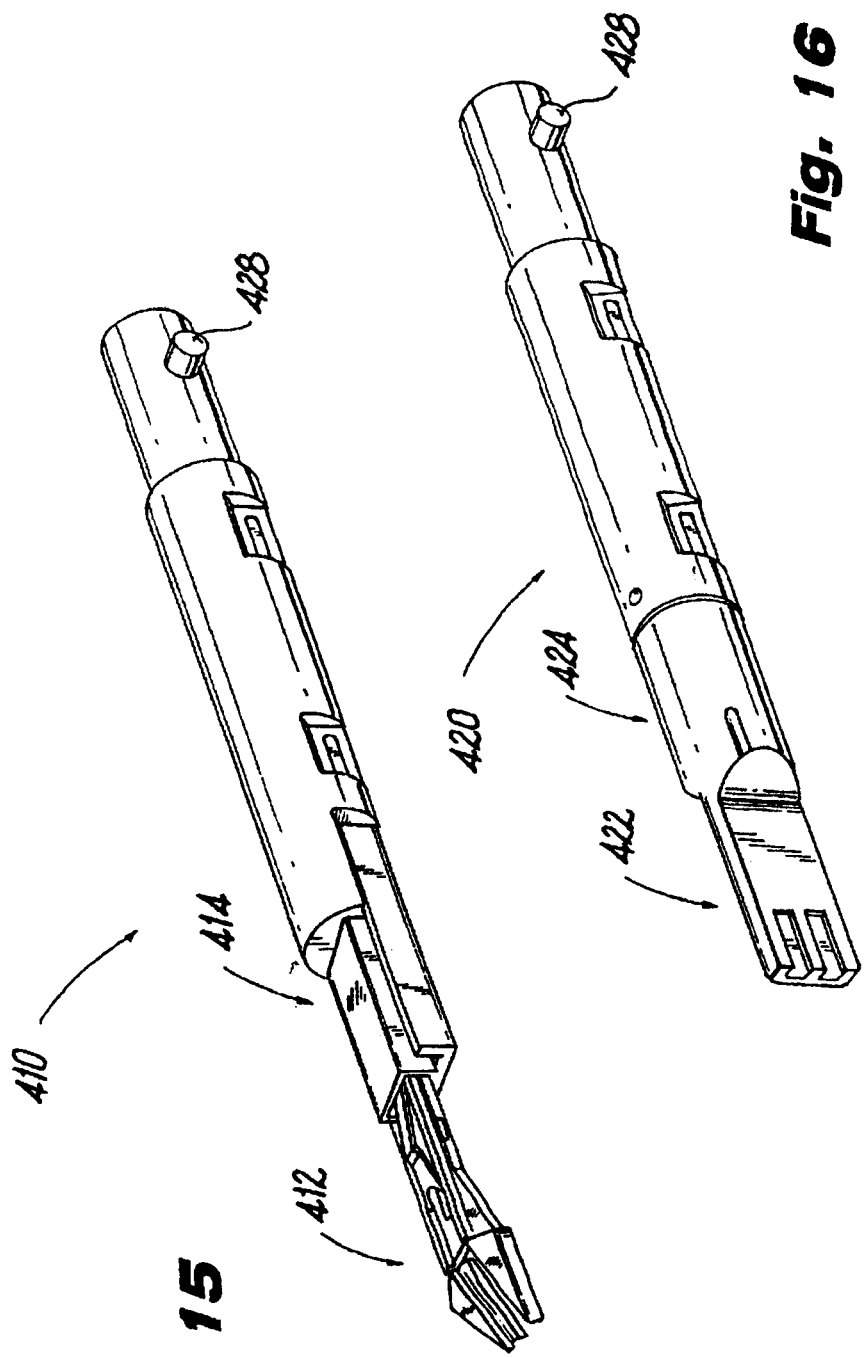

What is claimed is:

1. A surgical stapler comprising:
   a) a handle assembly including a housing and an actuation handle movable through an actuating stroke;
   b) an elongated body extending distally from the handle assembly housing and defining a longitudinal axis;
   c) an elongated actuation shaft supported at least in part within the handle assembly housing and having a particular linear dimension, the actuation handle interacting with the actuation shaft such that manipulation of the actuation handle through a complete actuating stroke causes the actuation shaft to translate through a predetermined linear distance; and
   d) a disposable loading unit operatively engaged in a distal portion of the elongated body and including a staple cartridge containing a plurality of staples, an actuator movable through the staple cartridge for ejecting the staples therefrom, and an anvil against which the staples are driven when ejected from the staple cartridge to form a staple line having a particular linear dimension, the linear dimension of the staple line corresponding to the distance through which the actuation shaft translates in response to manipulation of the actuation handle through a particular number of complete actuation strokes numbering more than one.

2. A surgical stapler as recited in claim 1, wherein the actuation shaft is defined at least in part by a toothed rack having a particular rack length, and the actuation handle has a pawl member for selectively engaging the toothed rack and advancing the actuation shaft in response to manipulation of the actuation handle.

3. A surgical stapler as recited in claim 2, wherein the linear dimension of the staple line is proportional to the rack length of the toothed rack.

4. A surgical stapler as recited in claim 2, wherein the actuation handle is movable through a clamping stroke in which the actuation shaft translates through a predetermined clamping distance causing the anvil to move between an open position and a closed position, the clamping stroke preceding the first of any number of complete actuation strokes.

5. A surgical stapler as recited in claim 5, wherein an engagement hook is mounted within the handle assembly housing to selectively maintain the actuation shaft in a particular position after traveling through the clamping distance.

6. A surgical stapler as recited in claim 5, wherein a notch is defined in a distal end portion of the actuation shaft distal of the toothed rack for receiving and releasably retaining the engagement hook.

7. A surgical stapler as recited in claim 6, wherein movement of the actuation handle in a direction opposite the clamping stroke causes the engagement hook to release the actuation shaft, permitting the anvil to move to an open position.

8. A surgical stapler as recited in claim 7, wherein a constant force spring biases the actuation shaft in a proximal direction.

9. A surgical stapler as recited in claim 7, wherein a lift finger is provided on a flange extending from the actuation handle and is positioned to move the engagement hook out of engagement with the notch when the actuation handle is moved in said opposite direction.

10. A surgical stapler as recited in claim 7, wherein a first biasing spring is provided within the handle assembly for biasing the actuation handle in a clockwise direction and a second biasing spring is provided within the handle assembly for biasing the actuation handle in a counter-clockwise direction about a handle pivot point, the counter-clockwise direction corresponding to the direction of the clamping and actuating strokes.

11. A surgical stapler as recited in claim 5, wherein the engagement hook is configured to interact with the toothed rack to maintain the actuation shaft in a particular longitudinal position during an actuation stroke.

12. A surgical stapler as recited in claim 11, wherein the engagement hook is normally biased into engagement with the actuation shaft.

13. A surgical staple as recited in claim 12, further comprising an abutment strut operatively associated with a proximal end portion of the elongated body for maintaining the engagement hook in a position out of engagement with the actuation shaft until a disposable loading unit is operatively engaged in a distal end portion of the body, said abutment strut permitting the engagement hook to engage the actuation shaft after a disposable loading unit has been operatively engaged in a distal end portion of the elongated body.

14. A surgical stapler as recited in claim 14, wherein the disposable loading unit further comprises a carrier having a proximal portion adapted for releasable engagement within the distal end portion of the elongated body.

15. A surgical stapler as recited in claim 14, wherein the distal end portion of the elongated body and the proximal portion of the carrier include interacting portions of a bayonet-type coupling.

16. A surgical stapler as recited in claim 15, wherein biasing means are associated with the abutment strut for maintaining the interacting portions of the coupling in a spring locked position.

17. A surgical stapler as recited in claim 1, wherein the minimum linear dimension of the staple line is greater than the maximum linear distance through which the actuation shaft translates in response to a complete actuation stroke.

18. A surgical stapler as recited in claim 1, wherein the elongated body is mounted for rotation relative to a longitudinal axis of the handle assembly.

19. A surgical stapler as recited in claim 18, further comprising a rotation knob operatively mounted to a proximal portion of the elongated body adjacent the handle assembly housing for effectuating the rotation of the elongated body.

20. A surgical stapler which comprises, a handle portion, an elongated body portion extending distally from the handle portion, a coupling at a distal end of the elongated body portion for releasably engaging a disposable loading unit configured to clamp body tissue and a apply a plurality of surgical staples thereto, and an actuation assembly supported within the handle portion;

the actuation assembly being configured to actuate the disposable loading unit releasably engaged in the coupling at the distal end of the body portion, wherein the actuation assembly includes an actuation handle being movable through at least one actuation stroke to actuate the disposable loading unit;

the disposable loading unit having a plurality of surgical staples arranged in at least one linear row, wherein the actuation assembly can actuate a first disposable loading unit having a linear staple row of a first length and subsequently actuate a second disposable loading unit having a linear staple row of a second length, the first length being different than the second length; and wherein the number of strokes of the actuation handle required to actuate the disposable loading unit is dependent upon a length of the linear staple row disposed within the disposable loading unit.

21. The surgical stapler as recited in claim 20, wherein the actuation assembly is configured to actuate disposable loading units having a linear staple row ranging from about 15 mm to about 60 mm in length.

22. A surgical stapler as recited in claim 20, wherein the actuation assembly includes an elongated actuation shaft having a toothed rack provided thereon and a pawl operatively associated with the actuation handle, the pawl configured to selectively engage the toothed rack and linearly advance the actuation shaft in response to manipulation of the actuation handle.

23. A surgical stapler comprising, a handle portion, an elongated body portion extending distally from the handle portion, a coupling at a distal end of the elongated body portion for releasably engaging a disposable loading unit configured to clamp body tissue and apply at least one linear row of surgical staples thereto, an actuation assembly supported within the handle portion, the actuation assembly being configured to actuate the disposable loading unit releasably engaged in the coupling at the distal end of the body portion, and an actuation handle associated with the actuation assembly wherein a complete actuation of the disposable loading unit having at least one linear row of surgical staples requires more than one complete stroke of the actuation handle.

* * * * *

UNITED STATES PATENT AND TRADEMARK OFFICE
CERTIFICATE OF CORRECTION

| | | |
|---|---|---|
| PATENT NO. | : 5,762,256 | |
| APPLICATION NO. | : 08/520202 | |
| DATED | : June 9, 1998 | |
| INVENTOR(S) | : Mastri et al. | |

It is certified that error appears in the above-identified patent and that said Letters Patent is hereby corrected as shown below:

Delete the title page and substitute therefore the attached title page consisting of the corrected number of drawing sheets in patent.

Delete Drawing sheets 1-38 and substitute therefore the attached Drawing sheets 1-14. FIGS. 17-50 have been cancelled from the patent.

Signed and Sealed this
Ninth Day of August, 2011

David J. Kappos
*Director of the United States Patent and Trademark Office*

United States Patent [19]

Mastri et al.

[11] Patent Number: 5,762,256
[45] Date of Patent: Jun. 9, 1998

[54] SURGICAL STAPLER

[75] Inventors: Dominick L. Mastri, Bridgeport; Frank J. Viola, Sandy Hook; Thomas W. Alesi, Jr., New Fairfield; Robert J. Geiste, Milford, all of Conn.

[73] Assignee: United States Surgical Corporation, Norwalk, Conn.

[21] Appl. No.: 520,202

[22] Filed: Aug. 28, 1995

[51] Int. Cl.$^6$ .................................................. A61B 17/068
[52] U.S. Cl. ...................... 227/176.1; 227/19; 227/178.1
[58] Field of Search ............................. 227/175.1, 176.1, 227/178.1, 180.1, 19

[56] References Cited

U.S. PATENT DOCUMENTS

| | | |
|---|---|---|
| Re. 34,519 | 1/1994 | Fox et al. . |
| 3,079,606 | 3/1963 | Bobrov et al. . |
| 3,490,675 | 1/1970 | Green et al. . |
| 4,244,372 | 1/1981 | Kapitanov et al. . |
| 4,429,695 | 2/1984 | Green . |
| 4,589,413 | 5/1986 | Malyshev et al. . |
| 4,608,981 | 9/1986 | Rothfuss et al. . |
| 4,610,383 | 9/1986 | Rothfuss et al. . |
| 4,633,861 | 1/1987 | Chow et al. . |
| 4,633,874 | 1/1987 | Chow et al. . |
| 4,700,703 | 10/1987 | Resnick et al. ........................ 227/19 |
| 4,863,088 | 9/1989 | Redmond et al. . |
| 4,892,244 | 1/1990 | Fox et al. . |
| 4,991,764 | 2/1991 | Mericle . |
| 5,065,929 | 11/1991 | Schulze et al. . |
| 5,074,454 | 12/1991 | Peters . |
| 5,083,695 | 1/1992 | Foslien et al. . |
| 5,111,987 | 5/1992 | Moeinzadeh et al. . |
| 5,129,570 | 7/1992 | Schulze et al. . |
| 5,141,144 | 8/1992 | Foslien et al. . |
| 5,307,976 | 5/1994 | Olson et al. . |
| 5,312,023 | 5/1994 | Green et al. . |
| 5,318,221 | 6/1994 | Green et al. . |
| 5,326,013 | 7/1994 | Green et al. . |
| 5,332,142 | 7/1994 | Robinson et al. . |
| 5,376,095 | 12/1994 | Ortiz . |
| 5,397,046 | 3/1995 | Savage et al. . |
| 5,415,334 | 5/1995 | Williamson, IV et al. . |
| 5,415,335 | 5/1995 | Knodell, Jr. . |
| 5,433,721 | 7/1995 | Hooven et al. . |
| 5,467,911 | 11/1995 | Tsuruta et al. . |
| 5,474,566 | 12/1995 | Alesi et al. . |
| 5,486,185 | 1/1996 | Freitas et al. . |
| 5,487,500 | 1/1996 | Knodel et al. . |
| 5,507,426 | 4/1996 | Young et al. . |
| B1 5,040,715 | 4/1994 | Green et al. . |

FOREIGN PATENT DOCUMENTS

| | | |
|---|---|---|
| 0484677 | 5/1992 | European Pat. Off. . |
| 0589306 | 3/1994 | European Pat. Off. . |
| 0591946 | 4/1994 | European Pat. Off. . |
| 0656188 | 6/1995 | European Pat. Off. . |

*Primary Examiner*—Scott A. Smith

[57] ABSTRACT

A surgical device is described herein that can be used to fire different types and sizes of disposable loading units. In a preferred embodiment, the device applies parallel rows of surgical fasteners to body tissue and concomitantly forms an incision between the rows of staples during an endoscopic or laparoscopic surgical procedure. The device can be utilized with disposable loading units configured to apply linear rows of staples measuring from about 15 mm in length to about 60 mm in length and can be used to fire disposable loading units containing surgical clips and individual staples.

23 Claims, 14 Drawing Sheets